(12) United States Patent
Averett et al.

(10) Patent No.: US 7,745,415 B2
(45) Date of Patent: Jun. 29, 2010

(54) 3-β-D-RIBOFURANOSYLTHIAZOLO[4,5-*D*] PYRIMIDINE NUCLEOSIDES AND USES THEREOF

(75) Inventors: Devron R. Averett, Cardiff By The Sea, CA (US); Stephen E. Webber, San Diego, CA (US); Joseph R. Lennox, San Diego, CA (US); Erik J. Rueden, Santee, CA (US)

(73) Assignee: Anadys Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 12/015,821

(22) Filed: Jan. 17, 2008

(65) Prior Publication Data

US 2008/0255063 A1    Oct. 16, 2008

Related U.S. Application Data

(60) Division of application No. 10/861,430, filed on Jun. 7, 2004, now Pat. No. 7,321,033, which is a continuation-in-part of application No. 10/305,061, filed on Nov. 27, 2002, now Pat. No. 6,924,271.

(60) Provisional application No. 60/333,460, filed on Nov. 27, 2001.

(51) Int. Cl.
A01N 43/04      (2006.01)
A61K 31/70      (2006.01)
C07H 19/22      (2006.01)

(52) U.S. Cl. ............................................ 514/42; 514/46
(58) Field of Classification Search .................. None
See application file for complete search history.

(56) References Cited

U.S. PATENT DOCUMENTS

| | | | |
|---|---|---|---|
| 4,539,205 A | 9/1985 | Goodman et al. |
| 4,643,992 A | 2/1987 | Goodman et al. |
| 4,746,651 A | 5/1988 | Goodman |
| 4,880,784 A | 11/1989 | Robins et al. |
| 5,011,828 A | 4/1991 | Goodman et al. |
| 5,041,426 A | 8/1991 | Robins et al. |
| 5,041,542 A | 8/1991 | Robins et al. |
| 5,166,141 A | 11/1992 | Goodman et al. |
| 5,248,672 A | 9/1993 | Townsend et al. |
| 5,395,937 A | 3/1995 | Nikolaides et al. |
| 5,424,295 A | 6/1995 | Krenitsky et al. |
| 5,446,045 A | 8/1995 | Revankar et al. |
| 5,492,897 A | 2/1996 | Krenitsky et al. |
| 5,821,236 A | 10/1998 | Krenitsky et al. |
| 5,994,321 A | 11/1999 | Lewis et al. |
| 6,028,076 A | 2/2000 | Hirota et al. |
| 6,329,381 B1 | 12/2001 | Kurimoto et al. |
| 6,376,501 B1 | 4/2002 | Isobe et al. |
| 6,479,463 B1 | 11/2002 | Wang et al. |
| 6,509,320 B1 | 1/2003 | Wang et al. |
| 6,566,344 B1 | 5/2003 | Gosselin et al. |
| 6,924,271 B2 | 8/2005 | Averett et al. |
| 2002/0058635 A1 | 5/2002 | Averett |
| 2002/0173655 A1 | 11/2002 | Dellaria et al. |
| 2003/0065005 A1 | 4/2003 | Charles et al. |
| 2003/0100764 A1 | 5/2003 | Bonk et al. |
| 2003/0162806 A1 | 8/2003 | Dellaria et al. |
| 2003/0176458 A1 | 9/2003 | Dellaria et al. |
| 2003/0186949 A1 | 10/2003 | Dellaria et al. |
| 2003/0195209 A1 | 10/2003 | Dellaria et al. |
| 2003/0199461 A1 | 10/2003 | Averett et al. |
| 2004/0063658 A1 | 4/2004 | Roberts et al. |
| 2005/0004144 A1 | 1/2005 | Carson et al. |
| 2005/0054590 A1 | 3/2005 | Averett |
| 2005/0070556 A1 | 3/2005 | Averett et al. |
| 2005/0182001 A1 | 8/2005 | Averett et al. |
| 2006/0160830 A1 | 7/2006 | Webber et al. |
| 2008/0020989 A1 | 1/2008 | Haley et al. |
| 2008/0032999 A1 | 2/2008 | Haley et al. |

FOREIGN PATENT DOCUMENTS

| | | |
|---|---|---|
| EP | 0882727 | 12/1998 |
| EP | 1035123 | 9/2000 |
| EP | 1043021 | 10/2000 |
| EP | 1386923 | 2/2004 |
| WO | 89/05649 | 6/1989 |
| WO | 92/16215 | 10/1992 |
| WO | WO-94/07904 | 4/1994 |
| WO | 94/17090 | 8/1994 |

(Continued)

OTHER PUBLICATIONS

Vilček, Cytokine Handbook, Academic Press Amsterdam; Boston: 2003; vol. 1 (4th ed) pp. 3-18.*

(Continued)

*Primary Examiner*—Shaojia Anna Jiang
*Assistant Examiner*—Layla Bland
(74) *Attorney, Agent, or Firm*—Connolly Bove Lodge & Hutz LLP

(57) ABSTRACT

The invention is directed to 3-β-D-ribofuranosylthiazolo[4,5-d]pyrimidine nucleosides and pharmaceutical compositions containing such compounds that have immunomodulatory activity. The invention is also directed to the therapeutic or prophylactic use of such compounds and compositions, and to methods of treating diseases and disorders described herein, by administering effective amounts of such compounds.

12 Claims, 2 Drawing Sheets

FOREIGN PATENT DOCUMENTS

| | | |
|---|---|---|
| WO | WO-94/17043 | 8/1994 |
| WO | WO-98/17279 | 4/1998 |
| WO | WO-03/045968 | 6/2003 |

OTHER PUBLICATIONS

The Merck Manuals Online Medical Library (Acute Viral Hepatitis).*
Vippagunta et al. Advanced Drug Delivery Reviews 48 (2001) 3-26.*
U.S. Appl. No. 11/607,719, Wang et al.
U.S. Appl. No. 11/873,202, Kucera.
Akira, "Mammalian Toll-like receptors", *Current Opinion*, 2003, 15: 5-11.
Akira, "Toll-Like Receptor Signalling", *Immunology*, 2004, 4:499-511.
Alexander et al., "(Acyloxy)alkyl Carbamates as Novel Bioreversible Prodrugs for Amines: Increased Permeation through Biological Membranes", J. Med. Chem., 1988, 31:318-322.
Applequist et al., "Variable expression of Toll-like receptor in murine innate and adaptive immune cell lines", *Int. Immunol.*, 2002, 14(9):1065-74.
Barrio et al., "Regioselective Fluorination of Substituted Guanines with Dilute $F_2$: A Facile Entry to 8-Fluoroguanine Derivatives", *J. Org. Chem.*, 1996, 61:6084-6085.
Bottcher et al., "Differential regulation of Toll-like receptor mRNAs in experimental murine central nervous system infections", *Neurosci. Lett.*, 2003, 344(1):17-20.
Bruno et al., "Mouse pre-immunocytes as non-proliferating multipotent precursors of macrophages, interferon-producing cells, $CD8\alpha^+$ and $CD8\alpha^-$ dendritic cells", *Eur. J. Immunol.*, 2001, 31(11):3403-12.
Chuang et al., "Cloning and characterization of a sub-family of human Toll-like receptors: hTLR7, hTLR8 and hTLR9", *Eur. Cytokine Netw.*, Sep. 2000, 11(3):372-8.
Diebold et al, "Innate antiviral responses by means of TLR7-mediated recognition of single-stranded RNA", *Science*, 2004, 303(5663):1481-2.
Doxsee et al, "The Immune Response Modifier and Toll-like Receptor 7 Agonist S-27609 Selectively Induces IL-12 and TNF-$\alpha$ Production in $CD11c^+CD11b^+CD8^-$ Dendritic Cells", *J. Immunol.*, 2003, 171(3):1156-63).
Du et al., *Eur. Cytokine Netw.*, 2000, 11(3), 362-71.
Edwards et al., "Toll-like receptor expression in murine DC subsets: lack of TLR7 expression by $CD8\alpha^+$ DC correlates with unresponsiveness to imidazoquinolines", *Eur. J. Immunol.*, 2003, 33(4):827-33.
Fan et al., "Pyrimidines. 24. Analogues and Derivatives of 2-Amino-5-bromo-6-phenyl-4(3*H*)-pyrimidinone (ABPP)", *J. Heterocyclic Chem.*, Nov. 1993, 30:1273-1276.
Fried, et al., "5-Substituted 2-Amino-6-phenyl-4(3*H*)-pyrimidinones. Antiviral- and Interferon-Inducing Agents", *J. Med. Chem.*, 1980, 23:237-239.
Fujiwara et al., "Synthesis and Bioactivities of Novel Piperidylpyrimidine Derivatives: Inhibitors of Tumor Necrosis Factor-Alpha Production", *Bioorg. Med. Chem. Lett.*, 2000, 10(12):1317-1320.
Furneaux et al., "Improved Syntheses of 3*H*,5*H*-Pyrrolo[3,2-*d*]pyrimidines", *J. Org. Chem.*, 64 (22), 8411-8412 (1999).
Gangwar et al., "Synthesis of a Novel Esterase-Sensitive Cyclic Prodrug of a Hexapeptide Using an (Acyloxy)alkoxy Promoiety)", J. Org. Chem., 1997, 62:1356-1362.
Gibson et al., "Plasmacytoid dendritic cells produce cytokines and mature in response to the TLR7 agonists, imiquimod and resiquimod", *Cell Immunol.*, 2002, 218(1-2):74-86.
Girgis et al., "Direct C-Flycosylation of Guanine Analogues: The Synthesis and Antiviral Activity of Certain 7- and 9-Deazaguanine *C-Nucleosides*", J. Med. Chem., 1990, 33:2750-2755.
Heil et al., "The Toll-like receptor 7 (TLR7)-specific stimulus loxoribine uncovers a strong relationship within the TLR7, 8 and 9 subfamily", *Eur. J. Immunol.*, 2003, 33(11):2987-97.

Hemmi et al., "Small anti-viral compounds activate immune cells via the TLR7 MyD88-dependent signaling pathway", *Nat. Immunol.*, 2002, 3(2):196-200.
Henry et al., "Synthesis and Broad-Spectrum Antiviral Activity of 7,8-Dihydro-7-methyl-8-thioxoguanosine", *J. Med. Chem.*, 1990, 33:2127-2130.
Hirota et al., "Discovery of 8-Hydroxyadenines as a Novel Type of Interferon Inducer", *J. Med. Chem.*, 2002, 45:5419-5422.
Horng et al., "The adaptor molecule TIRAP provides signaling specificity for Toll-like receptors", *Nature*, 2002, 420(6913):329-333.
Hornung et al., "Quantitative Expression of Toll-Like Receptor 1-10 mRNA in Cellular Subsets of Human Peripheral Blood Mononuclear Cells and Sensitivity to CpG Oligodeoxynucleotides", *J. Immunol.*, 2002, 168(9):4531-4537.
International Search Report (PCT/US2004/028236) dated Mar. 14, 2005.
Isobe et al, "Synthesis and Structure-Activity Relationships of 2-Substituted-8-hydroxyadenin Derivatives as Orally Available Interferon Inducers without Emetic Side Effects", *Bioorganic & Medicinal Chemistry*, 2003, 11:3641-3647.
Ito et al., "Roles of Toll-Like Receptors in Natural Interferon-Producing Cells as Sensors in Immune Surveillance", *Hum. Immunol.*, 2002, 63(12):1120-1125.
Jarrossay, "Specialization and complementarity in microbial molecule recognition by human myeloid and plasmacytoid dendritic cells", *Eur. J. Immunol.*, 2001, 31(11) 3388-3393.
Jurk et al., "Human TLR7 or TLR8 independently confer responsiveness to the antiviral compound R-848", *Nat. Immunol.*, 2002, 3(6):499.
Kerr et al, "Isatoribine, a Toll Like Receptor 7 Agonist, Significantly Reduced Plasma Viral Load in a Proof-of-Concept Study in Patients with Chronic Hepatitis C Virus Infection".
Kini et al., "Synthesis and Antiviral Activity of Certain Guanosine Analogues in the Thiazolo[4,5-*d*]pyrimidine Ring System", *J. Med. Chem.*, 1991, 34:3006-3010.
Krenitsky et al., "6-Deoxyacyclovir: A xanthjne oxidase-activated prodrug of acyclovir", Proc. Natl. Acad. Sci., 81:3209-3213 (1984).
Kurimoto et al., "Prodrugs of 9-Benzyl-8-hydroxy-2-(2-hydroxyethylthio)adenine: Potent Interferon Inducing Agents in Monkeys", *Chem. Pharm. Bull.*, 2004, 52(4):466-469.
Kurimoto et al., "Synthesis and evaluation of 2-substituted 8-hydroxyadenines as potent inferferon inducers with improved oral bioavailabilities", *Bioorg. Med. Chem.*, 2004, 12:1091-1099.
Le Quesne et al., "Biomimetic Synthesis of Catechol Estrogens" Potentially Mutagenic Arene Oxide Intermediates in Estrogen Metabolism, *J. Med. Chem*, 1980, 23:239-240.
Lee et al., "Molecular basis for the immunostimulatory activity of guanine nucleoside analogs: activation of Toll-like receptor 7", *PNAS*, 2003, 100(11): 6646-6651.
Lewis et al., "Thiazolo[4,5-*d*]pyrimidines. Part I. Synthesis and Anti-Human Cytomegalovirus (HCMV) Activity in vitro of Certain Alkyl Derivatives", J. Het. Chem., 32, 547-56.
Lore et al, "Toll-Like Receptor Ligands Modulate Dendritic Cells to Augment Cytomegalovirus-and HIV-1-Specific T Cell Responses", *J. Immunol.*, 2003, 171(8): 4320-4328.
Mealy, "ANA-971", *Drugs of the Future*, 2004, 29(5):507.
Mealy, "ISIS-14803—20-Mer antisense phosphorothioate oligodeoxynucleotide whose sequence is: 5'GTGCmTCmATG-GTGCmACmGGTCmT-3' where Cm represents 5-methylcytidine", *Drugs of the Future*, May 2004, 29(5):526-27.
Michael et al, "Alkylpurines as Immunopotentiating Agents. Synthesis and Antiviral Activity of Certain Alkylguanines", *J. Med. Chem.*, 1993, 36:3431-3436.
Miettinen et al., "IFNs activate toll-like receptor gene expression in viral infections", *Genes Immun.*, 2001, 2(6):349-355.
Mohty et al., "IFN-$\alpha$ Skews Monocyte Differentiation into Toll-Like Receptor 7-Expressing Dendritic Cells with Potent Functional Activities", *J. Immunol.*, 2003, 171(7):3385-93.
Nagase et al.,"Expression and Function of Toll-Like Receptors in Eosinophils: Activation by Toll-Like Receptor 7 Ligand[1]", *J. Immunol.*, 2003, 171(8):3977-3982.
O'Neill, "After the Toll Rush", *Science*, 2004, 303:1481-1482.

Okada et al., "Murine thymic plasmacytoid dendritic cells", *Eur. J. Immunol.*, 2003, 33(4): 1012-9.

Pinhal-Enfield et al., "An Angiogenic Switch in Macrophages Involving Synergy between Toll-Like Receptors 2, 4, 7, and 9 and Adenosine $A_{2A}$ Receptors", *Am. J. Pathol.*, 2003, 163(2):711-721.

Pockros et al., "A Phase IIa Placeob-Controlled, Double-Blind Trial to Determine the Safety, Tolerability, PK/PD of An Oral Interferon Inducer, Resiquimod, in chronic HCV", *Gastroenterology*, 2003, 124(Suppl 1): A-766.

Pockros, "Attacking the Hepatitis C Virus with New Mechanisms of Action: Drugs in the Pipeline", *The HCV Advocate: Medical Writer's Circle*, May 2004, pp. 1-5.

Raney et al, "HEP DART 2003: Frontiers in Drug Development for Viral Hepatitis", *Expert Opin. Investig. Drugs*, 2004, 13(3):289-293.

Reitz, et al., "Small-Molecule Immunostimulants. Synthesis and Activity of 7,8-Disubstituted Guasnosines and Structurally Related Compounds", *J. Med. Chem.*, 1994, 37(21):3561-3578.

Revankar et al., "Synthesis and Antiviral/Antitumor Activities of Certain 3-Deazaguanine Nucleosides and Nucleotides", *J. Med. Chem.*, 1984, 27:1389-96.

Revankar et al., "Synthesis of Certain *N*- and *C*-Alkyl Purine Analogs", J. Het. Chem., 30, 1341-49 (1993).

Rhodes, "Discovery of immunopotentiatory drugs: current and future strategies", *Clin. Exp. Immunol.*, 2002, 130:363-369.

Rothenfusser et al., "Plasmacytoid Dendritic Cells: The Key to CpG", *Hum. Immunol.*, 2002, 63(12):1111-1119.

Sato et al., "A variety of microbial components induce tolerance to lipopolysaccharide by differentially affecting MyD88-dependent and -independent pathways", *Int. Immunol.*, 2002, 14(7):783-91.

Seela et al., "Synthese von 2-Amino-2,7-dihydro-7-(β-D-ribofuranosyl)-4H-pyrrolo[2,3-*d*]pyrimidin-4-on—7-Desazaguanosin—der Stammverbindung des Nucleosids Q", Chem. Ber., 1981, 114 (10):3395-3402.

Skulnick et al., "Pyrimidinones. 3. N-Substituted 6-Phenylpyrimidinones and Pyrimidinediones with Diuretic/Hypotensive and Antiinflammatory Activity", *J. Med. Chem.*, 1986, 29:1499-1504.

Townsend, "The Synthesis of 2-Amiono-7-β-D-ribofuranosyl)pyrrolo[2,3,d)-pyrimidin-4-one (7-Deazaguanosine), a Nucleoside Q and Q* Analog (1)", *J. Heterocyclic Chem*, Dec. 1976, 13:1363-1364.

Ulevitch, "Therapeutics Targeting the Innate Immune System", *Nature*, 2004, 4:512-520.

Yamamoto et al., "Cutting Edge: A Novel Toll/IL-1 Receptor Domain-Containing Adapter That Preferentially Activates the IFN-β Promoter in the Toll-Like Receptor Signalinig[1]", *J. Immunol.*, 2002, 169(12):6668-72.

Yamamoto et al., "Essential role for TIRAP in activation of signaling cascade shared by TLR2 and TLR4", *Nature*, 2002, 420(6913):324-9.

"Oral Interferon-Like Molecule", *Updated on New Experimental Therapies*, <http://archive.mail-list.com/pkids/msg03975.html>, Jul. 21, 2004.

International Search Report and Written Opinion (PCT/US05/45589) dated May 18, 2006.

International Search Report and Written Opinion (PCT/US2007/21830) dated Jun. 23, 2008.

Daskalov et al., Synthesis and Properties of O6-Substituted Guanosine Derivatives, Bull. Chem. Soc. Jpn., 54 (10:3076-3083 (1981).

Fathi et al., "Synthesis of 6-Substituted 2'-Deoxyguanosine Derivatives Using Trifluoroacetic Anhydride in Pyridine", Tetrahedron Letters, 31(3):319-322 (1990).

Goodman, "Role of Salvage and Phosphorylation in the Immunostimulatory Activity of C8-Substituted Guanine Ribonucleosides", J. Immunol., 14(7):2394-2399 (1988).

Hall et al., "Aldehyde Oxidase from Rabbit Liver: Specificity Toward Purines and Their Analogs", Archives of Biochemistry and Biophysics, 25(1):36-46 (1986).

International Search Report mailed Mar. 18, 2003 for PCT/US02/38001.

Jones et al., "Di- and Triester Prodrugs of the Varicella-Zoster Antiviral Agent 6-Methoxypurine Arabinoside", J. Med. Chem., 35(1):56-63 (1992).

Kini et al., "Synthesis and Antiviral Activity of Certain Guanosine Analogues in the Thiazolo[4,5-d]pyrimidine Ring System", J. Med. Chem., 34(10):3006-30010 (1991).

Krasny et al., "Allopurinol as an Inhibitor of the in vivo Formation of Acyclovir from Desiclovir", Biochem. Pharm., 35 (23):4339-4340 (1986).

Krasny et al., "Metabolism and Pharmacokinetics of a Double Prodrug of Ganiclovir in the Rat and Monkey", Drug Metabolism and Disposition, 23(11):1242-1247 (1995).

Krenitsky et al., "Xanthine Oxidase from Human Liver: Purification and Characterization", Archives of Biochemistry and Biophysics, 247(1):108-119 (1986).

Nagahara et al., "Thiazolo[4,5-d] pyrimidine Nucleosides. The Synthesis of Certain 3-B-D-Ribofuranosylthiazolo[4,5-d] pyrimidines as Potential Immunotherapeutic Agents", J. Med. Chem., 33(1):407-415 (1990).

Purifoy et al., "Review of Research Leading to New Anti-Herpesvirus Agents in Clinical Development: Valaciclovir Hydrochloride (256U, the L-Valyl Ester of Acyclovir) and 882C, a Specific Agent for Varicella Zoster Virus", Journal of Medical Virology Supplement, 1:139-145 (1993).

Reitz et al., "Small-Molecule Immunostimulants. Synthesis and Activity of 7,8-Disubstituted Guanosines and Structurally Related Compounds", J. Med. Chem., 27(21):3561-3578 (1994).

Revankar et al., "Thiazolo[4,5-d]Pyrimidines. Part II. Synthesis and Anti-human Cytomegalovirus Activity in Vitro of Certain Acyclonucleosides and Acyclonucleotides Derived from Guanine Analogue 5-Aminothiazolo[4,5-d] Pyrimidine-2,7(3H,6H)-dione", Antiviral Chemistry & Chemotherapy, 9:53-63 (1998).

Rida et al., "Synthesis of Novel Thiazolo[4,5-d]Pyrimidine Derivatives for Antimicrobial, Anti-HIV and Anticancer Investigation", Pharmazie, 51(12):927-931 (1996).

Seela et al., :Alternative d(G-C)3 and d(C-G)3 Hexanucleotides Containing 7-Deaza-2'-deoxyguanosine or 8-Aza-7- deaza-2'-deoxyguanosine in Place of dG, Nucleic Acids Res., 17(3):901-910 (1989).

Smee et al., "Broad-Spectrum Activity of 8-chloro-7-deazaguanosine Against RNA Virus Infections in Mice and Rats", Antiviral Res., 26:203-209 (1995).

Smee et al., "Broad Spectrum In Vivo Antiviral Activity of 7-Thia-8-Oxoguanoine, a Novel Immunopotentiating Agent", Antimicrobial Agents and Chemotherapy, 33(9):1487-1492 (1989).

Wong et al., "Photochemical Synthesis of 8-Hydroxyguanine Nucleosides", Methods Enzymol., 234:59-65 (1994).

Smee et al., "Immunoenhancing Properties and Antiviral Activity of 7-Deazaguanosine in Mice," Antimicrobial Agents and Chemotheraphy, Jan. 1991, p. 152-157.

International Search Report mailed Mar. 18, 2003 for PCT/US02138001.

Averett et al. Co-pending U.S. Appl. No. 10/861,430 filed Jun. 7, 2004.

* cited by examiner

3-β-D-RIBOFURANOSYLTHIAZOLO[4,5-D] PYRIMIDINE NUCLEOSIDES AND USES THEREOF

This application is a divisional of application Ser. No. 10/861,430, filed Jun. 7, 2004, which is a Continuation-In-Part of application Ser. No. 10/305,061, filed Nov. 27, 2002, now U.S. Pat. No. 6,924,271, Issued Aug. 2, 2005, which claims the benefit of appl. No. 60/333,460, filed Nov. 27, 2001.

FIELD OF THE INVENTION

The invention is directed to 3-β-D-ribofuranosylthiazolo [4,5-d]pyrimidine nucleosides and pharmaceutical compositions containing such compounds that have immunomodulatory activity. The invention is also directed to the therapeutic or prophylactic use of such compounds and compositions, and to methods of treating diseases and disorders described herein, by administering effective amounts of such compounds.

BACKGROUND OF THE INVENTION

The last few decades have seen significant efforts expended in exploring possible therapeutic uses of D- and L-purine nucleoside analogs. A number of nucleoside analogs are currently being marketed as antiviral drugs, including the HIV reverse transcriptase inhibitors (AZT, ddI, ddC, d4T, and 3TC).

A variety of D- and L-purine nucleoside analogs have also been explored in search of immunomodulators. Guanosine analogs having substituents at the 7- and/or 8-positions, for example, have been shown to stimulate the immune system. See Reitz et al, *J. Med. Chem.*, 37, 3561-78 (1994); Michael et al., *J. Med. Chem.*, 36, 3431-36 (1993). In other research, U.S. Pat. No. 5,821,236 to Krenitsky et al. discloses 6-alkoxy derivatives of arabinofuranosyl purine derivatives that are useful for tumor therapy. Also reported in U.S. Pat. No. 5,539,098 to Krenitsky et al. are inhibitors of varicella zoster virus, including 5'-O-proprionyl and 5'-O-butyryl esters of 2-amino-6-methoxy-9-(β-D-arabinofuranosyl)-9H-purine. 7-Deazaguanosine and analogs have been shown to exhibit antiviral activity in mice against a variety of RNA viruses, even though the compound lacks antiviral properties in cell culture. 3-Deazaguanine nucleosides and nucleotides have also demonstrated significant broad spectrum antiviral activity against certain DNA and RNA viruses. Revankar et al., *J. Med. Chem.*, 27, 1489-96 (1984). Certain 7- and 9-deazaguanine C-nucleosides exhibit the ability to protect against a lethal challenge of Semliki Forest virus. Girgis et al., *J. Med. Chem.*, 33, 2750-55 (1990). Selected 6-sulfenamide and 6-sulfinamide purine nucleosides are disclosed in U.S. Pat. No. 4,328,336 to Robins et al. as having demonstrated significant antitumor activity.

Certain pyrimido[4,5-d]pyrimidine nucleosides are disclosed in U.S. Pat. No. 5,041,542 to Robins et al. as being effective in treatment against L1210 in BDF1 mice. These particular nucleosides were suggested to be as a result of their role as immunomodulators. See Bonnet et al., *J. Med. Chem.*, 36, 635-53 (1993). Also, Wang et al. (WIPO International Publication No. WO 98/16184) report that purine L-nucleoside compounds and analogs thereof were used to treat an infection, infestation, a neoplasm, an autoimmune disease, or to modulate aspects of the immune system. In addition, 3-β-D-ribofuranosylthiazolo[4,5-d]pyrimidines demonstrating significant immunoactivity, including murine spleen cell proliferation and in vivo activity against Semliki Forest virus, are disclosed U.S. Pat. Nos. 5,041,426 and 4,880,784 to Robins et al.

One possible target of immunomodulation involves stimulation or suppression of Th1 and Th2 lymphokines. Type I (Th1) cells produce interleukin 2 (IL-2), tumor necrosis factor (TNFα) and interferon gamma (IFNγ) and they are responsible primarily for cell-mediated immunity such as delayed type hypersensitivity and antiviral immunity. Type 2 (Th2) cells produce interleukins, IL-4, IL-5, IL-6, IL-9, IL-10, and IL-13 and are primarily involved in assisting humoral immune responses such as those seen in response to allergens. See, e.g., Mosmann, *Annu. Rev. Immunol*, 7, 145-73 (1989). D-guanosine analogs have been shown to elicit various effects on lymphokines IL-1, IL-6, INFα and TNFα (indirectly) in vitro (Goodman, *Int. J. Immunopharmacol,* 10, 579-88 (1988); U.S. Pat. No. 4,746,651 to Goodman) and in vivo (Smee et al., *Antiviral Res.*, 15, 229 (1991); Smee et al., *Antimicrobial Agents and Chemotherapy,* 33, 1487-92 (1989)). However, the ability of the D-guanosine analogs such as 7-thio-8-oxoguanosine to modulate Type 1 or Type 2 cytokines directly in T cells was ineffective or had not been described.

Moreover, it is known that the oral administration of many purine nucleoside analogs are subject to difficulties arising from poor absorption, poor solubility, or degradation in the digestive tract as a result of acidic or alkaline conditions or the action of enzymes, and/or combinations of these phenomena. Thus there remains a need for purine nucleoside analogs with improved oral availability, tolerability, and administration that are used to modulate aspects of the immune system.

SUMMARY OF THE INVENTION

The present invention has addressed this need by the discovery of 3-β-D-ribofuranosylthiazolo[4,5-d]pyrimidine nucleosides, pharmaceutically acceptable prodrugs, pharmaceutically active metabolites, pharmaceutically acceptable salts, and pharmaceutically acceptable solvates thereof (such compounds, prodrugs, metabolites, salts, and solvates are collectively referred to as "agents") described below, which are useful as immunomodulators.

In another embodiment, the present invention encompasses a method of treating or preventing a hepatitis C virus infection in a patient in need thereof comprising administering to the patient a therapeutically or prophylactically effective amount of a 3-β-D-ribofuranosylthiazolo[4,5-d]pyrimidine nucleoside.

In a general aspect, the invention relates to compounds of Formula I

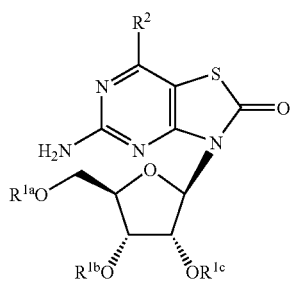

I wherein:

$R^{1a}$, $R^{1b}$, and $R^{1c}$ are independently H, —C(O)$R^3$, a racemic, L-, or D-amino acid group —C(O)CH$_2$NHR$^4$, —C(O)CH(C$_{1-6}$ alkyl)NHR$^4$, or $R^{1b}$ and $R^{1c}$ are collectively —C(O)—, which together with the oxygen atoms forms a five-membered carbonate ring;

$R^2$ is H, OR$^5$, or N(R$^6$)$_2$;

$R^3$ is a C$_{1-18}$ alkyl;

$R^4$ is H, —C(O)CH(C$_{1-6}$ alkyl)NH$_2$, or —C(O)CH(CH$_2$-aryl)NH$_2$;

$R^5$ is independently H, C$_{1-6}$ alkyl, C$_{3-7}$ alkenyl, C$_{3-7}$ alkynyl, —(CR$^7$R$^8$)$_t$(C$_6$-C$_{10}$ aryl), —(CR$^7$R$^8$)$_t$(C$_3$-C$_{10}$ cycloalkyl), —(CR$^7$R$^8$)$_t$(C$_4$-C$_{10}$ heterocyclic), —(CR$^7$R$^8$)$_{t\geq1}$OH, —(CR$^7$R$^8$)$_{t\geq0}$CO$_2$C$_{1-18}$ alkyl, and —(CR$^7$R$^8$)$_{t\geq0}$N(R$^9$)CO$_2$C$_{1-8}$ alkyl, and SO$_2$(aryl), wherein t is an integer from 0 to 6 unless otherwise indicated, and wherein the alkyl, alkenyl, alkynyl, aryl, cycloalkyl, and heterocyclic moieties of the foregoing groups are optionally substituted with substituents independently selected from halo, cyano, nitro, trifluoromethyl, trifluoromethoxy, C$_1$-C$_6$ alkyl, C$_2$-C$_6$ alkenyl, C$_2$-C$_6$ alkynyl, hydroxy, C$_1$-C$_6$ alkoxy, —NH$_2$, —NH-alkyl, —N(alkyl)$_2$, —NH-aryl, —N(alkyl)(aryl), —N(aryl)$_2$, —NHCHO, —NHC(O)alkyl, —NHC(O)aryl, —N(alkyl)C(O)H, —N(alkyl)C(O)alkyl, —N(aryl)C(O)H, —N(aryl)C(O)alkyl, —NHCO$_2$alkyl, —N(alkyl)CO$_2$alkyl, —NHC(O)NH$_2$, —N(alkyl)C(O)NH$_2$, —NHC(O)NH-alkyl, —NHC(O)N(alkyl)$_2$, —N(alkyl)C(O)NH-alkyl, N(alkyl)C(O)N(alkyl)$_2$, —NHSO$_2$-alkyl, —N(alkyl)SO$_2$-alkyl, —C(O)alkyl, —C(O)aryl, —OC(O)alkyl, —OC(O)aryl, —CO$_2$-alkyl, —CO$_2$-aryl, —CO$_2$H, —C(O)NH$_2$, —C(O)NH-alkyl, —C(O)N(alkyl)$_2$, —C(O)NH-aryl, —C(O)N(aryl)$_2$, —C(O)N(alkyl)(aryl), —S(O)alkyl, —S(O)aryl, —SO$_2$alkyl, —SO$_2$aryl, —SO$_2$NH$_2$, —SO$_2$NH-alkyl, and —SO$_2$N(alkyl)$_2$;

$R^6$ is independently H, C$_{1-6}$ alkyl, C$_3$-C$_{10}$ cycloalkyl, or together with nitrogen forms a 5- or 6-membered heterocyclic ring;

$R^7$ and $R^8$ are independently H, C$_{1-6}$ alkyl, C$_{2-6}$ alkenyl, or C$_{2-6}$ alkynyl; and $R^9$ is H, C$_{1-6}$ alkyl, or —CH$_2$-aryl;

In one embodiment, the invention relates to compounds of the Formula I, wherein $R^2$ is H or OR$^5$.

In another embodiment, the invention relates to compounds of the Formula I wherein $R^{1a}$, $R^{1b}$, and $R^{1c}$ are independently H, —C(O)R$^3$, a racemic, L-, or D-amino acid group —C(O)CH(C$_{1-6}$ alkyl)NH$_2$; $R^2$ is OR$^5$; $R^3$ is a C$_{1-18}$ alkyl; $R^5$ is independently C$_{1-6}$ alkyl, C$_{3-7}$ alkenyl, C$_{3-7}$ alkynyl, —(CR$^7$R$^8$)$_t$(C$_6$-C$_{10}$ aryl), —(CR$^7$R$^8$)$_t$(C$_4$-C$_{10}$ heterocyclic), and —(CR$^7$R$^8$)$_{t\geq0}$N(R$^9$)CO$_2$C$_{1-18}$ alkyl, wherein t is an integer from 0 to 4 unless otherwise indicated, and wherein the alkyl, alkenyl, aryl, and heterocyclic moieties of the foregoing groups are optionally substituted with 1 to 3 substituents independently selected from halo, cyano, nitro, trifluoromethyl, trifluoromethoxy, C$_1$-C$_6$ alkyl, C$_2$-C$_6$ alkenyl, C$_2$-C$_6$ alkynyl, hydroxy, C$_1$-C$_6$ alkoxy, —CO$_2$-alkyl, —CO$_2$-aryl, —OC(O)alkyl, and —OC(O)aryl; $R^7$ and $R^8$ are independently H, C$_{1-6}$ alkyl, or C$_{2-6}$ alkenyl; and $R^9$ is H, —CH$_3$, or —CH$_2$CH$_3$.

In another embodiment, the invention relates to compounds of the Formula I selected from

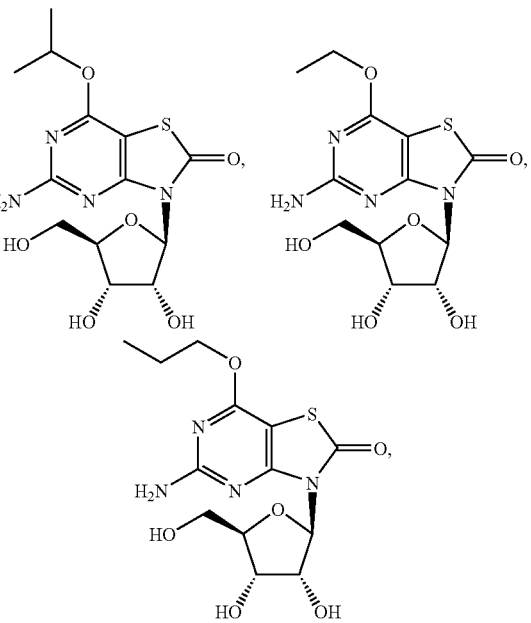

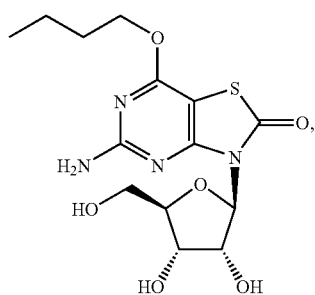

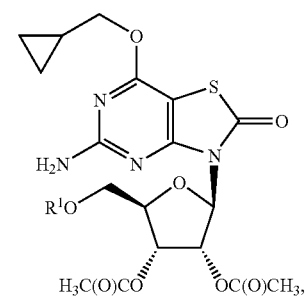

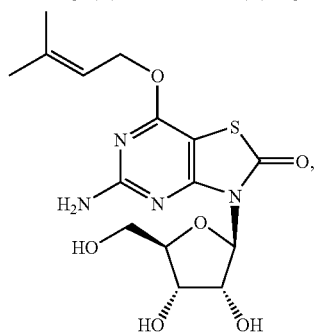

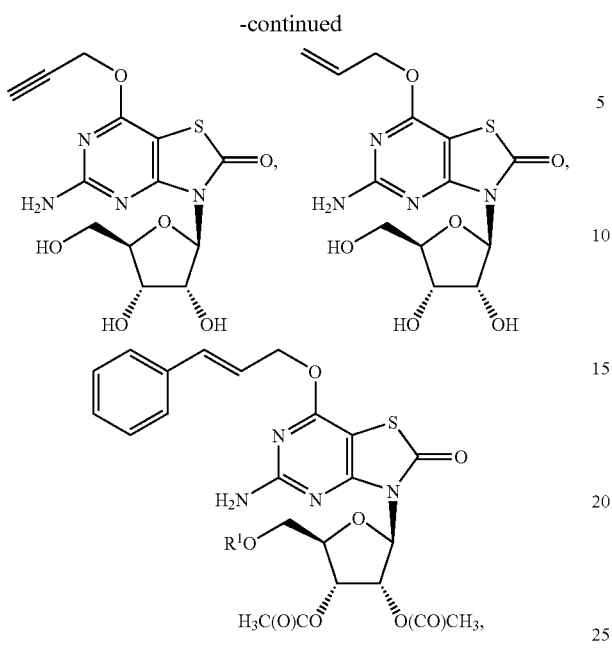
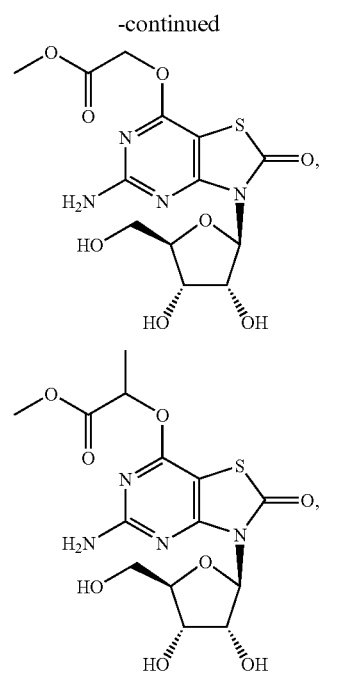
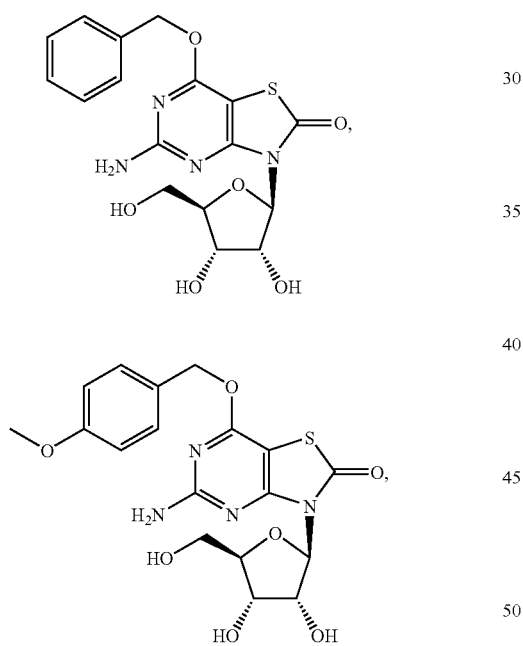
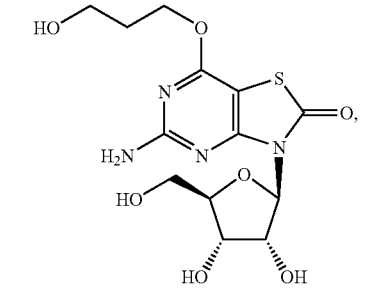
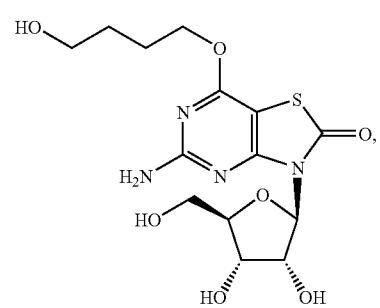
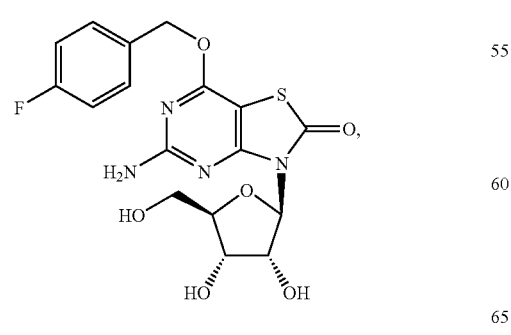
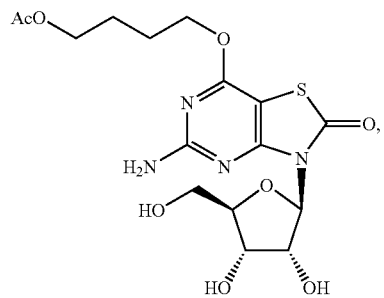

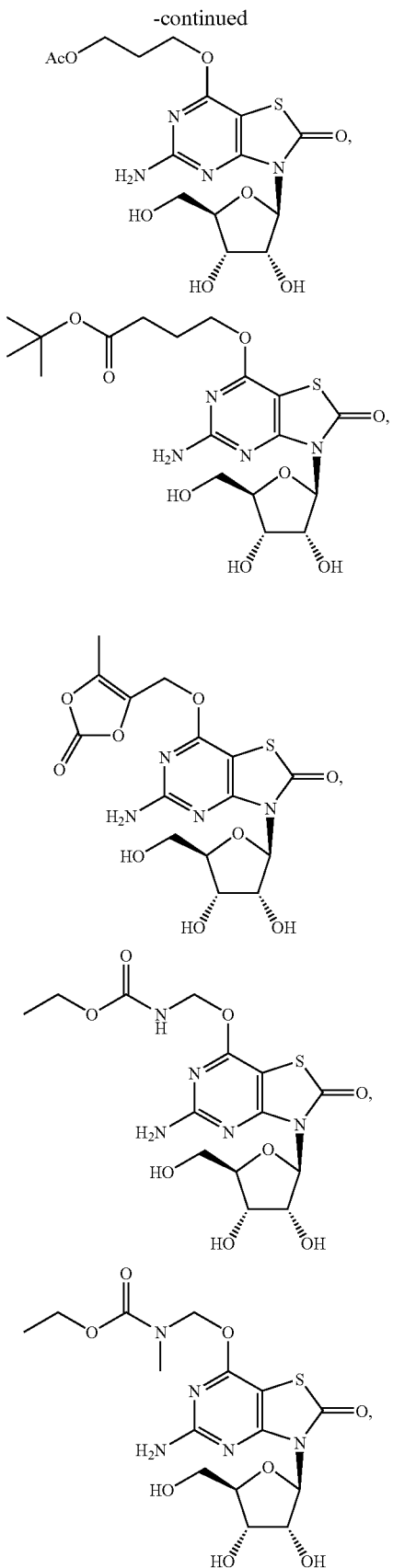
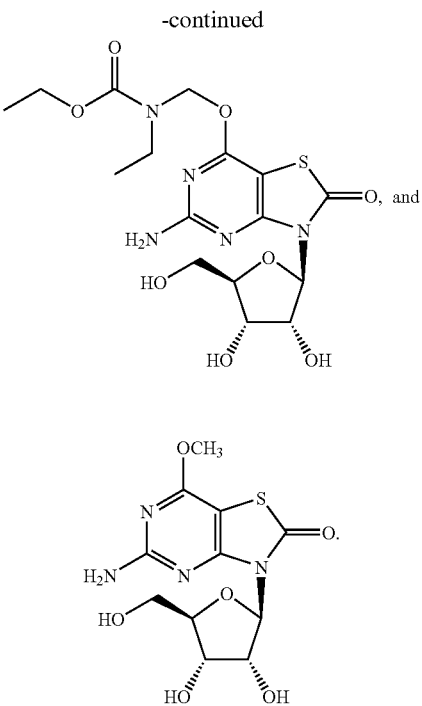

In another embodiment, the invention relates to compounds of the Formula I, wherein $R^2$ is H.

In another embodiment, the invention relates to compounds of the Formula I wherein $R^{1a}$, $R^{1b}$, and $R^{1c}$ are independently H, —C(O)$R^3$, a racemic, L-, or D-amino acid group —C(O)CH($C_{1-6}$ alkyl)NH$_2$; $R^2$ is H; and $R^3$ is a $C_{1-18}$ alkyl.

In another embodiment, the invention relates to compounds of the Formula I wherein $R^{1a}$, $R^{1b}$, and $R^{1c}$ are independently H, —C(O)$R^3$, a racemic, L-, or D-amino acid group —C(O)CH(CH(CH$_3$)$_2$)NH$_2$; $R^2$ is H; and $R^3$ is CH$_3$.

In another embodiment, the invention relates to compounds of the Formula I, wherein $R^{1a}$, $R^{1b}$, and $R^{1c}$ are independently H or —C(O)$R^3$, wherein $R^2$ is H; and $R^3$ is CH$_3$.

In another embodiment, the invention relates to compounds of the Formula I, wherein $R^{1a}$ is H and $R^{1b}$ and $R^{1c}$ are —C(O)$R^3$; $R^2$ is H, and $R^3$ is CH$_3$.

In another embodiment, compounds of the invention are selected from:

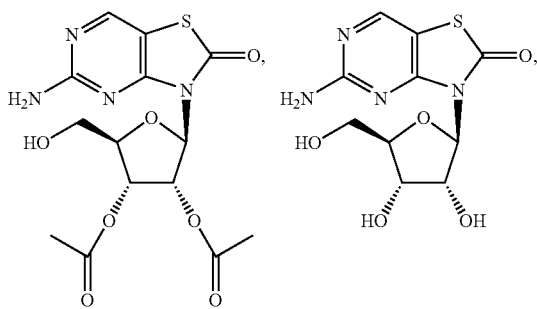

-continued

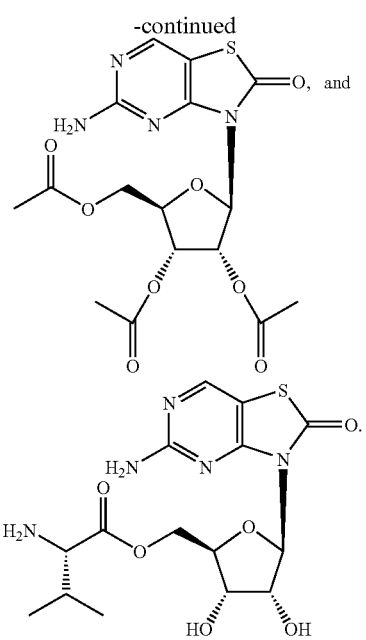

In yet another embodiment, a compound of the invention is

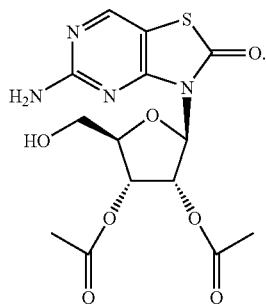

The invention is also directed to pharmaceutically acceptable prodrugs, pharmaceutically active metabolites, pharmaceutically acceptable salts, and pharmaceutically acceptable solvates of the compounds, prodrugs, or metabolites of Formula I. Advantageous methods of making the compounds of Formula I are also described.

The compounds of Formula I are useful as immune system enhancers and have certain immune system properties including modulation, mitogenicity, augmentation, and/or potentiation or they are intermediates for compounds that have these properties. The compounds are expected to express effects on at least the natural killer, macrophages, and lymphocyte cells of the immune system of a host. Because of these properties they are useful as antiviral and antitumor agents or as intermediates for antiviral and antitumor agents. They can be used to treat an affected host by serving as the active ingredients of suitable pharmaceutical compositions.

In one aspect of the invention, Formula I compounds are utilized to treat the full range of viral diseases in mammals, including humans, by administering to the mammal a therapeutically effective amount of the compounds. Viral diseases contemplated to be treated with Formula I compounds include acute and chronic infections caused by both RNA and DNA viruses. Without limiting in any way the range of viral infections that may be treated, compounds of Formula I are particularly useful in the treatment of infections caused by adenovirus, cytomegalovirus, hepatitis A virus (HAV), hepatitis B virus (HBV), flaviviruses including Yellow Fever virus and hepatitis C virus (HCV), herpes simplex type 1 and 2, herpes zoster, human herpesvirus 6, human immunodeficiency virus (HIV), human papilloma virus (HPV), influenza A virus, influenza B virus, measles, parainfluenza virus, poliovirus, poxvirus (including smallpox and monkeypox virus), rhinovirus, respiratory syncytial virus (RSV), multiple families of viruses that cause hemorrhagic fevers, including the Arenaviruses (LCM, Junin virus, Machup virus, Guanarito virus, and Lassa Fever), the Bunyaviruses (Hanta viruses and Rift Valley Fever) and Filoviruses (Ebola and Marburg virus), a range of viral encephalitides including West Nile virus, LaCrosse virus, California Encephalitis virus, Venezuelan Equine Encephalitis virus, Eastern Equine Encephalitis virus, Western Equine Encephalitis virus, Japanese Encephalitis virus, Kysanur Forest virus, and tickborne viruses such as Crimean-Congo Hemorrhagic fever virus.

In another aspect of the invention, Formula I compounds are utilized to treat bacterial, fungal, and protozoal infections in mammals by administering to the mammal a therapeutically effective amount of the compounds. The full range of pathogenic microorganisms is contemplated to be treatable by the compounds of the present invention, including without limitation those organisms that are resistant to antibiotics. The ability of Formula I compounds to activate multiple components of the immune system bypasses resistance mechanisms commonly found to reduce susceptibility to antibiotics, and thus treatment of infections in a mammal caused by such resistant microorganisms by Formula I compounds is a particular utility of the present invention.

In another aspect of the invention, Formula I compounds are utilized to treat tumors in mammals by administering to the mammal a therapeutically effective amount of the compounds. Tumors or cancers contemplated to be treated include those caused by virus, and the effect may involve inhibiting the transformation of virus-infected cells to a neoplastic state, inhibiting the spread of viruses from transformed cells to other normal cells, and/or arresting the growth of virus-transformed cells. The compounds of Formula I are expected to be useful against a broad spectrum of tumors including but not limited to carcinomas, sarcomas, and leukemias. Included in such a class are mammary, colon, bladder, lung, prostate, stomach, and pancreas carcinomas and lymphoblastic and myeloid leukemias.

In another aspect of the invention, a method of treating a mammal comprises administering a therapeutically and/or prophylactically effective amount of a pharmaceutical containing a compound of the invention. In this aspect the effect may relate to modulation of some portion of the mammal's immune system, especially modulation of cytokine activities of Th1 and Th2, including but not restricted to the interleukin family, e.g., IL-1 through IL-12, and other cytokines such as TNF alpha, and interferons including interferon alpha, interferon theta, and interferon gamma, and their downstream effectors. Where modulation of Th1 and Th2 cytokines occurs, it is contemplated that the modulation may include stimulation of both Th1 and Th2, suppression of both Th1 and Th2, stimulation of either Th1 or Th2, and suppression of the other, or a bimodal modulation in which one effect on Th1/Th2 levels (such as generalized suppression) occurs at a high concentration, while another effect (such as stimulation of either Th1 or Th2 and suppression of the other) occurs at a lower concentration.

In another aspect of the invention, pharmaceutical compositions containing a compound of Formula I are administered in a therapeutically effective dose to a mammal that is receiving anti-infective drugs not included in Formula I. In a preferred aspect of this invention, the pharmaceutical compositions containing a compound of Formula I are administered in a therapeutically effective dose with anti-infective drug(s) that act directly upon the infectious agent to inhibit the growth of or kill the infectious agent.

In another aspect, the invention encompasses a method for treating or preventing hepatitis C virus infection in a mammal in need thereof, preferably in a human in need thereof.

In another aspect, the invention encompasses a method for treating or preventing hepatitis C virus infection in a patient in need thereof, comprising administering to the patient a therapeutically or prophylactically effective amount of a compound of Formula I and a pharmaceutically acceptable excipient, carrier, or vehicle.

In a another aspect, the invention encompasses a method for treating or preventing hepatitis C virus infection in a patient in need thereof, comprising administering to the patient a therapeutically or prophylactically effective amount of a compound of Formula I and an additional therapeutic agent, preferably an additional antiviral agent.

In a preferred aspect of the invention, a pharmaceutical composition comprising a therapeutically effective amount of a compound according to Formula I provides for improved oral availability and administration as an immunomodulator. In another preferred aspect of the invention, a pharmaceutical composition comprising a therapeutically effective amount of a compound according to Formula I provides for masking the active structure as the agent passes through lymphoid tissue lining the stomach, thereby minimizing activation of this tissue and allowing for improved oral tolerability.

DETAILED DESCRIPTION OF THE INVENTION AND PREFERRED EMBODIMENTS

Figure 1:
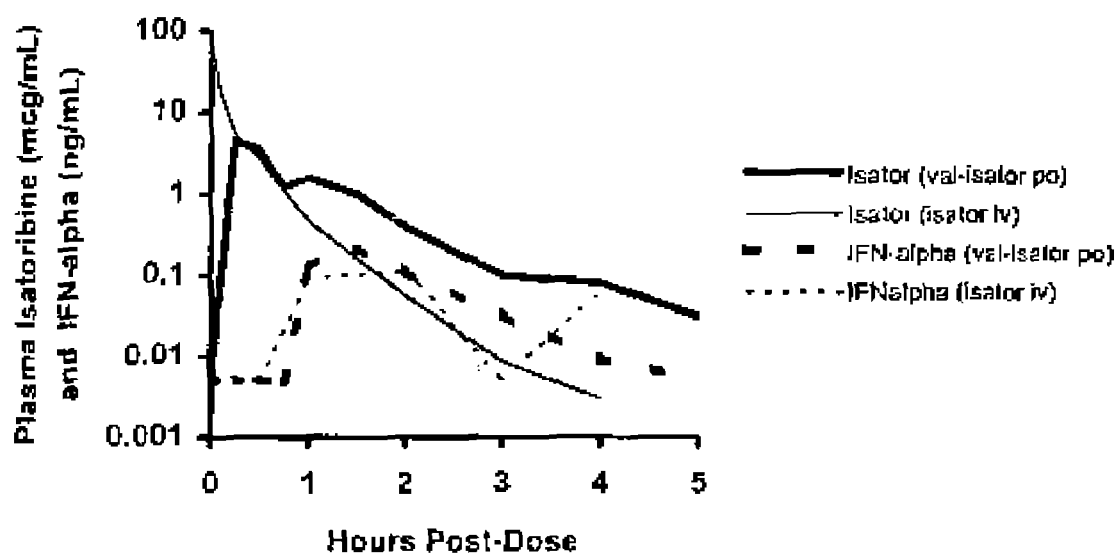
FIG. 1 is a graphical depiction of plasma levels of isatoribine (1) and interferon alpha in mice.

Where the following terms are used in this specification, they are used as defined below:

The terms "comprising" and "including" are used herein in their open, non-limiting sense.

The term "nucleoside" refers to a compound composed of any pentose or modified pentose moiety attached to a specific position of a heterocycle or to the natural position of a purine (9-position) or pyrimidine (1-position) or to the equivalent position in an analog.

The term "purine" refers to nitrogenous bicyclic heterocycles.

The term "pyrimidine" refers to nitrogenous monocyclic heterocycles.

The term "D-nucleosides" refers to the nucleoside compounds that have a D-ribose sugar moiety (e.g., Adenosine).

The term "L-nucleosides" refers to the nucleoside compounds that have a L-ribose sugar moiety.

The term "alkyl", as used herein, unless otherwise indicated, includes saturated monovalent hydrocarbon radicals having straight, branched, or cyclic moieties (including fused and bridged bicyclic and spirocyclic moieties), or a combination of the foregoing moieties. For an alkyl group to have cyclic moieties, the group must have at least three carbon atoms.

The term "alkenyl", as used herein, unless otherwise indicated, includes alkyl moieties having at least one carbon-carbon double bond wherein alkyl is as defined above and including E and Z isomers of said alkenyl moiety.

The term "alkynyl", as used herein, unless otherwise indicated, includes alkyl moieties having at least one carbon-carbon triple bond wherein alkyl is as defined above.

The term "alkoxy", as used herein, unless otherwise indicated, includes O-alkyl groups wherein alkyl is as defined above.

The term "Me" means methyl, "Et" means ethyl, and "Ac" means acetyl.

The term "cycloalkyl", as used herein, unless otherwise indicated refers to a non-aromatic, saturated or partially saturated, monocyclic or fused, spiro or unfused bicyclic or tricyclic hydrocarbon referred to herein containing a total of from 3 to 10 carbon atoms, preferably 5-8 ring carbon atoms. Exemplary cycloalkyls include monocyclic rings having from 3-7, preferably 3-6, carbon atoms, such as cyclopropyl, cyclobutyl, cyclopentyl, cyclohexyl, cycloheptyl and the like. Illustrative examples of cycloalkyl are derived from, but not limited to, the following:

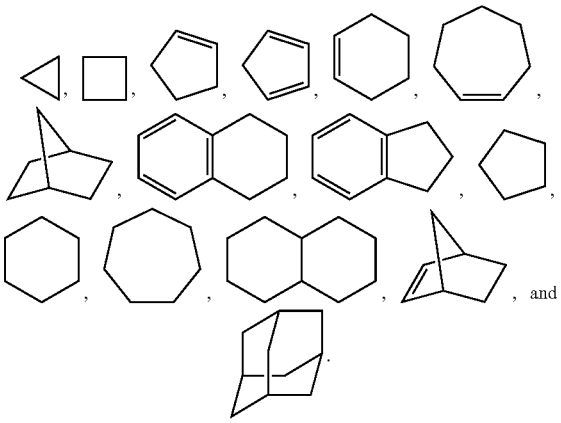

The term "aryl", as used herein, unless otherwise indicated, includes an organic radical derived from an aromatic hydrocarbon by removal of one hydrogen, such as phenyl or naphthyl.

The term "4-10 membered heterocyclic", as used herein, unless otherwise indicated, includes aromatic and non-aromatic heterocyclic groups containing one to four heteroatoms each selected from O, S and N, wherein each heterocyclic group has from 4-10 atoms in its ring system, and with the proviso that the ring of said group does not contain two adjacent O or S atoms. Non-aromatic heterocyclic groups include groups having only 4 atoms in their ring system, but aromatic heterocyclic groups must have at least 5 atoms in their ring system. The heterocyclic groups include benzofused ring systems. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). The 4-10 membered heterocyclic may be optionally substituted on any ring carbon, sulfur, or nitrogen atom(s) by one to two oxo, per ring. An example of a heterocyclic group wherein 2 ring carbon atoms are substituted with oxo moieties is 1,1-dioxo-thiomorpholinyl. Other illustrative examples of 4-10 membered heterocyclic are derived from, but not limited to, the following:

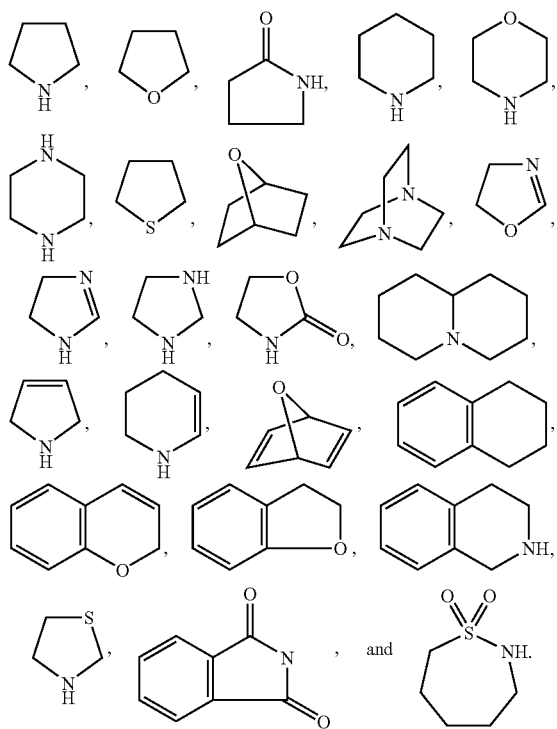

In the compounds of Formula I where terms such as $(CR^7R^8)_t$ are used, $R^7$ and $R^8$ may vary with each iteration of t above 1. For instance, where t is 2 the term $(CR^7R^8)_t$ may equal —$CH_2CH_2$—, or —$CH(CH_3)C(CH_2CH_3)(CH_2CH_2CH_3)$—, or any number of similar moieties falling within the scope of the definitions of $R^7$ and $R^8$.

The term "immunomodulator" refers to natural or synthetic products capable of modifying the normal or aberrant immune system through stimulation or suppression.

The term "preventing" refers to the ability of a compound or composition of the invention to prevent a disease identified herein in patients diagnosed as having the disease or who are at risk of developing such disease. The term also encompasses preventing further progression of the disease in patients who are already suffering from or have symptoms of such disease.

The term "patient" or "subject" means an animal (e.g., cow, horse, sheep, pig, chicken, turkey, quail, cat, dog, mouse, rat, rabbit, guinea pig, etc.) or a mammal, including chimeric and transgenic animals and mammals. In the treatment or prevention of HCV infection, the term "patient" or "subject" preferably means a monkey or a human, most preferably a human. In a specific embodiment the patient or subject is infected by or exposed to the hepatitis C virus. In certain embodiments, the patient is a human infant (age 0-2), child (age 2-17), adolescent (age 12-17), adult (age 18 and up) or geriatric (age 70 and up) patient. In addition, the patient includes immunocompromised patients such as HIV positive patients, cancer patients, patients undergoing immunotherapy or chemotherapy. In a particular embodiment, the patient is a healthy individual, i.e., not displaying symptoms of other viral infections.

The term a "therapeutically effective amount" refers to an amount of the compound of the invention sufficient to provide a benefit in the treatment or prevention of viral disease, to delay or minimize symptoms associated with viral infection or viral-induced disease, or to cure or ameliorate the disease or infection or cause thereof. In particular, a therapeutically effective amount means an amount sufficient to provide a therapeutic benefit in vivo. Used in connection with an amount of a compound of the invention, the term preferably encompasses a non-toxic amount that improves overall therapy, reduces or avoids symptoms or causes of disease, or enhances the therapeutic efficacy of or synergies with another therapeutic agent.

The term a "prophylactically effective amount" refers to an amount of a compound of the invention or other active ingredient sufficient to result in the prevention of infection, recurrence or spread of viral infection. A prophylactically effective amount may refer to an amount sufficient to prevent initial infection or the recurrence or spread of the infection or a disease associated with the infection. Used in connection with an amount of a compound of the invention, the term preferably encompasses a non-toxic amount that improves overall prophylaxis or enhances the prophylactic efficacy of or synergies with another prophylactic or therapeutic agent.

The term "in combination" refers to the use of more than one prophylactic and/or therapeutic agents simultaneously or sequentially and in a manner that their respective effects are additive or synergistic.

The term "treating" refers to:
(i) preventing a disease, disorder, or condition from occurring in an animal that may be predisposed to the disease, disorder and/or condition, but has not yet been diagnosed as having it;
(ii) inhibiting the disease, disorder, or condition, i.e., arresting its development; and
(iii) relieving the disease, disorder, or condition, i.e., causing regression of the disease, disorder, and/or condition.

The terms "α" and "β" indicate the specific stereochemical configuration of a substituent at an asymmetric carbon atom in a chemical structure as drawn. The compounds described herein are all in the D-furanosyl configuration.

The compounds of the invention may exhibit the phenomenon of tautomerism. While Formula I cannot expressly depict all possible tautomeric forms, it is to be understood that Formula I is intended to represent any tautomeric form of the depicted compound and are not to be limited merely to a specific compound form depicted by the formula drawings.

For example, it is understood for Formula I that regardless of whether or not the substituents are shown in their enol or their keto form, they represent the same compound (as shown in the example below).

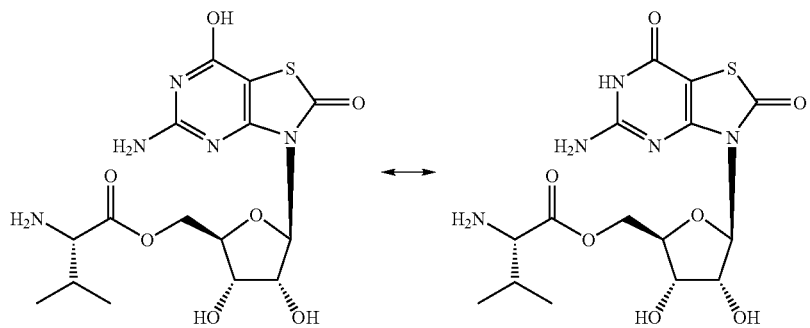

Some of the inventive compounds may exist as single stereoisomers (i.e., essentially free of other stereoisomers), racemates, and/or mixtures of enantiomers and/or diastereomers. All such single stereoisomers, racemates and mixtures thereof are intended to be within the scope of the present invention. Preferably, the inventive compounds that are optically active are used in optically pure form.

As generally understood by those skilled in the art, an optically pure compound having one chiral center (i.e., one asymmetric carbon atom) is one that consists essentially of one of the two possible enantiomers (i.e., is enantiomerically pure), and an optically pure compound having more than one chiral center is one that is both diastereomerically pure and enantiomerically pure. Preferably, the compounds of the present invention are used in a form that is at least 90% optically pure, that is, a form that contains at least 90% of a single isomer (80% enantiomeric excess ("e.e.") or diastereomeric excess ("d.e.")), more preferably at least 95% (90% e.e. or d.e.), even more preferably at least 97.5% (95% e.e. or d.e.), and most preferably at least 99% (98% e.e. or d.e.).

Additionally, the Formula I is intended to cover solvated as well as unsolvated forms of the identified structures. For example, Formula I includes compounds of the indicated structure in both hydrated and non-hydrated forms. Other examples of solvates include the structures in combination with isopropanol, ethanol, methanol, DMSO, ethyl acetate, acetic acid, or ethanolamine.

In addition to compounds of Formula I, the invention includes pharmaceutically acceptable prodrugs, pharmaceutically active metabolites, and pharmaceutically acceptable salts of such compounds and metabolites.

"A pharmaceutically acceptable prodrug" is a compound that may be converted under physiological conditions or by solvolysis to the specified compound or to a pharmaceutically acceptable salt of such compound prior to exhibiting its pharmacological effect (s). Typically, the prodrug is formulated with the objective(s) of improved chemical stability, improved patient acceptance and compliance, improved bioavailability, prolonged duration of action, improved organ selectivity, improved formulation (e.g., increased hydrosolubility), and/or decreased side effects (e.g., toxicity). The prodrug can be readily prepared from the compounds of Formula I using methods known in the art, such as those described by Burger's Medicinal Chemistry and Drug Chemistry, 1, 172-178, 949-982 (1995). See also Bertolini et al., J. Med. Chem., 40, 2011-2016 (1997); Shan, et al., J. Pharm. Sci., 86 (7), 765-767; Bagshawe, Drug Dev. Res., 34, 220-230 (1995); Bodor, Advances in Drug Res., 13, 224-331 (1984); Bundgaard, Design of Prodrugs (Elsevier Press 1985); Larsen, Design and Application of Prodrugs, Drug Design and Development (Krogsgaard-Larsen et al., eds., Harwood Academic Publishers, 1991); Dear et al., J. Chromatogr. B, 748, 281-293 (2000); Spraul et al., J. Pharmaceutical &Biomedical Analysis, 10, 601-605 (1992); and Prox et al., Xenobiol., 3, 103-112 (1992).

"A pharmaceutically active metabolite" is intended to mean a pharmacologically active product produced through metabolism in the body of a specified compound or salt thereof. After entry into the body, most drugs are substrates for chemical reactions that may change their physical properties and biologic effects. These metabolic conversions, which usually affect the polarity of the Formula I compounds, alter the way in which drugs are distributed in and excreted from the body. However, in some cases, metabolism of a drug is required for therapeutic effect. For example, anticancer drugs of the anti-metabolite class must be converted to their active forms after they have been transported into a cancer cell.

Since most drugs undergo metabolic transformation of some kind, the biochemical reactions that play a role in drug metabolism may be numerous and diverse. The main site of drug metabolism is the liver, although other tissues may also participate.

A feature characteristic of many of these transformations is that the metabolic products, or "metabolites," are more polar than the parent drugs, although a polar drug does sometime yield a less polar product. Substances with high lipid/water partition coefficients, which pass easily across membranes, also diffuse back readily from tubular urine through the renal tubular cells into the plasma. Thus, such substances tend to have a low renal clearance and a long persistence in the body. If a drug is metabolized to a more polar compound, one with a lower partition coefficient, its tubular reabsorption will be greatly reduced. Moreover, the specific secretory mechanisms for anions and cations in the proximal renal tubules and in the parenchymal liver cells operate upon highly polar substances.

As a specific example, phenacetin (acetophenetidin) and acetanilide are both mild analgesic and antipyretic agents, but are transformed within the body to a more polar and more effective metabolite, p-hydroxyacetanilid (acetaminophen), which is widely used today. When a dose of acetanilide is given to a person, the successive metabolites peak and decay in the plasma sequentially. During the first hour, acetanilide is the principal plasma component. In the second hour, as the acetanilide level falls, the metabolite acetaminophen concentration reaches a peak. Finally, after a few hours, the principal plasma component is a further metabolite that is inert and can be excreted from the body. Thus, the plasma concentrations of one or more metabolites, as well as the drug itself, can be pharmacologically important.

"A pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

Methods of Treatment and Prevention of Hepatitis C Viral Infections

The present invention provides methods for treating or preventing a hepatitis C virus infection in a patient in need thereof.

The present invention further provides methods for introducing a therapeutically effective amount of the Formula I compound or combination of such compounds into the blood stream of a patient in the treatment and/or prevention of hepatitis C viral infections.

The magnitude of a prophylactic or therapeutic dose of a Formula I compound of the invention or a pharmaceutically acceptable salt, solvate, or hydrate, thereof in the acute or chronic treatment or prevention of an infection will vary, however, with the nature and severity of the infection, and the route by which the active ingredient is administered. The dose, and in some cases the dose frequency, will also vary according to the infection to be treated, the age, body weight, and response of the individual patient. Suitable dosing regimens can be readily selected by those skilled in the art with due consideration of such factors.

The methods of the present invention are particularly well suited for human patients. In particular, the methods and doses of the present invention can be useful for immunocompromised patients including, but not limited to cancer patients, HIV infected patients, and patients with an immunodegenerative disease. Furthermore, the methods can be useful for immunocompromised patients currently in a state of remission. The methods and doses of the present invention are also useful for patients undergoing other antiviral treatments. The prevention methods of the present invention are particularly useful for patients at risk of viral infection. These patients include, but are not limited to health care workers, e.g., doctors, nurses, hospice care givers; military personnel; teachers; childcare workers; patients traveling to, or living in, foreign locales, in particular third world locales including social aid workers, missionaries, and foreign diplomats. Finally, the methods and compositions include the treatment of refractory patients or patients resistant to treatment such as resistance to reverse transcriptase inhibitors, protease inhibitors, etc.

Doses

Toxicity and efficacy of the compounds of the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

The data obtained from the cell culture assays and animal studies can be used in formulating a range of dosage of the compounds for use in humans. The dosage of such compounds lie preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture; alternatively, the dose of the Formula I compound may be formulated in animal models to achieve a circulating plasma concentration range of the compound that corresponds to the concentration required to achieve a fixed magnitude of response. Such information can be used to more accurately determine useful doses in humans. Levels in plasma may be measured, for example, by high performance liquid chromatography.

The protocols and compositions of the invention are preferably tested in vitro, and then in vivo, for the desired therapeutic or prophylactic activity, prior to use in humans. For example, in vitro assays which can be used to determine whether administration of a specific therapeutic protocol is indicated, include in vitro cell culture assays in which cells that are responsive to the effects of the Formula I compounds are exposed to the ligand and the magnitude of response is measured by an appropriate technique. The assessment of the Formula I compound is then evaluated with respect to the Formula I compound potency, and the degree of conversion of the Formula I compound prodrug. Compounds for use in methods of the invention can be tested in suitable animal model systems prior to testing in humans, including but not limited to in rats, mice, chicken, cows, monkeys, rabbits, hamsters, etc. The compounds can then be used in the appropriate clinical trials.

The magnitude of a prophylactic or therapeutic dose of a prodrug of a Formula I compound of the invention or a pharmaceutically acceptable salt, solvate, or hydrate thereof in the acute or chronic treatment or prevention of an infection or condition will vary with the nature and severity of the infection, and the route by which the active ingredient is administered. The dose, and perhaps the dose frequency, will also vary according to the infection to be treated, the age, body weight, and response of the individual patient. Suitable dosing regimens can be readily selected by those skilled in the art with due consideration of such factors. In one embodiment, the dose administered depends upon the specific compound to be used, and the weight and condition of the patient. Also, the dose may differ for various particular Formula I compounds; suitable doses can be predicted on the basis of the aforementioned in vitro measurements, in particular by use of such measurements of isatoribine (1) to which the Formula I compound is related, and on the basis of animal studies, such that smaller doses will be suitable for those Formula I compounds that show effectiveness at lower concentrations than other Formula I compounds when measured in the systems described or referenced herein. In general, the dose per day is in the range of from about 0.001 to 100 mg/kg, preferably about 1 to 25 mg/kg, more preferably about 5 to 15 mg/kg. For treatment of humans infected by hepatitis C viruses, about 0.1 mg to about 15 g per day is administered in about one to four divisions a day, preferably 100 mg to 12 g per day, more preferably from 100 mg to 8000 mg per day.

In a preferred embodiment for compounds such as prodrugs of 3-β-D-ribofuralanosythiazolo [4,5-d]pyrimidines from 200 mg to 8000 mg per day is administered in about one to four divisions a day. Additionally, the recommended daily dose ran can be administered in cycles as single agents or in combination with other therapeutic agents. In one embodiment, the daily dose is administered in a single dose or in equally divided doses. In a related embodiment, the recommended daily dose can be administered once time per week, two times per week, three times per week, four times per week or five times per week.

In a preferred embodiment, the compounds of the invention are administered to provide systemic distribution of the compound within the patient. In a related embodiment, the compounds of the invention are administered to produce a systemic effect in the body.

In a another embodiment the compounds of the invention are administered via oral, mucosal (including sublingual, buccal, rectal, nasal, or vaginal), parenteral (including subcutaneous, intramuscular, bolus injection, intraarterial, or intravenous), transdermal, or topical administration. In a specific embodiment the compounds of the invention are administered via mucosal (including sublingual, buccal, rectal, nasal, or vaginal), parenteral (including subcutaneous, intramuscular, bolus injection, intraarterial, or intravenous), transdermal, or topical administration. In a further specific embodiment, the compounds of the invention are administered via oral administration. In a further specific embodiment, the compounds of the invention are not administered via oral administration.

Different therapeutically effective amounts may be applicable for different infections, as will be readily known by those of ordinary skill in the art. Similarly, amounts sufficient to treat or prevent such infections, but insufficient to cause, or sufficient to reduce, adverse effects associated with conventional therapies are also encompassed by the above described dosage amounts and dose frequency schedules.

Combination Therapy

Specific methods of the invention further comprise the administration of an additional therapeutic agent (i.e., a therapeutic agent other than a compound of the invention). In certain embodiments of the present invention, the compounds of the invention can be used in combination with at least one other therapeutic agent. Therapeutic agents include, but are not limited to antibiotics, antiemetic agents, antidepressants, and antifungal agents, anti-inflammatory agents, antiviral agents, anticancer agents, immunomodulatory agents, β-interferons, alkylating agents, hormones or cytokines. In a preferred embodiment the invention encompasses the administration of an additional therapeutic agent that is HCV specific or demonstrates anti-HCV activity.

The Formula I compounds of the invention can be administered or formulated in combination with antibiotics. For example, they can be formulated with a macrolide (e.g., tobramycin (Tobi®)), a cephalosporin (e.g., cephalexin (Keflex®), cephradine (Velosef®), cefuroxime (Ceftin®), cefprozil (Cefzil®), cefaclor (Ceclor®), cefixime (Suprax®) or cefadroxil (Duricef®)), a clarithromycin (e.g., clarithromycin (Biaxin®)), an erythromycin (e.g., erythromycin (EMycin®)), a penicillin (e.g., penicillin V (V-Cillin K® or Pen Vee K®)) or a quinolone (e.g., ofloxacin (Floxin®), ciprofloxacin (Cipro®) or norfloxacin (Noroxin®)), aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

The Formula I compounds of the invention can also be administered or formulated in combination with an antiemetic agent. Suitable antiemetic agents include, but are not limited to, metoclopromide, domperidone, prochlorperazine, promethazine, chlorpromazine, trimethobenzamide, ondansetron, granisetron, hydroxyzine, acethylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinols, thiethylperazine, thioproperazine, tropisetron, and mixtures thereof.

The Formula I compounds of the invention can be administered or formulated in combination with an antidepressant. Suitable antidepressants include, but are not limited to, binedaline, caroxazone, citalopram, dimethazan, fencamine, indalpine, indeloxazine hydrocholoride, nefopam, nomifensine, oxitriptan, oxypertine, paroxetine, sertraline, thiazesim, trazodone, benmoxine, iproclozide, iproniazid, isocarboxazid, nialamide, octamoxin, phenelzine, cotinine, rolicyprine, rolipram, maprotiline, metralindole, mianserin, mirtazepine, adinazolam, amitriptyline, amitriptylinoxide, amoxapine, butriptyline, clomipramine, demexiptiline, desipramine, dibenzepin, dimetacrine, dothiepin, doxepin, fluacizine, imipramine, imipramine N-oxide, iprindole, lofepramine, melitracen, metapramine, nortriptyline, noxiptilin, opipramol, pizotyline, propizepine, protriptyline, quinupramine, tianeptine, trimipramine, adrafinil, benactyzine, bupropion, butacetin, dioxadrol, duloxetine, etoperidone, febarbamate, femoxetine, fenpentadiol, fluoxetine, fluvoxamine, hematoporphyrin, hypericin, levophacetoperane, medifoxamine, milnacipran, minaprine, moclobemide, nefazodone, oxaflozane, piberaline, prolintane, pyrisuccideanol, ritanserin, roxindole, rubidium chloride, sulpiride, tandospirone, thozalinone, tofenacin, toloxatone, tranylcypromine, L-tryptophan, venlafaxine, viloxazine, and zimeldine.

The Formula I compound s of the invention can be administered or formulated in combination with an antifungal agent. Suitable antifungal agents include but are not limited to amphotericin B, itraconazole, ketoconazole, fluconazole, intrathecal, flucytosine, miconazole, butoconazole, clotrimazole, nystatin, terconazole, tioconazole, ciclopirox, econazole, haloprogrin, naftifine, terbinafine, undecylenate, and griseofuldin.

The Formula I compounds of the invention can be administered or formulated in combination with an anti-inflammatory agent. Useful anti-inflammatory agents include, but are not limited to, non-steroidal anti-inflammatory drugs such as salicylic acid, acetylsalicylic acid, methyl salicylate, diflunisal, salsalate, olsalazine, sulfasalazine, acetaminophen, indomethacin, sulindac, etodolac, mefenamic acid, meclofenamate sodium, tolmetin, ketorolac, dichlofenac, ibuprofen, naproxen, naproxen sodium, fenoprofen, ketoprofen, flurbinprofen, oxaprozin, piroxicam, meloxicam, ampiroxicam, droxicam, pivoxicam, tenoxicam, nabumetome, phenylbutazone, oxyphenbutazone, antipyrine, aminopyrine, apazone and nimesulide; leukotriene antagonists including, but not limited to, zileuton, aurothioglucose, gold sodium thiomalate and auranofin; steroids including, but not limited to, alclometasone dipropionate, amcinonide, beclomethasone dipropionate, betametasone, betamethasone benzoate, betamethasone dipropionate, betamethasone sodium phosphate, betamethasone valerate, clobetasol propionate, clocortolone pivalate, hydrocortisone, hydrocortisone derivatives, desonide, desoximatasone, dexamethasone, flunisolide, flucoxinolide, flurandrenolide, halcinocide, medrysone, methylprednisolone, methprednisolone acetate, methylprednisolone sodium succinate, mometasone furoate, paramethasone acetate, prednisolone, prednisolone acetate, prednisolone sodium phosphate, prednisolone tebuatate, prednisone, triamcinolone, triamcinolone acetonide, triamcinolone diacetate, and triamcinolone hexacetonide; and other anti-inflammatory agents including, but not limited to, methotrexate, colchicine, allopurinol, probenecid, sulfinpyrazone and benzbromarone.

The Formula I compounds of the invention can be administered or formulated in combination with another antiviral agent. Useful antiviral agents include, but are not limited to, protease inhibitors, nucleoside reverse transcriptase inhibitors, non-nucleoside reverse transcriptase inhibitors and nucleoside analogs. The antiviral agents include but are not limited to zidovudine, acyclovir, gangcyclovir, vidarabine, idoxuridine, trifluridine, levovirin, viramidine and ribavirin, as well as foscarnet, amantadine, rimantadine, saquinavir, indinavir, amprenavir, lopinavir, ritonavir, the alpha-interferons; beta-interferons; adefovir, clevadine, entecavir, pleconaril.

The Formula I compound of the invention can be administered or formulated in combination with an immunomodulatory agent. Immunomodulatory agents include, but are not limited to, methothrexate, leflunomide, cyclophosphamide, cyclosporine A, mycophenolate mofetil, rapamycin (sirolimus), mizoribine, deoxyspergualin, brequinar, malononitriloamindes (e.g., leflunamide), T cell receptor modulators, and cytokine receptor modulators, peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules and triple helices), small molecules, organic compounds, and inorganic compounds. Examples of T cell receptor modulators include, but are not limited to, anti-T cell receptor antibodies (e.g., anti-CD4 antibodies (e.g., cM-T412 (Boeringer), IDEC-CE9.1® (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anti-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies, anti-CD11a antibodies (e.g., Xanelim (Genentech)), and anti-B7 antibodies (e.g., IDEC-114 (IDEC)) and CTLA4-immunoglobulin. Examples of cytokine receptor modulators include, but are not limited to, soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (e.g., interleukin (IL)-2, IL-3, IL-4, IL-5, IL-6, IL-7, IL-8, IL-9, IL-10, IL-11, IL-12, IL-15, TNF-α, interferon (IFN)-α, IFN-β, IFN-γ, and GM-CSF), anti-cytokine receptor antibodies (e.g., anti-IFN receptor antibodies, anti-IL-2 receptor antibodies (e.g., Zenapax (Protein Design Labs)), anti-IL-4 receptor antibodies, anti-IL-6 receptor antibodies, anti-IL-10 receptor antibodies, and anti-IL-12 receptor antibodies), anti-cytokine antibodies (e.g., anti-IFN antibodies, anti-TNF-α antibodies, anti-IL-1β antibodies, anti-IL-6 antibodies, anti-IL-8 antibodies (e.g., ABX-IL-8 (Abgenix)), and anti-IL-12 antibodies).

The Formula I compounds of the invention can be administered or formulated in combination with an agent which inhibits viral enzymes, including but not limited to inhibitors of HCV protease, such as BILN 2061 and inhibitors of NS5b polymerase such as NM107 and its prodrug NM283 (Idenix Pharmaceuticals, Inc., Cambridge, Mass.).

The Formula I compounds of the invention can be administered or formulated in combination with an agent which inhibits HCV polymerase such as those described in Wu, *Curr Drug Targets Infect Disord.* 2003; 3(3):207-19 or in combination with compounds that inhibit the helicase function of the virus such as those described in Bretner M, et al *Nucleosides Nucleotides Nucleic Acids.* 2003; 22(5-8):1531, or with inhibitors of other HCV specific targets such as those described in Zhang X. *IDrugs.* 2002; 5(2):154-8.

The Formula I compounds of the invention can be administered or formulated in combination with an agent which inhibits viral replication.

The Formula I compounds of the invention can be administered or formulated in combination with cytokines. Examples of cytokines include, but are not limited to, interleukin-2 (IL-2), interleukin-3 (IL-3), interleukin-4 (IL-4), interleukin-5 (IL-5), interleukin-6 (IL-6), interleukin-7 (IL-7), interleukin-9 (IL-9), interleukin-10 (IL-10), interleukin-12 (IL-12), interleukin 15 (IL-15), interleukin 18 (IL-18), platelet derived growth factor (PDGF), erythropoietin (Epo), epidermal growth factor (EGF), fibroblast growth factor (FGF), granulocyte macrophage stimulating factor (GM-CSF), granulocyte colony stimulating factor (G-CSF), macrophage colony stimulating factor (M-CSF), prolactin, and interferon (IFN), e.g. IFN-alpha, and IFN-gamma).

The Formula I compounds of the invention can be administered or formulated in combination with hormones. Examples of hormones include, but are not limited to, luteinizing hormone releasing hormone (LHRH), growth hormone (GH), growth hormone releasing hormone, ACTH, somatostatin, somatotropin, somatomedin, parathyroid hormone, hypothalamic releasing factors, insulin, glucagon, enkephalins, vasopressin, calcitonin, heparin, low molecular weight heparins, heparinoids, synthetic and natural opioids, insulin thyroid stimulating hormones, and endorphins.

The Formula I compounds of the invention can be administered or formulated in combination with β-interferons which include, but are not limited to, interferon beta-1a, interferon beta-1b.

The Formula I compounds of the invention can be administered or formulated in combination with α-interferons which include, but are not limited to, interferon alpha-1, interferon alpha-2a (roferon), interferon alpha-2b, intron, Peg-Intron, Pegasys, consensus interferon (infergen) and albuferon.

The Formula I compounds of the invention can be administered or formulated in combination with an absorption enhancer, particularly those which target the lymphatic system, including, but not limited to sodium glycocholate; sodium caprate; N-lauryl-ÿ-D-maltopyranoside; EDTA; mixed micelle; and those reported in Muranishi *Crit. Rev. Ther. Drug Carrier Syst.,* 7-1-33, which is hereby incorporated by reference in its entirety. Other known absorption enhancers can also be used. Thus, the invention also encompasses a pharmaceutical composition comprising one or more Formula I compounds of the invention and one or more absorption enhancers.

The Formula I compounds of the invention can be administered or formulated in combination with an alkylating agent. Examples of alkylating agents include, but are not limited to nitrogen mustards, ethylenimines, methylmelamines, alkyl sulfonates, nitrosoureas, triazenes, mechlorethamine, cyclophosphamide, ifosfamide, melphalan, chlorambucil, hexamethylmelaine, thiotepa, busulfan, carmustine, streptozocin, dacarbazine and temozolomide.

The compounds of the invention and the other therapeutics agent can act additively or, more preferably, synergistically. In a preferred embodiment, a composition comprising a compound of the invention is administered concurrently with the administration of another therapeutic agent, which can be part of the same composition or in a different composition from that comprising the compounds of the invention. In another embodiment, a compound of the invention is administered prior to or subsequent to administration of another therapeutic agent. In a separate embodiment, a compound of the invention is administered to a patient who has not previously undergone or is not currently undergoing treatment with another therapeutic agent, particularly an antiviral agent.

In one embodiment, the methods of the invention comprise the administration of one or more Formula I compounds of the invention without an additional therapeutic agent.

Pharmaceutical Compositions and Dosage Forms

Pharmaceutical compositions and single unit dosage forms comprising a Formula I compound of the invention, or a pharmaceutically acceptable salt, or hydrate thereof, are also encompassed by the invention. Individual dosage forms of the invention may be suitable for oral, mucosal (including sublingual, buccal, rectal, nasal, or vaginal), parenteral (including subcutaneous, intramuscular, bolus injection, intraarterial, or intravenous), transdermal, or topical administration. Pharmaceutical compositions and dosage forms of the invention typically also comprise one or more pharmaceutically acceptable excipients. Sterile dosage forms are also contemplated.

In an alternative embodiment, pharmaceutical composition encompassed by this embodiment includes a Formula I compound of the invention, or a pharmaceutically acceptable salt, or hydrate thereof, and at least one additional therapeutic agent. Examples of additional therapeutic agents include, but are not limited to, those listed above in section 5.2.2.

The composition, shape, and type of dosage forms of the invention will typically vary depending on their use. For example, a dosage form used in the acute treatment of a disease or a related disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease or disorder. These and other ways in which specific dosage forms encompassed by this invention will vary from one another will be readily apparent to those skilled in the art. See, e.g., *Remington's Pharmaceutical Sciences,* 18th ed., Mack Publishing, Easton Pa. (1990). Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g. crystalline or amorphous solids) that can be reconstituted to provide liquid dosage forms suitable for parenteral administration to a patient.

Typical pharmaceutical compositions and dosage forms comprise one or more carriers, excipients or diluents. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, N.Y., N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms of the invention comprise Formula I compounds of the invention, or a pharmaceutically acceptable salt or hydrate thereof comprise 0.1 mg to 1500 mg per unit to provide doses of about 0.01 to 200 mg/kg per day.

Oral Dosage Forms

Pharmaceutical compositions of the invention that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

Typical oral dosage forms of the invention are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent. Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients of the invention can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry and/or lyophylized products ready to be dissolved or suspended in a pharmaceutically acceptable vehicle for injection (reconstitutable powders), suspensions ready for injection, and emulsions.

Suitable vehicles that can be used to provide parenteral dosage forms of the invention are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. Compounds that increase the solubility of one or more of the active ingredients disclosed herein can also be incorporated into the parenteral dosage forms of the invention.

Transdermal Dosage Forms

Transdermal dosage forms include "reservoir type" or "matrix type" patches, which can be applied to the skin and worn for a specific period of time to permit the penetration of a desired amount of active ingredients.

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof. Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Topical Dosage Forms

Topical dosage forms of the invention include, but are not limited to, creams, lotions, ointments, gels, solutions, emulsions, suspensions, or other forms known to one of skill in the art. See, e.g. *Remington's Pharmaceutical Sciences,* 18th eds., Mack Publishing, Easton Pa. (1990); and *Introduction to Pharmaceutical Dosage Forms,* 4th ed., Lea & Febiger, Philadelphia (1985).

Suitable excipients (e.g., carriers and diluents) and other materials that can be used to provide transdermal and topical dosage forms encompassed by this invention are well known to those skilled in the pharmaceutical arts, and depend on the particular tissue to which a given pharmaceutical composition or dosage form will be applied. With that fact in mind, typical excipients include, but are not limited to, water, acetone, ethanol, ethylene glycol, propylene glycol, butane-1,3-diol, isopropyl myristate, isopropyl palmitate, mineral oil, and mixtures thereof.

Depending on the specific tissue to be treated, additional components may be used prior to, in conjunction with, or subsequent to treatment with active ingredients of the invention. For example, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as Tween 80 (polysorbate 80) and Span 60 (sorbitan monostearate).

Mucosal Dosage Forms

Mucosal dosage forms of the invention include, but are not limited to, ophthalmic solutions, sprays and aerosols, or other forms known to one of skill in the art. See, e.g. *Remington's Pharmaceutical Sciences,* 18th eds., Mack Publishing, Easton Pa. (1990); and *Introduction to Pharmaceutical Dosage Forms,* 4th ed., Lea & Febiger, Philadelphia (1985). Dosage forms suitable for treating mucosal tissues within the oral cavity can be formulated as mouthwashes or as oral gels. In one embodiment, the aerosol comprises a carrier. In another embodiment, the aerosol is carrier free.

The Formula I compounds of the invention may also be administered directly to the lung by inhalation. For administration by inhalation, a Formula I compound can be conveniently delivered to the lung by a number of different devices. For example, a Metered Dose Inhaler ("MDI") which utilizes canisters that contain a suitable low boiling propellant, e.g., dichlorodifluoromethane, trichlorofluoromethane, dichlorotetrafluoroethane, carbon dioxide or other suitable gas can be used to deliver a Formula I compound directly to the lung. MDI devices are available from a number of suppliers such as 3M Corporation, Aventis, Boehringer Ingleheim, Forest Laboratories, Glaxo-Wellcome, Schering Plough and Vectura.

Alternatively, a Dry Powder Inhaler (DPI) device can be used to administer a Formula I compound to the lung (see, e.g., Raleigh et al., *Proc. Amer. Assoc. Cancer Research Annual Meeting,* 1999, 40, 397, which is herein incorporated by reference). DPI devices typically use a mechanism such as a burst of gas to create a cloud of dry powder inside a container, which can then be inhaled by the patient. DPI devices are also well known in the art and can be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator can be formulated containing a powder mix of the compound and a suitable powder base such as lactose or starch for these systems.

Another type of device that can be used to deliver a Formula I compound to the lung is a liquid spray device supplied, for example, by Aradigm Corporation. Liquid spray systems use extremely small nozzle holes to aerosolize liquid drug formulations that can then be directly inhaled into the lung.

In a preferred embodiment, a nebulizer device is used to deliver a Formula I compound to the lung. Nebulizers create aerosols from liquid drug formulations by using, for example, ultrasonic energy to form fine particles that can be readily inhaled (See e.g. Verschoyle et al., *British J. Cancer,* 1999, 80, Suppl 2, 96, which is herein incorporated by reference). Examples of nebulizers include devices supplied by Sheffield/Systemic Pulmonary Delivery Ltd. (See, Armer et al., U.S. Pat. No. 5,954,047; van der Linden et al., U.S. Pat. No. 5,950,619; van der Linden et al., U.S. Pat. No. 5,970,974, which are herein incorporated by reference), Aventis and Batelle Pulmonary Therapeutics.

In a particularly preferred embodiment, an electrohydrodynamic ("EHD") aerosol device is used to deliver Formula I compounds to the lung. EHD aerosol devices use electrical energy to aerosolize liquid drug solutions or suspensions (see, e.g. Noakes et al., U.S. Pat. No. 4,765,539; Coffee, U.S. Pat. No. 4,962,885; Coffee, PCT Application, WO 94/12285; Coffee, PCT Application, WO 94/14543; Coffee, PCT Application, WO 95/26234, Coffee, PCT Application, WO 95/26235, Coffee, PCT Application, WO 95/32807, which are herein incorporated by reference). The electrochemical properties of the Formula I compounds formulation may be important parameters to optimize when delivering this drug to the lung with an EHD aerosol device and such optimization is routinely performed by one of skill in the art. EHD aerosol devices may more efficiently delivery drugs to the lung than existing pulmonary delivery technologies. Other methods of intra-pulmonary delivery of Formula I compounds will be known to the skilled artisan and are within the scope of the invention.

Liquid drug formulations suitable for use with nebulizers and liquid spray devices and EHD aerosol devices will typically include a Formula I compound with a pharmaceutically acceptable carrier. Preferably, the pharmaceutically acceptable carrier is a liquid such as alcohol, water, polyethylene glycol or a perfluorocarbon. Optionally, another material may be added to alter the aerosol properties of the solution or suspension of the Formula I compound. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. Nos. 5,112,598; Biesalski, 5,556,611, which are herein incorporated by reference) A Formula I compound can also be formulated in rectal or vaginal compositions such as suppositories or retention enemas, e.g., containing conventional suppository bases such as cocoa butter or other glycerides.

In addition to the formulations described previously, a Formula I compound can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example, as an emulsion in an acceptable oil) or ion exchange resins, or as sparingly soluble derivatives, for example, as a sparingly soluble salt.

Alternatively, other pharmaceutical delivery systems can be employed. Liposomes and emulsions are well known examples of delivery vehicles that can be used to deliver Formula I compounds. Certain organic solvents such as dimethylsulfoxide can also be employed, although usually at the cost of greater toxicity. A Formula I compound can also be delivered in a controlled release system. In one embodiment, a pump can be used (Sefton, *CRC Crit. Ref Biomed Eng.,* 1987, 14, 201; Buchwald et al., *Surgery,* 1980, 88, 507; Saudek et al., *N. Engl. J. Med.,* 1989, 321, 574). In another embodiment, polymeric materials can be used (see *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Ranger and Peppas, *J. Macromol. Sci. Rev. Macromol. Chem.,* 1983, 23, 61; see also Levy et al., *Science,* 1985, 228, 190; During et al., *Ann. Neurol.,* 1989, 25, 351; Howard et al., 1989, *J. Neurosurg.* 71, 105). In yet another embodiment, a controlled-release system can be placed in proximity of the target of the compounds of the invention, e.g. the lung, thus requiring only a fraction of the systemic dose (see, e.g., Goodson, in *Medical Applications of Controlled Release*, supra, vol. 2, pp. 115 (1984)). Other controlled-release system can be used (see, e.g. Langer, *Science,* 1990, 249, 1527).

Suitable excipients (e.g., carriers and diluents) and other materials that can be used to provide mucosal dosage forms encompassed by this invention are well known to those skilled in the pharmaceutical arts, and depend on the particular site or method which a given pharmaceutical composition or dosage form will be administered. With that fact in mind, typical excipients include, but are not limited to, water, ethanol, ethylene glycol, propylene glycol, butane-1,3-diol, isopropyl myristate, isopropyl palmitate, mineral oil, and mixtures thereof, which are non-toxic and pharmaceutically acceptable. Examples of such additional ingredients are well known in the art. See, e.g., *Remington's Pharmaceutical Sciences,* 18th eds., Mack Publishing, Easton Pa. (1990).

The pH of a pharmaceutical composition or dosage form, or of the tissue to which the pharmaceutical composition or dosage form is applied, can also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery-enhancing or penetration-enhancing agent. Different salts, hydrates or solvates of the active ingredients can be used to further adjust the properties of the resulting composition.

Kits

The invention provides a pharmaceutical pack or kit comprising one or more containers comprising a Formula I compound useful for the treatment or prevention of a Hepatitis C virus infection. In other embodiments, the invention provides a pharmaceutical pack or kit comprising one or more containers comprising a Formula I compound useful for the treatment or prevention of a Hepatitis C virus infection and one or more containers comprising an additional therapeutic agent, including but not limited to those listed in section 5.2.2 above, in particular an antiviral agent, an interferon, an agent which inhibits viral enzymes, or an agent which inhibits viral replication, preferably the additional therapeutic agent is HCV specific or demonstrates anti-HCV activity.

The invention also provides a pharmaceutical pack or kit comprising one or more containers comprising one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The inventive agents may be prepared using the reaction routes and synthesis schemes as described below, employing the general techniques known in the art using starting materials that are readily available. The synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or generally known in the art will be recognized as having applicability for preparing other compounds of the invention.

Preparation of Compounds

In the synthetic schemes described below, unless otherwise indicated all temperatures are set forth in degrees Celsius and all parts and percentages are by weight. Reagents were purchased from commercial suppliers such as Aldrich Chemical Company or Lancaster Synthesis Ltd. and were used without further purification unless otherwise indicated. Tetrahydrofuran (THF) and N,N-dimethylforamide (DMF) were purchased from Aldrich in Sure Seal bottles and used as received. Unless otherwise indicated, the following solvents and reagents were distilled under a blanket of dry nitrogen. THF, and $Et_2O$ were distilled from Na-benzophenone ketyl; $CH_2Cl_2$, diisopropylamine, pyridine and $Et_3N$ were distilled from $CaH_2$; MeCN was distilled first from $P_2O_5$, then from $CaH_2$; MeOH was distilled from Mg; PhMe, EtOAc and i-PrOAc were distilled from $CaH_2$; TFAA was purified via simple atmospheric distillation under dry argon.

The reactions set forth below were done generally under a positive pressure of argon at an ambient temperature (unless otherwise stated) in anhydrous solvents, and the reaction flasks were fitted with rubber septa for the introduction of substrates and reagents via syringe. Glassware was oven dried and/or heat dried. The reactions were assayed by TLC and terminated as judged by the consumption of starting material.

Analytical thin layer chromatography (TLC) was performed on aluminum-backed silica gel 60 $F_{254}$ 0.2 mm plates (EM Science), and visualized with UV light (254 nm) followed by heating with commercial ethanolic phosphomolybdic acid. Preparative thin layer chromatography (TLC) was performed on aluminum-backed silica gel 60 $F_{254}$ 1.0 mm plates (EM Science) and visualized with UV light (254 nm).

Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ and/or $Mg_2SO_4$ prior to filtration and evaporation of the solvents under reduced pressure on a rotary evaporator and noted as solvents removed in vacuo. Column chromatography was completed under positive pressure using 230-400 mesh silica gel or 50-200 mesh neutral alumina. Hydrogenolysis was done at the pressure indicated in the examples or at ambient pressure.

$^1$H-NMR spectra were recorded on a Varian Mercury-VX400 instrument operating at 400 MHz and $^{13}$C-NMR spectra were recorded operating at 75 MHz. NMR spectra were obtained as $CDCl_3$ solutions (reported in ppm), using chloroform as the reference standard (7.27 ppm and 77.00 ppm), $CD_3OD$ (3.4 and 4.8 ppm and 49.3 ppm), DMSO-$d_6$, or internally tetramethylsilane (0.00 ppm) when appropriate. Other NMR solvents were used as needed. When peak multiplicities are reported, the following abbreviations are used: s (singlet), d (doublet), t (triplet), q (quartet), m (multiplet), br (broadened), dd (doublet of doublets), dt (doublet of triplets). Coupling constants, when given, are reported in Hertz (Hz).

Infrared (IR) spectra were recorded on a FT-IR Spectrometer as neat oils, as KBr pellets, or as $CDCl_3$ solutions, and when given are reported in wave numbers ($cm^{-1}$). Mass spectra reported are (+)-ES LC/MS conducted by the Analytical Chemistry Department of Anadys Pharmaceuticals, Inc. Elemental analyses were conducted by the Atlantic Microlab, Inc. in Norcross, Ga. Melting points (mp) were determined on an open capillary apparatus, and are uncorrected.

The described synthetic pathways and experimental procedures utilize many common chemical abbreviations, THF (tetrahydrofuran), DMF (N,N-dimethylformamide), EtOAc (ethyl acetate), DMSO (di-methyl sulfoxide), DMAP (4-dimethylaminopyridine), DBU (1,8-diazacyclo[5.4.0]undec-7-ene), DCM (4-(dicyanomethylene)-2-methyl-6-(4-dimethylamino-styryl)-4H-pyran), MCPBA (3-chloroperoxybenzoic acid), EDC (1-(3-dimethylaminopropyl)-3-ethylcarbodiimide hydrochloride), HATU (O-(7-azabenzotriazol-1-yl)-1,1,3,3-tetramethyluronium hexafluorophosphate), HOBT (1-hydroxybenzotriazole hydrate), TFAA (trifluoroacetic anhydride), pyBOP (benzotriazol-1-yloxy)tripyrrolidinophosphonium hexafluorophosphate), DIEA (diisopropylethylamine), BOC (tert-butoxycarbonyl), 2,2-DMP (2,2-dimethoxypropane), IPA (isopropyl alcohol), TEA (triethylamine), DCE (1,2-dichloroethane), PPTS (pyridinium p-toluenesulfonate), DEAD (diethylazodicarboxylate), PS (polymer supported), HF (hydrogen fluoride), MeCN (acetonitrile), MeOH (methanol), Val (valine), Phe (phenyl alanine), HPLC (high pressure liquid chromatography), TLC (thin layer chromatography), and the like.

Scheme 1 shows a general procedure to prepare the 5'-amino acid esters of 5-amino-3-β-D-ribofuranosylthiazolo[4,5-d]pyrimidine-2,7-dione.

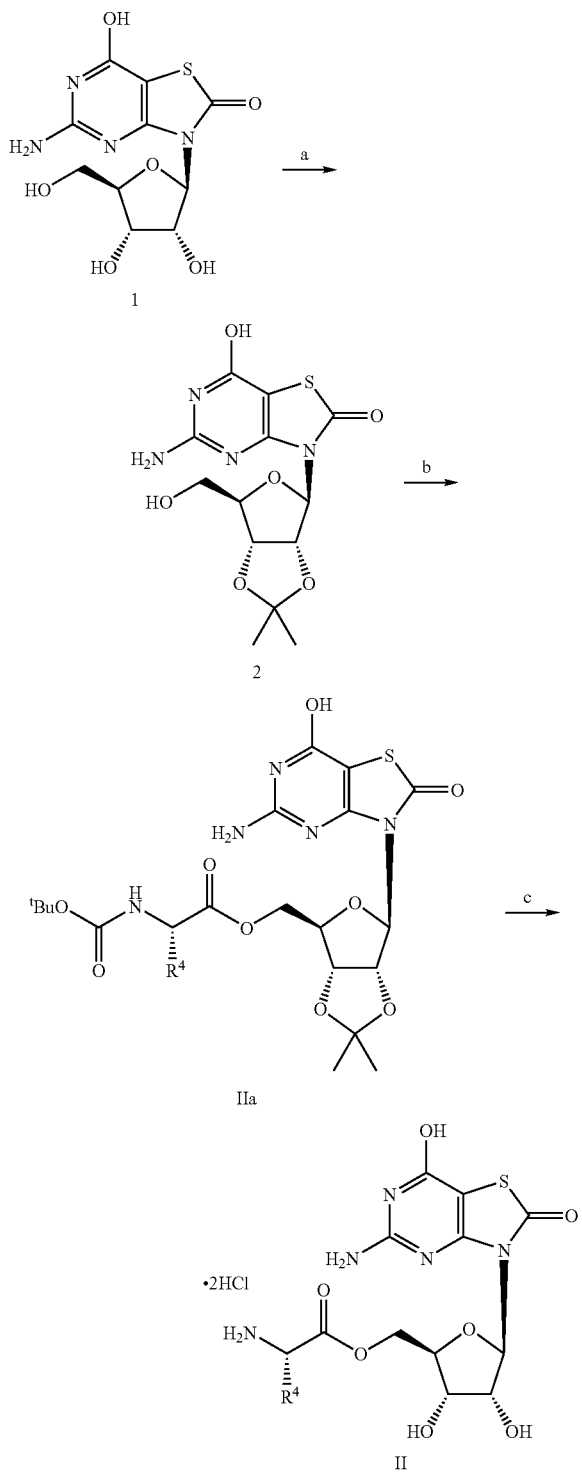

a) 2,2-dimethoxypropane, acetone, DMSO, $MeSO_3H$, 0° C.
b) BOC — $NHCHR^4CO_2H$, EDC, DMAP, PhMe, 0° C. -r.t.
c) anh.HCl, iPrOAc, iPrOH In a typical synthetic route, the 2',3'-hydroxyl groups of the β-D-ribose moiety of 5-amino-3-β-D-ribofuranosylthiazolo[4,5-d]pyrimidine-2,7-dione is first protected, preferably with an acetonide as shown in 2. The free 5'-hydroxyl can then be subjected to a variety of esterification methods with a N-protected amino acid to form IIa. The nitrogen of the amino acid ester and the 2',3'-hydroxyls of the ribose unit are then subjected to various deprotection conditions, preferably concurrently, followed by salt formation of the free amine of the amino acid ester as illustrated for II.

EXAMPLE 1

5-Amino-3-(5'-O-L-valinyl-β-D-ribofuranosyl)thiazolo[4,5-d]pyrimidine-2,7-dione Dihydrochloride (3)

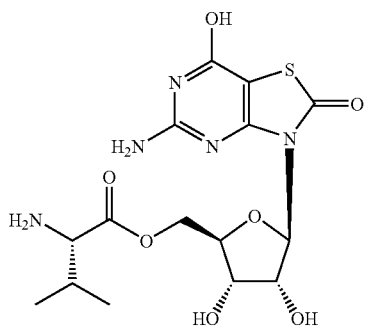

Step 1: Preparation of 5-Amino-3-(2',3'-O-isopropylidene-β-D-ribofuranosyl) thiazolo[4,5-d]pyrimidine-2,7-dione To a heterogeneous mixture of 1 (5.37 g, 17.0 mmol, prepared according to the procedure given in U.S. Pat. No. 5,041,426 (Example 2), which is incorporated by reference in its entirety) in acetone (40 mL) contained in a 250 mL Morton flask was added successively 2,2-DMP (6.26 mL, 50.9 mmol), DMSO (6.6 mL), and MeSO$_3$H (220 µL, 3.39 mmol) at room temperature. The reaction mixture was stirred vigorously, becoming homogeneous and golden yellow as the diol was consumed. TLC analysis (SiO$_2$, 10% MeOH—CHCl$_3$) indicated reaction completion after 6 h. Undissolved solids were removed via gravity filtration using fluted Whatman type 1 filter paper. This was followed by pouring of the filtrate into 10 volumes of ice water (~400 mL), resulting in immediate precipitation of a white solid. After a brief period of stirring, NaHCO$_3$ (285 mg, 3.39 mmol) dissolved in water (10 mL) was added to neutralize the MeSO$_3$H. Vigorous stirring in the Morton reactor was continued for 15 min, whereupon the mixture was filtered through a coarse scintered glass funnel. The solid material was washed with ice water (100 mL), air dried, then dried further under high vacuum at 65° C., affording 5.36 g (88%) of the acetonide 2 as a white solid: mp 280-81° C.; $^1$H (DMSO-d$_6$) δ 1.28 (s, 3H), 1.47 (s, 3H), 3.43-3.55 (m, 2H), 3.95-3.99 (m, 1H), 4.77-4.80 (m, 1H), 4.88-4.91 (m, 1H), 5.24-5.26 (m, 1H), 5.99 (s, 1H), 6.97 (br s, 2H), 11.25 (s, 1H).

Step 2: Preparation of 5-Amino-3-(2',3'-O-isopropylidene-5'-N-tert-butoxycarbonyl-L-valinyl)-β-D-ribofuranosyl)-thiazolo[4,5-d]pyrimidine-2,7-dione (4)

To a solution of N-butoxycarbonyl-(L)-valine (671 mg, 2.81 mmol) in THF (9 mL) at 0° C. was added EDC (588 mg, 3.07 mmol). The resultant homogeneous mixture was stirred 45 min at 0° C., at which point it had become heterogeneous, and solid acetonide 2 from Step 1 above (1.00 g, 2.81 mmol) was added as one portion. Subsequently added was solid DMAP (522 mg, 4.27 mmol). The reaction mixture was permitted to reach room temperature, and stirred an additional 5 h, whereupon it was concentrated at 25° C. via rotary evaporation to a yellow syrup. The residue was dissolved in EtOAc (50 mL), partitioned with 1 N HCl (10 mL) followed by neutralization of acid with saturated aqueous NaHCO$_3$ (10 mL). The acidic aqueous phase was further extracted with EtOAc (2×50 mL), and then partitioned with the basic aqueous phase. The combined organic phases were dried over Na$_2$SO$_4$, filtered through a short pad of SiO$_2$, and concentrated, affording 1.480 g (96%) of Boc-protected amino acid ester 4 as a foam: mp 158° C. (dec); $^1$H (CDCl$_3$) δ 0.86 (d, J=7.0, 3H), 0.95 (d, J=7.0, 3H), 1.35 (s, 3H), 1.44 (s, 9H), 1.56 (s, 3H), 1.75 (br s, 1H), 2.08-2.19 (m, 1H), 4.20-4.24 (m, 2H), 4.30-4.37 (m, 1H), 4.56 (dd, J=11.0, 5.9, 1H), 4.96 (dd, J=6.2, 3.7, 1H), 5.11 (br d, J=8.8, 1H), 5.29 (br d, J=6.6, 1H), 5.88 (br s, 2H), 6.23 (s, 1H).

Step 3: Preparation of 5-Amino-3-(5'-O-L-valinyl-β-D-ribofuranosyl)thiazolo[4,5-d]pyrimidine-2,7-dione Dihydrochloride (3)

A stream of HCl gas was passed through a bubbler of concentrated H$_2$SO$_4$, and subsequently directed (via fritted dispersion tube) into a 250 mL 3-neck Morton flask containing dry isopropyl acetate (80 mL) at 0° C. until a saturated solution was obtained. To this was added a solution of the Boc-amino acid ester from Step 2 above (5.53 g, 9.95 mmol) in isopropyl acetate (30 mL), resulting in the formation of a white solid precipitate within 5 min. To this was added 10% (v/v) IPA (11 mL). The reaction mixture was warmed to room temperature, then stirred 12 h. The heterogeneous reaction mixture was diluted with dry toluene (100 mL). Filtration using a medium pore scintered glass funnel under N$_2$ provided an off-white, amorphous solid. Trituration of the solid in dry THF was followed by filtration and vacuum drying at 65° C., affording 3.677 g (81%) of the title compound 3 as a white solid: mp 166-68° C. (dec); $^1$H (DMSO-d$_6$) δ 0.90 (d, J=7.0, 3H), 0.94 (d, J=7.0, 3H), 2.14-2.18 (m, 1H), 3.83-3.85 (m, 1H), 3.96-4.00 (m, 1H), 4.23-4.28 (m, 2H), 4.42 (dd, J=11.7, 3.4, 1H), 4.75 (dd, J=10.3, 5.5, 1H), 5.81 (d, J=4.4, 1H), 6.46 (br s, 3H), 7.23 (br s, 2H), 8.47 (s, 3H), 11.5 (br s, 1H).

Elemental analysis for C$_{15}$H$_{21}$N$_5$O$_7$S.2HCl: calc'd: C, 36.89; H, 4.75; Cl, 14.52; N, 14.34; S, 6.57; found: C, 37.03: H, 4.74; Cl, 14.26; N, 14.24; S, 6.42.

EXAMPLE 2

5-Amino-3-(5'-O-L-isoleucyl-β-D-ribofuranosyl)thiazolo[4,5-d]pyrimidine-2,7-dione 3/2 Hydrochloride (5)

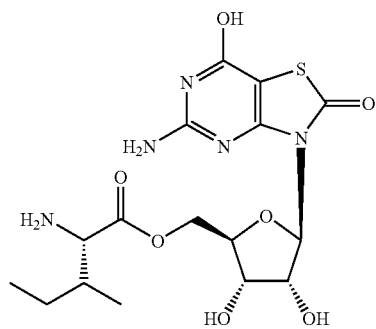

Step 1: Preparation of 5-Amino-3-(2',3'-O-isopropylidene-5'-N-tert butoxycarbonyl-L-isoleucyl)-β-D-ribofuranosyl)-thiazolo[4,5-d]pyrimidinine-2,7-dione (6)

In a manner similar to step 2 of Example 1,5-Amino-3-(2',3'-O-isopropylidene-5'-N-tert-butoxycarbonyl-L-isoleucyl)-β-D-ribofuranosyl)-thiazolo[4,5-d]pyrimidine-2,7-dione 6 was prepared in a yield of 93% from 5-Amino-3-(2',3'-O-isopropylidene-β-D-ribofuranosyl)-thiazolo[4,5-d]pyrimidine-2,7-dione 2 and N-tert-butoxy-L-isoleucine 7 as an off-white foam: $^1$H NMR (400 MHz, $d_6$-DMSO) δ 11.29 (s, 1H), 7.09 (d, J=8.0, 1H), 7.02 (br s, 1H), 6.02 (s, 1H), 5.28 (d, J=6.2, 1H), 5.06 (br s, 1H), 4.16-4.22 (m, 2H), 3.85 (dd, J=8.0, 6.6, 1H), 1.68 (br s, 1H), 1.47 (s, 3H), 1.34 (s, 9H), 1.29 (s, 3H), 0.71-0.89 (m, 5H).

Step 2: Preparation of 5-Amino-3-(5'-O-L-isoleucyl-β-D-ribofuranosyl)thiazolo-[4,5-d]pyrimidine-2,7-dione Dihydrochloride (5)

In a manner similar to Step 3 of Example 2 was prepared the title compound as a white solid from the above intermediate in an 80% yield: mp 173-174° C. (dec); $^1$H NMR (400 MHz, $d_6$-DMSO) δ 11.41 (br s, 1H), 8.41 (br s, 3H), 7.15 (br s, 2H), 5.82 (d, J=4.8, 1H), 4.50-5.00 (m, 2H), 4.40 (dd, J=11.7, 3.3, 1H), 4.21-4.30 (m, 2H), 3.91-4.0 (m, 2H), 1.84-1.91 (m, 1H), 1.37-1.44 (m, 1H), 1.19-1.27 (m, 1H), 0.80-0.87 (m, 6H). Elemental analysis for $C_{16}H_{23}N_5O_7S·3/2HCl$: calc'd: C, 39.69; H, 5.10; N, 14.47; Cl, 10.98; S, 6.62; found: C, 39.05; H, 5.13; N, 13.73; Cl, 11.08; S, 6.02.

EXAMPLE 3

5-Amino-3-(5'O-[α-L-tert-butylglycinyl]-β-D-ribofuranosyl)thiazolo [4,5-d]pyrimidine-2,7-dione Hydrochloride (8)

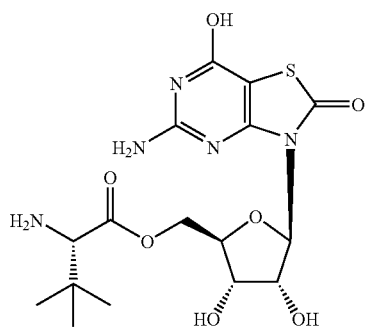

Step 1: Preparation of 5-Amino-3-(2',3'-O-isopropylidene-5'-N-tert-butoxy-carbonyl-[α-L-tert-butylglycyl]-β-D-ribofuranosyl)-thiazolo[4,5-d]pyrimidine-2, 7-dione (9)

In a manner similar to Step 2 of Example 1,5-Amino-3-(2',3'-O-isopropylidene-5'-N-tert-butoxycarbonyl-[α-L-tert-butylglycinyl]-β-D-ribofuranosyl)-thiazolo[4,5-d]pyrimidine-2,7-dione 10 was prepared in a yield of 66% from 5-Amino-3-(2,3-O-isopropylidene-β-D-ribofuranosyl)-thiazolo[4,5-d]pyrimidinone-2,7-dione 2 and N-α-L-tert-butoxyglycine as an off-white foam: $^1$H NMR (400 MHz, $d_6$-DMSO) δ 11.28 (br s, 1H), 6.70-7.40 (m, 3H), 6.02 (s, 1H), 5.30 (d, J=6.2, 1H), 5.05 (br s, 1H), 4.17-4.24 (m, 3H), 3.77 (d, J=8.4, 1H), 1.47 (s, 3H), 1.33 (s, 9H), 1.29 (s, 3H), 0.85 (s, 9H).

Step 2: Preparation of 5-Amino-3-(5'-O-[α-L-tert-butylglycyl]-β-D-ribofuranosyl)-thiazolo[4,5-d]pyrimidine-2,7-dione (8)

In a manner similar to Step 3 of Example 1 was prepared the title compound 8 as a white solid from the above intermediate in an 80% yield: mp 202-203° C. (dec); $^1$H NMR (400 MHz, $d_6$-DMSO) δ 11.35 (br s, 1H), 8.31 (br s, 3H), 7.08 (br s, 2H), 5.83 (d, J=4.0, 1H), 5.45 (br s, 1H), 5.21 (br s, 1H), 4.77-4.82 (m, 1H), 4.42 (dd, J=11.4, 2.6, 1H), 4.23-4.28 (m, 1H), 3.96-4.04 (m, 1H), 3.74 (s, 1H), 0.97 (s, 9H). Elemental analysis for $C_{16}H_{23}N_5O_7S·HCl$: calc'd: C, 41.25; H, 5.19; N, 15.03; Cl, 7.61; S, 6.88; found: C, 40.41; H, 5.41; N, 14.16; Cl, 7.01; S, 6.23.

EXAMPLE 4

5-Amino-3-(5'-O-[α-L-N-methylvalinyl]-β-D-ribofuranosyl)thiazolo[4,5-d]pyrimidine-2,7-dione Hydrochloride (11)

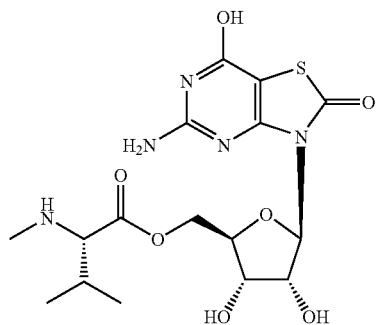

Step 1: Preparation of 5-Amino-3-(2',3'-O-isopropylidene-5'-N-tert-butoxycarbonyl-[α-L-N-methylvalinyl]-β-D-ribofuranosyl)-thiazolo[4, 5-d]pyrimidine-2,7-dione (12)

In a manner similar to Step 2 of Example 1,5-Amino-3-(2',3'-O-isopropylidene-5'-N-tert-butoxycarbonyl-[α-L-N-methylvalinyl]-β-D-ribofuranosyl)-thiazolo[4,5-d]pyrimidine-2,7-dione 12 was prepared in a yield of 63% from 5-Amino-3-(2',3'-O-isopropylidene-β-D-ribofuranosyl)-thiazolo[4,5-d]pyrimidine-2,7-dione 2 and N-tert-butoxy-L-N-methylvaline 13 as an off-white foam: $^1$H NMR (400 MHz, $d_6$-DMSO) rotameric carbamate δ 11.28 (br s, 1H), 7.00 (br s, 2H), 6.02 (s, 1H), 5.27 (d, J=6.6, 1H), 5.04 (br s, 1H), 4.14-4.28 (m, 3H), 3.91 (d, J=9.5, 1H), 2.79 (br s, 3H), 2.09 (br s, 1H), 1.46 (s, 3H), 1.36 (s, 4.5H), 1.32 (s, 4.5H), 1.28 (s, 3H), 0.78-0.89 (m, 6H).

Step 2: 5-Amino-3-(5'-O-[α-L-N-methylvalinyl]-β-D-ribofuranosyl)thiazolo[4, 5-d]pyrimidine-2,7-dione hydrochloride (11)

In a manner similar to Step 3 of Example 1 was prepared the title compound 11 as a slightly impure white solid from the above intermediate in an 60% yield: mp >180° C. (dec);

$^1$H NMR (400 MHz, d$_6$-DMSO) δ 11.31 (br s, 1H), 9.05 (br s, 2H), 7.05 (br s, 2H), 5.83 (d, J=4.4, 1H), 5.46 (br s, 1H), 5.21 (br s, 1H), 4.76-4.82 (m, 1H), 4.42-4.48 (m, 1H), 4.28-4.38 (m, 1H), 4.22-4.28 (m, 1H), 3.94-4.04 (m, 2H), 2.54 (br s, 3H), 2.23 (br s, 1H), 0.98 (d, J=7.0, 3H), 0.88 (d, J=7.0, 3H). Elemental analysis for C$_{16}$H$_{23}$N$_5$O$_7$S.HCl: calc'd: C, 41.25; H, 5.02; N, 15.03; S, 6.88; Cl, 7.61; found: C, 40.57; H, 5.37; N, 13.57; S, 6.16; Cl, 7.29.

the mixture. After five minutes, the reaction was placed in a 60° C. oil bath for 1.5 h, and was monitored by TLC (20% MeOH—CHCl$_3$) for the formation of the pyridinium cation. The 0.2 R$_f$ starting material was converted to a baseline spot that underwent blue fluorescence upon exposure to 254 nm UV light. Upon conversion to the activated intermediate, the reaction flask was placed in an ice bath. After allowing the temperature to equilibrate, 30% aqueous NH$_3$ (25 mL) was Scheme 2

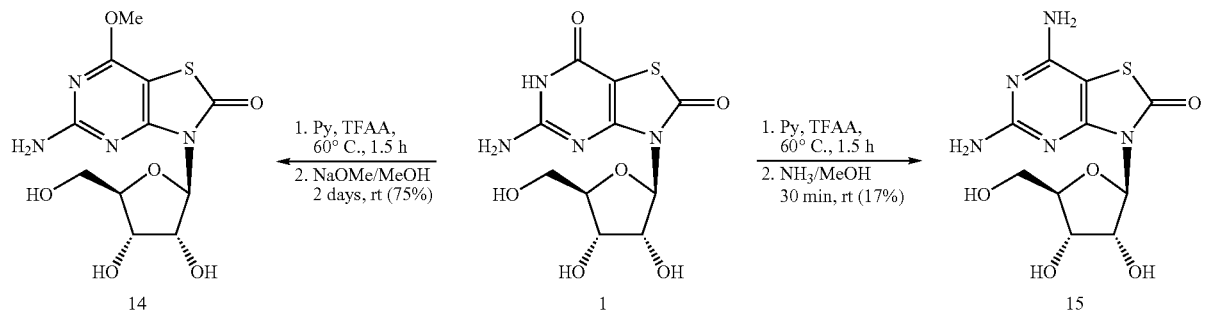

EXAMPLE 5

5-Amino-3-β-D-ribofuranosyl-7-methoxy-thiazolo[4,5-d]pyrimidin-2-one (14)

Anhydrous 1 (2.0 g, 6.3 mmol) was dissolved in dry pyridine under an argon atmosphere. The solution was cooled to 0° C., whereupon TFAA (13.3 g, 63 mmol) was added dropwise to the mixture. After five minutes, the reaction was placed in a 60° C. oil bath for 1.5 h, and was monitored by TLC (SiO$_2$, 20% MeOH—CHCl$_3$) for the formation of the pyridinium cation. The 0.2 R$_f$ starting material was converted to a baseline spot that underwent blue fluorescence upon exposure to 254 nm UV light. Upon conversion to the activated intermediate, freshly made sodium methoxide (1.8 g Na, 78 mmol, 300 ml methanol) solution was added to the reaction at 0° C. The reaction was allowed to warm to room temperature and progress for two days. The mixture was then quenched with 1M NH$_4$Cl (100 mL), and extracted with a 25% IPA-CHCl$_3$ (5×100 mL). The crude material was filtered through a silica gel plug, and then concentrated to afford 1.6 g (75%) of the title compound 14. An analytical sample was obtained by preparative TLC (SiO$_2$; water, methanol, ethyl acetate, 5:10:85) as a white solid: mp >160° C. (dec); [M+H]$^+$ 330.9, [2M+H]$^+$ 661.1, [3M+H]$^+$ 991.0; R$_f$=0.6 (20% MeOH—CHCl$_3$); mp 200.4° C.-200.9° C.; $^1$H NMR (400 MHz, d$_6$-DMSO) δ 6.92 (s, 2H), 5.86 (d, J=5.2, 1H), 5.28 (d, J=5.6, 1H), 4.96 (d, J=5.2, 1H), 4.78 (dd, J=10.8, 5.6, 1H), 4.67 (t, J=6.0, 1H), 4.07-4.10 (m, 1H), 3.91 (s, 3H), 3.70-3.80 (m, 1H), 3.55-3.60 (m, 1H), 3.40-3.45 (m, 1H). Elemental Analysis for C$_{11}$H$_{14}$N$_4$O$_6$S: calc'd: C, 40.00; H, 4.27; N, 16.96; S, 9.71; found: C, 40.07; H, 4.43; N, 16.71; S, 9.53.

EXAMPLE 6

5,7-Diamino-3-β-D-ribofuranosylthiazolo[4,5-d]pyrimidin-2-one (15)

Anhydrous 1 (0.3 g, 0.9 mmol) was dissolved in dry pyridine under an argon atmosphere. The solution was cooled to 0° C., then TFAA (1.2 mL, 9.5 mmol) was added dropwise to added dropwise until cessation of exotherm, and the remainder was added. Within a few minutes, the product formed as indicated by analytical TLC R$_f$ 0.25 (SiO$_2$, 20% MeOH—CHCl$_3$). The flask was warmed to room temperature over 30 min, then the aqueous solution was degassed under rotary vacuum then extracted with 25% IPA-CHCl$_3$ (5×100 mL). The product was submitted to flash chromatography (SiO$_2$, 10% MeOH—CHCl$_3$), yielding 55 mg (17%) of slightly impure title compound 15. An analytical sample was obtained by preparative TLC (SiO$_2$; water-MeOH—EtOAc, 5:10:85) as a white solid: mp >155° C. (dec); [M+H]$^+$ 316.0; R$_f$=0.25 (SiO$_2$, 20% MeOH—CHCl$_3$); $^1$H NMR (400 MHz, d$_6$-DMSO) δ 6.76 (s, 2H), 6.14 (s, 2H), 5.85 (d, J=5.2, 1H), 5.22 (d, J=4.8, 1H), 4.92 (d, J=2.8, 1H), 4.70-4.83 (m, 2H), 4.05-4.10 (m, 1H), 3.65-3.80 (m, 1H), 3.52-3.62 (m, 1H) 3.40-3.50 (m, 1H). Elemental Analysis for C$_{10}$H$_{13}$N$_5$O$_5$S.½H$_2$O: calc'd: C, 37.03; H, 4.35; N, 21.59; S, 9.89; found: C, 37.27; H, 4.32; N, 20.43; S, 10.11.

Scheme 3

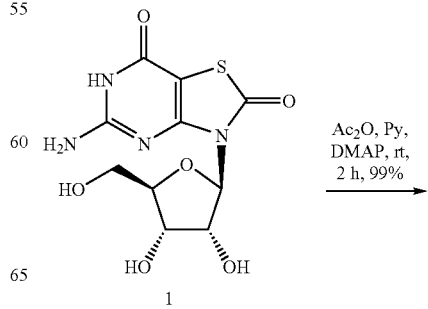

-continued

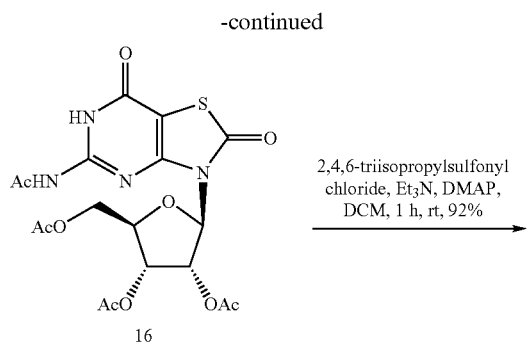

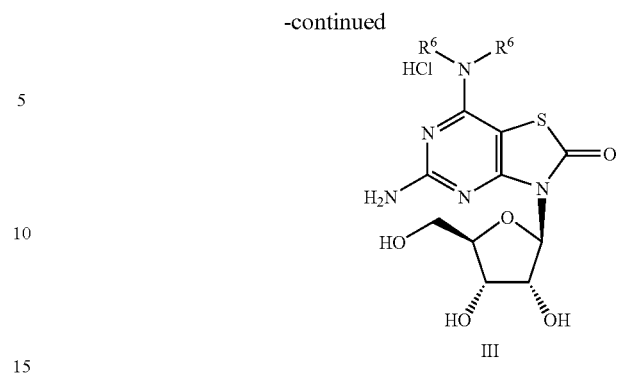

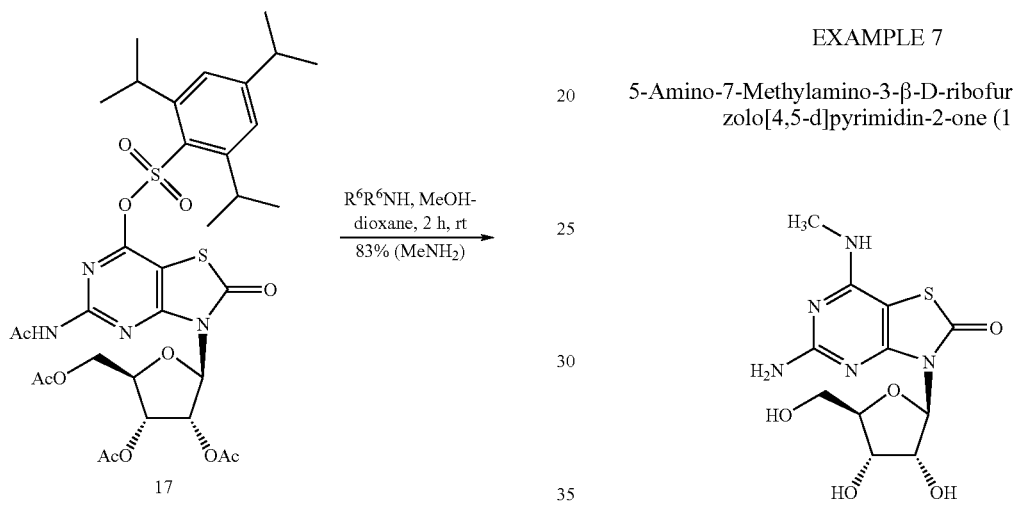

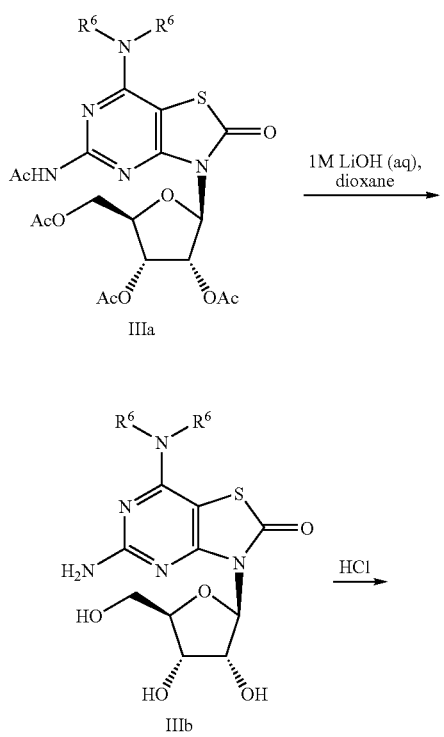

EXAMPLE 7

5-Amino-7-Methylamino-3-β-D-ribofuranosyl)thiazolo[4,5-d]pyrimidin-2-one (18)

Step 1: Preparation of 5-Acetylamino-3-(2',3',5'-tri-O-acetyl-β-D-ribofuranosyl)thiazolo[4,5-d]pyrimidine-2, 7(6H)-dione (16)

Anhydrous 1 (8.0 g, 39.5 mmol) was dissolved in dry pyridine (65 mL). DMAP (3.1 g, 25.3 mmol) and acetic anhydride (19.1 mL 202.4 mmol) were added sequentially. The reaction was allowed to progress for 2 h at room temperature, whereupon it was quenched with saturated NaHCO$_3$ (100 mL) and extracted with DCM (3×200 mL). The organic phase was concentrated, and then triturated with ether. This provided 12.5 g (103%) of slightly impure 5-acetylamino-3-(2,3,5-tri-O-acetyl-β-D-ribofuranosyl)thiazolo-[4,5-d]pyrimidin-2,7(6H)-dione as a white solid 16: mp 246.7-248.1° C.; R$_f$=0.20 (SiO$_2$, 50% EtOAc—CHCl$_3$); $^1$H NMR (400 MHz, d$_6$-DMSO) δ 12.23 (s, 1H), 11.85 (s, 1H), 5.97 (m, 2H), 5.48 (t, J=6, 1H), 4.35-4.40 (m, 1H), 4.25-4.31 (m, 1H), 4.08-4.18 (m, 1H), 2.49 (s, 3H), 2.07 (s, 3H), 2.01 (s, 3H), 2.00 (s, 3H).

Step 2: Preparation of 5-Acetylamino-7-(2,4,6-triisopropyl-benzenesulfonyloxy)-3-(2,3,5-tri-O-acetyl-β-D-ribofuranosyl)thiazolo[4,5-d]pyrimidin-2-one (17)

The intermediate from Step 1 above (500 mg, 0.98 mmol) was dissolved in DCM (15 mL) at ambient temperature. DMAP (7.3 mg, 0.06 mmol), and TEA (16 ml, 11 mmol) were added to the solution, followed by 2,4,6-triisopropylbenzenesulfonyl chloride (454 mg, 1.5 mmol). After 1 h the reaction had gone to completion, the crude mixture was concentrated, and then purified by flash chromatography (SiO$_2$, 10% EtOAc—CHCl$_3$), affording 690 mg (92%) of 5-acetylamino- 7-(2,4,6-triisopropyl-benzenesulfonyloxy)-3-(2',3',5'-tri-O-acetyl-β-D-ribofuranosyl)thiazolo[4,5-d]pyrimidin-2-one as a foaming white solid 17: 74.5-76.3° C.; $R_f$=0.7 (SiO$_2$, 20% EtOAc—CHCl$_3$); $^1$H (400 MHz, d$_6$-DMSO) δ 10.83 (s, 1H), 7.39 (s, 2H), 6.03 (d, J=4.0, 1H), 5.91-5.96 (m, 1H), 5.69 (t, J=6.4, 1H), 4.30-4.70 (m, 1H), 4.22-4.26 (m, 1H), 4.16-4.20 (m, 1H), 3.90-4.00 (m, 2H), 2.97-3.01 (m, 1H), 2.07 (s, 3H), 2.06 (s, 3H), 2.04 (s, 3H), 1.88 (s, 3H), 1.17-1.25 (m, 18H).

Step 3: Preparation of 5-Acetylamino-7-methylamino-3-(2',3',5'-tri-O-acetyl-β-D-ribofuranosyl)thiazolo[4,5-d]pyrimidin-2-one (19)

The intermediate from Step 2 above (1.7 g, 2.27 mmol) was dissolved in dioxane (20 mL) at ambient temperature. Added to this was a 2.0 M solution of methylamine (3.4 mL, 6.8 mmol) in methanol. After 2 h the starting material was consumed. The reaction mixture concentrated, and then purified by flash chromatography (SiO$_2$, gradient elution, 20-80% EtOAc—CHCl$_3$), affording 945 mg (83%) of pure title compound as a yellow oil: [M+H]$^+$ 498.2, [2M+H]$^+$ 995.4; $R_f$=0.55 (10% CH$_3$OH—CHCl$_3$); $^1$H NMR (400 MHz, d$_6$-DMSO) δ 10.13 (s, 1H), 7.70 (d, J=4.41, 1H), 5.95-6.02 (m, 2H), 5.69 (s, 1H), 4.35-4.39 (m, 1H), 4.16-4.23 (m, 2H), 2.90 (d, J=4.8, 3H), 2.20 (s, 3H), 2.07 (s, 3H), 2.02 (s, 3H), 2.00 (s, 3H).

Step 4: Preparation of 5-Amino-7-Methylamino-3-β-D-ribofuranosyl)thiazolo[4,5-d]pyrimidin-2-one (18)

The intermediate from step 3 above (420 mg, 0.85 mmol) was dissolved in dioxane (4 mL), and 1 M LiOH (8.5 mL, 8.5 mmol) was added to the solution. The O-acetyl groups were removed within 40 min to give a intermediate at $R_f$=0.15 (SiO$_2$, 5% MeOH-EtOAc). After 2 h the N-acetyl was removed as indicated by TLC $R_f$=0.20 (SiO$_2$, 5% MeOH-EtOAc). The reaction mixture was neutralized with stoichiometric acetic acid, extracted with 25% IPA-CHCl$_3$, and then concentrated to afford 195 mg (70%) of 18. An analytical sample of the title compound 18 was obtained by preparative TLC (SiO$_2$; water-MeOH-EtOAc, 10:20:70) as a white solid: [M+H]$^+$ 330.0; $R_f$=0.20 (5% MeOH-EtOAc); mp >108° C.; $^1$H NMR (400 MHz, d$_6$-DMSO) δ 7.06 (d, J=3.6, 1H), 6.24 (s, 2H), 5.85 (d, J=5.2, 1H), 5.22 (d, J=4.8, 1H), 4.93 (d, J=5.2, 1H), 4.70-4.80 (m, 2H), 4.07 (d, J=4.8, 1H), 3.75 (d, J=4.4, 1H), 3.5-3.6 (m, 1H), 3.40-3.50 (m, 1H), 2.82 (d, J=4.4, 3H).

EXAMPLE 8

5-Amino-7-dimethylamino-3-β-D-ribofuranosylthiazolo[4,5-d]pyrimidin-2-one (20)

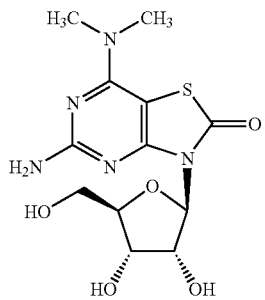

Step 1: Preparation of 5-Acetylamino-7-dimethylamino-3-(2',3',5'-tri-O-acetyl-β-D-ribofuranosyl)-thiazolo[4,5-d]pyrimidin-2-one In a manner similar to Example 7, step 2,5-acetylamino-7-dimethylamino-3-(2',3',5'-tri-O-acetyl-β-D-ribofuranosyl)-thiazolo[4,5-d]pyrimidin-2-one was generated in an 80% yield as a yellow oil: M+511.14; $R_f$=0.70 (SiO$_2$, 10% MeOH—CHCl$_3$); $^1$H NMR (400 MHz, d$_6$-DMSO) δ 10.15 (s, 1H), 6.10-6.15 (m, 1H), 5.98-6.09 (m, 1H), 5.5.66-5.70 (m, 1H), 4.35-4.40 (m, 1H), 4.22-4.27 (m, 1H), 4.14-4.08 (m, 1H), 3.18 (s, 6H), 2.19 (s, 3H), 2.08 (s, 3H), 2.06 (s, 3H), 1.99 (s, 3H).

Step 2: Preparation of 5-Amino-7-dimethylamino-3-β-D-ribofuranosylthiazolo[4, 5-d]pyrimidin-2-one (20)

In a manner similar to Example 7, step 3, the title compound 20 was generated in 82% yield. An analytical sample was obtained by preparative TLC (SiO$_2$; water-MeOH-EtOAc, 10:20:70) as a white solid: [M+H]$^+$ 344.0; [2M+H]$^+$ 687.4; $R_f$=0.20 (5% MeOH-EtOAc); mp >112° C.; $^1$H NMR (400 MHz, d$_6$-DMSO) δ 6.27 (s, 2H), 5.91 (d, J=4.8, 1H), 5.22 (d, J=6.0, 1H), 4.93 (d, J=5.2, 1H), 4.71-4.76 (m, 2H), 4.07-4.09 (m, 1H), 3.7-3.8 (m, 1H), 3.5-3.6 (m, 1H), 3.5-3.6 (m, 1H), 3.09 (s, 6H). Elemental analysis for C$_{12}$H$_{17}$N$_5$O$_5$S: calc'd: C, 41.98; H, 4.99; N, 20.40; found: C, 41.32; H, 5.14; N, 18.59.

EXAMPLE 9

5-Amino-7-cyclopropylamino-3-β-D-ribofuranosylthiazolo[4,5-d]pyrimidin-2-one monohydrochloride salt (21)

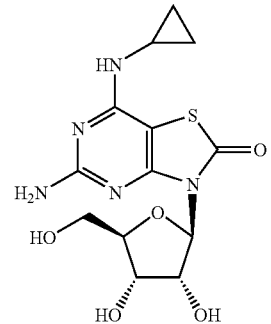

Step 1: Preparation of 5-Acetylamino-7-cyclopropylamino-3-(2',3',5'-tri-O-acetyl-β-D-ribofuranosyl)-thiazolo[4,5-d]pyrimidin-2-one In a manner similar to Example 3, step 2,5-acetylamino-7-cyclopropylamino-3-(2',3',5'-tri-O-acetyl-β-D-ribofuranosyl)-thiazolo[4,5-d]pyrimidin-2-one was generated in 80% yield as a yellow oil: $R_f$=0.45 (SiO$_2$, 75% EtOAc—CHCl$_3$); $^1$H NMR (400 MHz, D$_6$-DMSO) δ 10.11 (s, 1H), 7.87 (d, J=2.8, 1H), 5.98-6.01 (m, 1H), 5.70-5.76 (s, 1H), 4.32-4.39 (m, 1H), 4.16-4.30 (m, 2H), 3.85 (s, 1H), 2.87 (s, 1H), 2.25 (s, 3H), 2.07 (s, 3H), 2.06 (s, 3H), 1.98 (s, 3H), 0.73-0.76 (m, 2H), 0.57-0.60 (m, 2H).

Step 2: Preparation of 5-Amino-7-cyclopropylamino-3-β-D-ribofuranosylthiazolo[4,5-d]pyrimidin-2-one In a manner similar to Example 7, step 3,5-amino-7-cyclopropylamino-3-β-D-ribofuranosylthiazolo[4,5-d]pyrimidin-2-one was generated in 79% yield. An analytical sample was obtained by preparative TLC (SiO$_2$; water-MeOH-EtOAc, 10:20:70) as a white solid: R$_f$=0.20 (5% MeOH-EtOAc); mp >100° C.; [M+H]$^+$ 356.0; $^1$H (400 MHz, d$_6$-DMSO) δ 7.24 (s, 1H), 6.28 (s, 2H), 5.86 (d, J=5.6, 1H), 5.22 (d, J=6, 1H), 4.92 (d, J=5.2, 1H), 4.70-4.80 (m, 2H), 4.05-4.10 (m, 1H), 3.7-3.8 (m, 1H), 3.5-3.6 (m, 1H), 3.45-3.50 (m, 1H), 2.8 (s, 1H), 0.68-0.70 (m, 2H), 0.54-0.57 (m, 2H).

Step 3: Preparation of 5-Amino-7-cyclopropylamino-3-β-D-ribofuranosylthiazolo[4,5-d]pyrimidin-2-one hydrochloride salt (21)

The title compound was prepared by addition of the solid material prepared in step 2 above to vigorously stirring 4 M HCl in dioxane, affording the title compound as a white solid: mp >99° C.; $^1$H NMR (400 MHz, d$_6$-DMSO) δ 7.25 (d, 1H, J=2.8, 1H), 6.23 (s, 2H), 5.87 (d, J=5.2, 1H), 5.21 (bs, 1H), 4.98 (bs, 1H), 4.73-4.79 (m, 2H), 4.09 (t, J=5.6, 1H), 3.72-3.79 (m, 1H), 3.55-3.60 (m, 1H), 3.45-3.37 (m, 1H), 2.75-2.82 (m, 1H), 0.72-0.79 (m, 2H), 0.55-0.63 (m, 2H). Elemental analysis for C$_{13}$H$_{17}$N$_5$O$_5$S.HCl: calc'd: C, 39.85; H, 4.63; N, 17.87; Cl, 9.05; found: C, 39.66; H, 4.85; N, 16.57; Cl, 8.13.

EXAMPLE 10

5-Amino-7-cyclopentylamino-3-β-D-ribofuranosylthiazolo[4,5-d]pyrimidin-2-one (22)

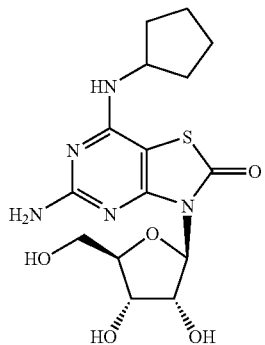

Step 1: Preparation of 5-Acetylamino-7-pyrrolidino-3-(2',3',5'-tri-O-acetyl-β-D-ribofuranosyl)-thiazolo[4,5-d]pyrimidin-2-one In a manner similar to Example 7, step 2,5-acetylamino-7-pyrrolidino-3-(2',3',5'-tri-O-acetyl-β-D-ribofuranosyl)-thiazolo[4,5-d]pyrimidin-2-one was generated in 70% yield. An analytical sample was obtained via preparative TLC (SiO$_2$; water-MeOH-EtOAc, 10:20:70) as a white solid: mp >108° C. (dec); R$_f$=0.80 (10% water and 20% methanol in ethyl acetate); [M+H]$^+$ 384.0; $^1$H NMR (400 MHz, d$_6$-DMSO) δ 7.00 (d, J=7.2, 1H), 6.17 (s, 2H), 5.18 (d, J=5.2, 1H), 5.21 (d, J=5.6, 1H), 4.92 (d, J=5.6, 1H), 4.74-4.80 (m, 2H), 4.30-4.35 (m, 1H), 4.05-4.10 (m, 1H), 3.70-3.80 (m, 1H), 3.55-3.60 (m, 1H), 3.30-3.45 (m, 1H), 1.40-2.0 (m, 8H).

Step 2: Preparation of 5-Amino-7-cyclopentylamino-3-β-D-ribofuranosylthiazolo[4,5-d]pyrimidin-2-one In a manner similar to Example 7, step 3, the title compound 22 was generated in 70% yield. An analytical sample was obtained via preparative TLC (SiO$_2$; water-MeOH-EtOAc, 10:20:70) as a white solid: mp >108° C. (dec); R$_f$=0.80 (10% water and 20% methanol in ethyl acetate); [M+H]$^+$ 384.0; $^1$H NMR (400 MHz, d$_6$-DMSO) δ 7.00 (d, J=7.2, 1H), 6.17 (s, 2H), 5.18 (d, J=5.2, 1H), 5.21 (d, J=5.6, 1H), 4.92 (d, J=5.6, 1H), 4.74-4.80 (m, 2H), 4.30-4.35 (m, 1H), 4.05-4.10 (m, 1H), 3.70-3.80 (m, 1H), 3.55-3.60 (m, 1H), 3.30-3.45 (m, 1H), 1.40-2.0 (m, 8H).

EXAMPLE 11

5-Amino-7-pyrrolidino-3-β-D-ribofuranosylthiazolo[4,5-d]pyrimidin-2-one (23)

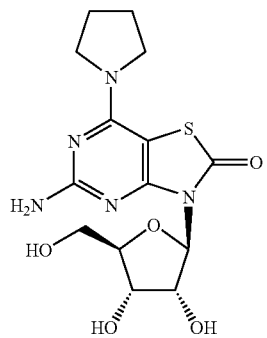

Step 1): Preparation of 5-Acetylamino-7-pyrrolidino-3-(2',3',5'-tri-O-acetyl-β-D-ribofuranosyl)thiazolo[4,5-d]pyrimidin-2-one In a manner similar to Example 7, step 2,5-acetylamino-7-pyrrolidino-3-(2,3,5-tri-O-acetyl-β-D-ribofuranosyl)-thiazolo[4,5-d]pyrimidin-2-one was generated in 79% yield as a yellow oil: [M+H]$^+$ 538.1; R$_f$=0.80 (SiO$_2$, water-MeOH-EtOAc, 10:20:70); $^1$H (400 MHz, D$_6$-DMSO) δ 10.04 (s, 1H), 5.97-6.02 (m, 2H), 5.68 (s, 1H), 4.38 (dd, J=11.6, 3.6, 1H), 4.15-4.23 (m, 2H), 3.58 (s, 4H), 2.23 (s, 3H), 2.08 (s, 3H), 2.05 (s, 3H), 1.98 (s, 3H), 1.89 (s, 4H).

Step 2: Preparation of 5-Amino-7-pyrrolidino-3-β-D-ribofuranosylthiazolo[4,5-d]pyrimidin-2-one In a manner similar to Example 7, step 3, the title compound 23 was generated in 81% yield. An analytical sample was obtained via preparative TLC (SiO$_2$; water-MeOH-EtOAc, 10:20:70) as a white solid: mp >112.4° C. (dec); [M+H]$^+$ 370.3; $^1$H NMR (400 MHz, d$_6$-DMSO) δ 6.22 (s, 2H), 5.90 (d, J=4.8, 1H), 5.23 (d, J=5.2, 1H), 4.94 (d, J=4.4, 1H), 4.68-4.75 (m, 2H), 4.08 (d, J=4.8, 1H), 3.71-3.76 (m, 1H), 3.55 (bs, 5H), 3.38-3.54 (m, 1H), 1.87 (s, 4H).

Scheme 4

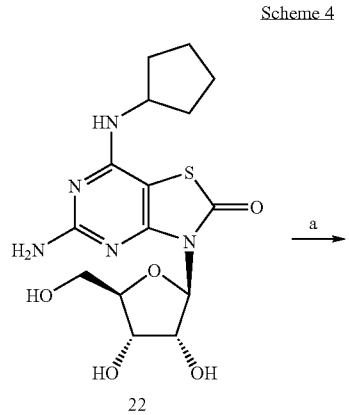

22

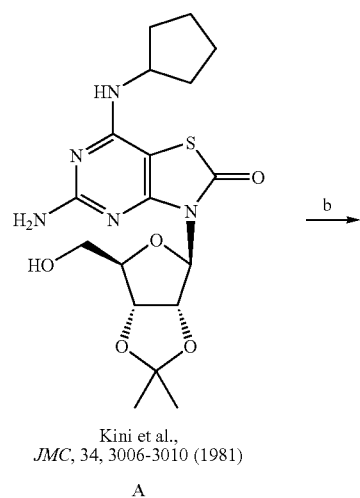

Kini et al.,
JMC, 34, 3006-3010 (1981)

A

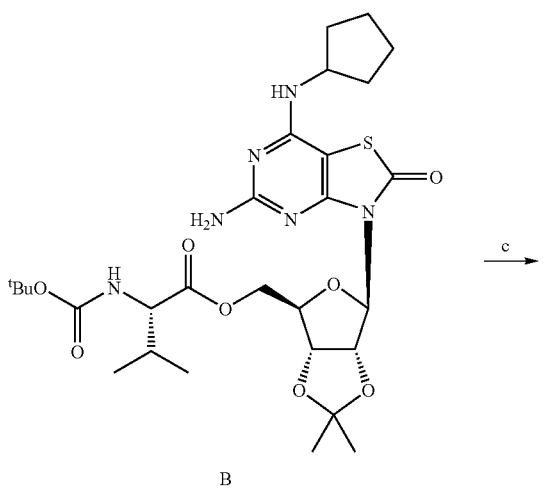

B

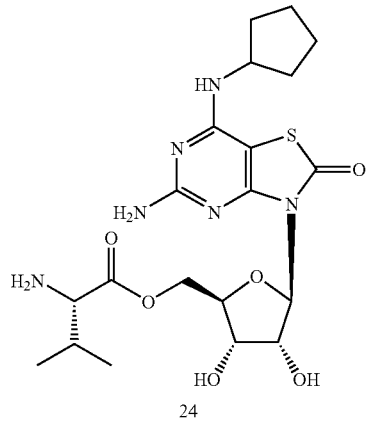

24 a) 2,2-dimethoxypropane, acetone, DMSO, MeSO$_3$H, 0° C.
b) BOC-L-valine, EDC, DMAP, PhMe, 0° C.-rt
c) anh. HCl, iPrOAc, iPrOH

EXAMPLE 12

5-Amino-7-cyclopentylamino-3-(5'-O-L-valinyl)-β-D-ribofuranosyl)thiazolo[4,5-d]pyrimidin-2-one Hydrochloride (24)

With vigorous stirring, intermediate B is dissolved in a solution of anhydrous hydrogen chloride in isopropyl acetate at 0° C. and allowed to warm to room temperature. To the heterogeneous mixture is added additional isopropyl acetate. The reaction mixture is stirred for an additional 12 h. Toluene is added and the product is filtered and dried under vacuum to yield the desired di-HCl salt 24.

The intermediates are prepared as follows:

5-Amino-7-cyclopentylamino-3-(2',3'-O-isoproylidene-β-D-ribofuranosyl)thiazolo[4,5-d]pyrimidine-2-one (A)

Compound A is prepared according to the procedure of Kini et al., by stirring a mixture of 5-amino-7-cyclopentylamino-3-β-D-ribofuranosylthiazolo[4,5-d]pyrimidine-2-one 22 with acetone, DMSO, methanesulfonic acid and an excess of dimethoxypropane at 0° C. until starting material is consumed. The reaction mixture is added to ice water and neutralized to pH 7 with saturated NaHCO$_3$ and extracted with EtOAc. The organic layer is concentrated and subjected to column chromatography on silica providing the 2',3'-protected diol product.

5-Amino-7-cyclopentylamino-3-(5'-O—(N-(tert-butoxycarbonyl)-L-valinyl)-2,3'-O-isoproylidene-β-D-ribofuranosyl)thiazolo[4,5-d]pyrimidine-2-one (B)

To a solution of 1.0 equivalents of N-(tert-butoxycarbonyl)-L-valine in THF at 0° C. is added 1.1 equivalents of EDC. After stirring for 30 min. 1.0 equivalent of 5-amino-7-cyclopentyl-3-(2',3'-O-isoproylidene-β-D-ribofuranosyl) thiazolo[4,5-d]pyrimidine-2-one, A, and 1.5 equivalents DMAP are added. The reaction mixture is warmed to room temperature and allowed to stir for 5 h, and concentrated. The residue is dissolved in EtOAc, partitioned with 1 N HCl, and neutralized with saturated aqueous NaHCO$_3$ (10 mL). The aqueous phase is further extracted with EtOAc. The combined organic phases are dried over Na$_2$SO$_4$, filtered, and evaporated under vacuum to give intermediate B that is purified by column chromatography on silica.

Schemes 5a-5c

Schemes 5a-c show general procedures for preparing 5-Amino-7-alkoxy-3-β-D-ribofuranosylthiazolo[4,5-d]pyrimidin-2-ones.

Scheme 5a

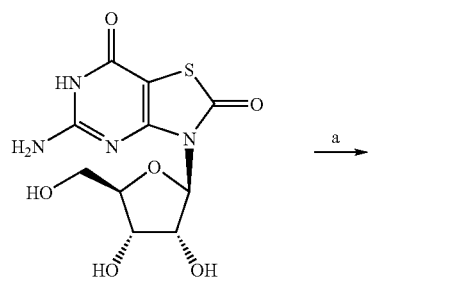

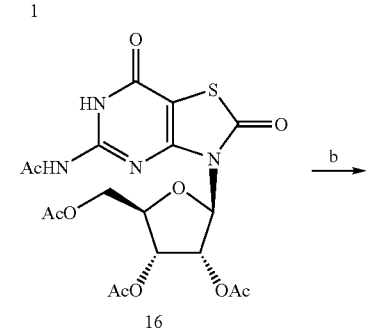

Scheme 5b

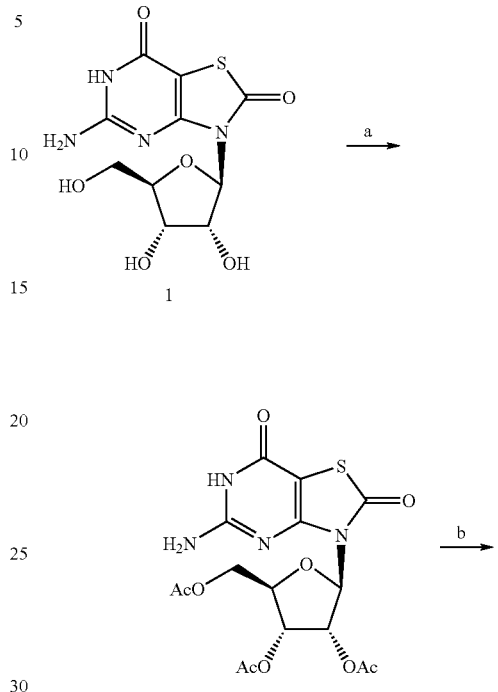

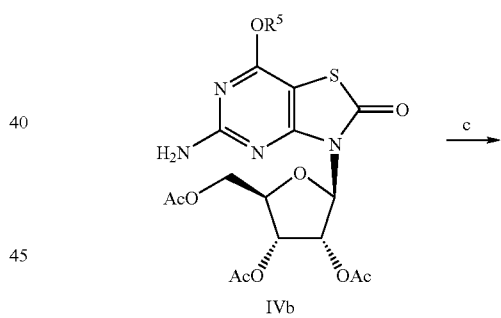

a) Ac$_2$O, Et$_3$N, MeCN
b) polymer-supported PPh$_3$, R$^5$OH, diethyl azodicarboxylate, THF, 0° C.-rt
c) K$_2$CO$_3$, MeOH a) Ac$_2$O, Et$_3$N, MeCN
b) polymer-supported PPh$_3$, R$^5$OH, diethyl azodicarboxylate, THF, 0° C.-rt
c) K$_2$CO$_3$, MeOH

Scheme 5c

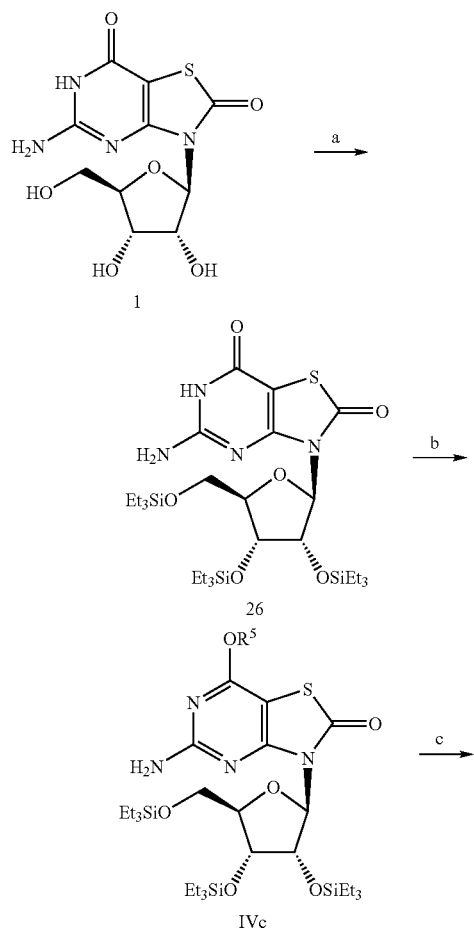

a) Et₃SiCl, imidazole, DMAP, DMF
b) polymer-supported PPh₃, R⁵OH, diethyl azodicarboxylate, THF, 0° C.-rt
c) HF, MeCN or HF·pyr, THF In a typical synthetic route, the 2',3',5'-hydroxyl groups of the β-D-ribose moiety and/or the 5-amino group of 5-amino-3-β-D-ribofuranosylthiazolo[4,5-d]pyrimidine-2,7-dione are first protected, preferably with silyl or acyl groups as shown for 16, 25 and 26. The carbonyl at the 7-position can then be subjected to a variety of alkylation methods with various alcohols to form IVa, IVb, and IVc. The 2',3',5'-hydroxyls of the ribose unit and/or the nitrogen of the 5-amino group are then subjected to appropriate deprotection conditions, to produce V. V can further be appropriately modified if so desired.

Schemes 6a-6e

Schemes 6a-6e show general procedures for preparing 5-Amino-3-β-D-ribofuranosyl-3H-thiazolo[4,5-d]pyrimidin-2-one.

Scheme 6a

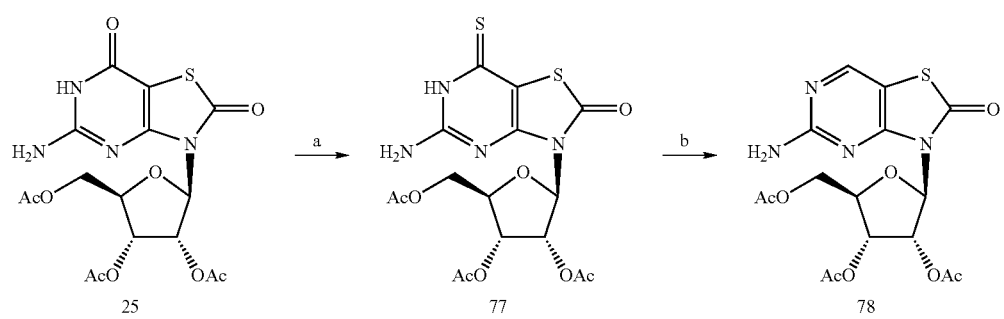

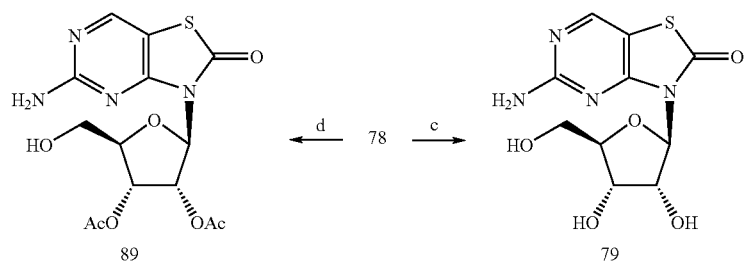
a) P₂S₅, pyr.
b) Ni, acetone, reflux
c) K₂CO₃, MeOH
d) *candida antarctica* lipase, pH7, acetone
Scheme 6b
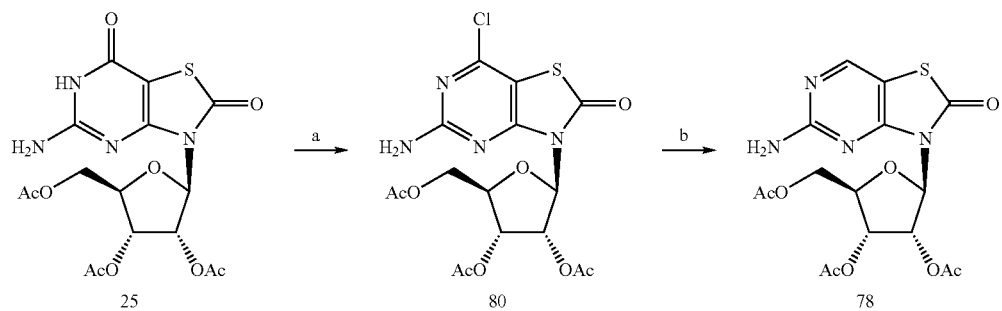
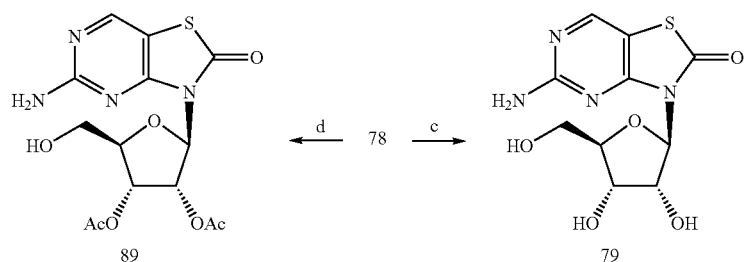
a) POCl₃, NEt₃, CHCl₃, reflux
b) Zn—Cu, AcOH, 80° C.
c) K₂CO₃, MeOH
d) *candida antarctica* lipase, pH7, acetone Scheme 6c
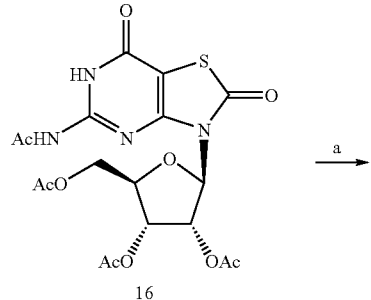
16
a →
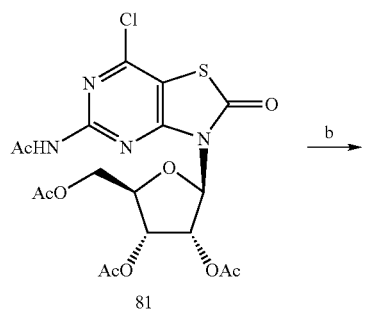
81
b →
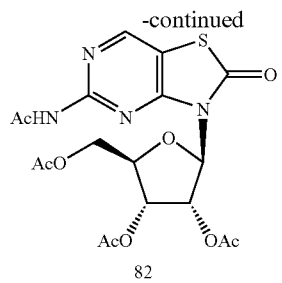
82
c →
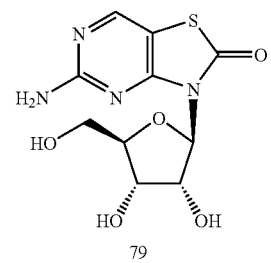
79
a) POCl₃, NEt₃, CHCl₃, 60° C.
b) 10% Pd/C, H₂, 250 psi, NaOAc, EtOH
c) K₂CO₃, MeOH
Scheme 6d
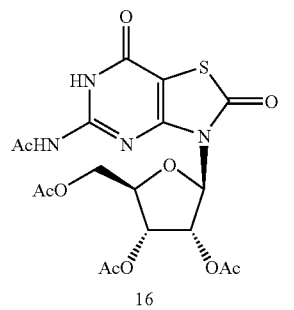
16
a →
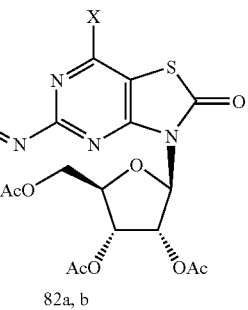
82a, b
b →
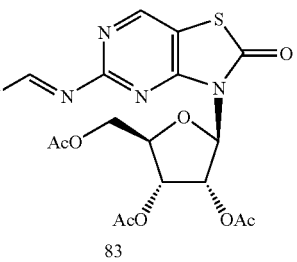
83
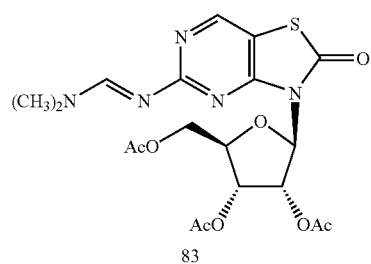
83
c
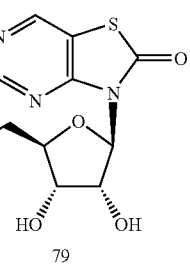
79
a) SOCl₂, DMF, CHCl₃, 60° C. or SOBr₂, DMF, CHCl₃, toluene 110° C.
b) Zn, AcOH
c) K₂CO₃, MeOH Scheme 6e

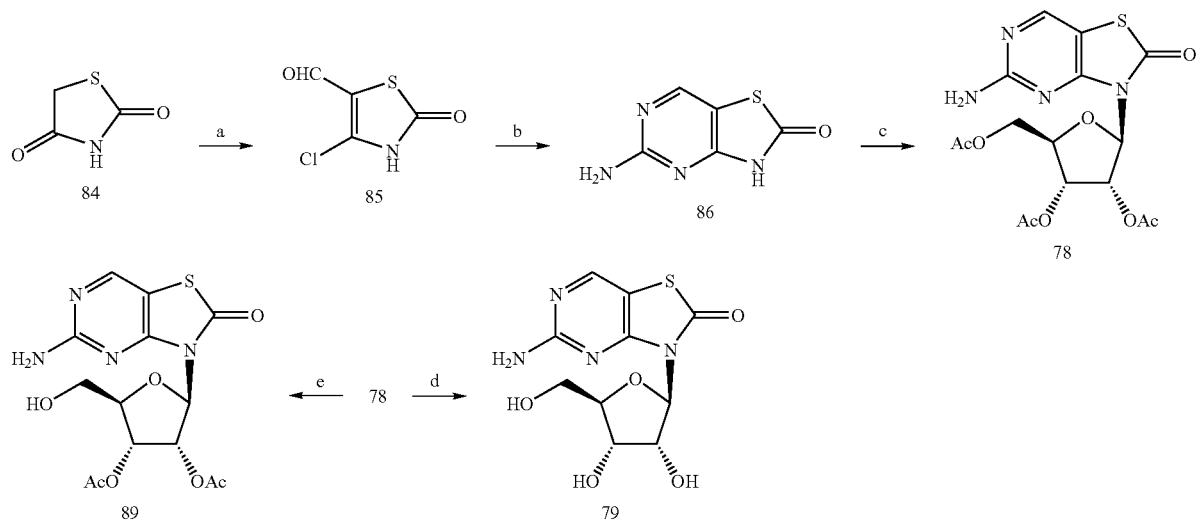

a) POCl$_3$, DMF, 100° C.
b) guanidine•HCl, K$_2$CO$_3$, NaHCO$_3$, DMF, 110° C.
c) 1,2,3,5-tetra-O-acetyl-β-D-ribofuranose, cat. bis-(4-nitrophenyl) phosphate, 160° C.
d) K$_2$CO$_3$, MeOH
e) *candida antarctica* lipase, pH7, acetone In other typical synthetic routes, 5-amino-3-β-D-ribofuranosylthiazolo[4,5-d]pyrimidine-2,7-dione 1, protected at the 2',3',5'-hydroxyl groups of the β-D-ribose and/or the 5-amino group, preferably with an acyl groups as shown for 16 or 25, can be subjected to a variety of conditions to convert the C-7 carbonyl at the 7-position to various groups, including but not limited to mercapto and halogen, that are susceptible to reduction. Following reduction under hetero- or homogeneous reaction conditions, the 2',3',5'-hydroxyls of the ribose unit and/or the nitrogen of the 5-amino group are then subjected to appropriate deprotection conditions, to produce 79. Compound 79 can further be appropriately modified if so desired. In an alternate method 5-amino-3H-thiazolo[4,5-d]pyrimidin-2-one was synthesized and further subjected to an appropriate β-D-ribose derivative under various glycosylation conditions.

Scheme 7 shows a general procedure for preparing esters of 5-Amino-7 substituted and 7-unsubstituted-3-β-D-ribofuranosyl-3H-thiazolo[4,5-d]pyrimidin-2-one.

-continued

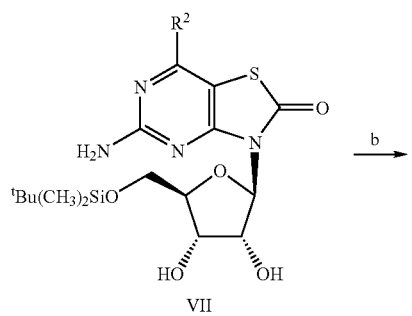

Scheme 7

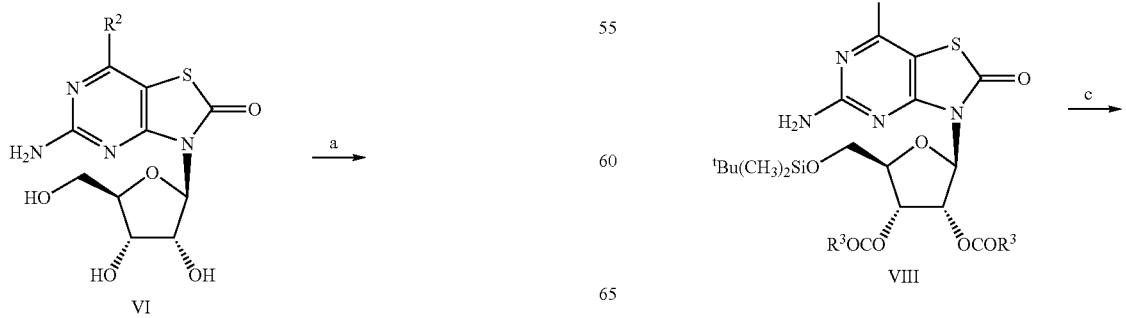

-continued

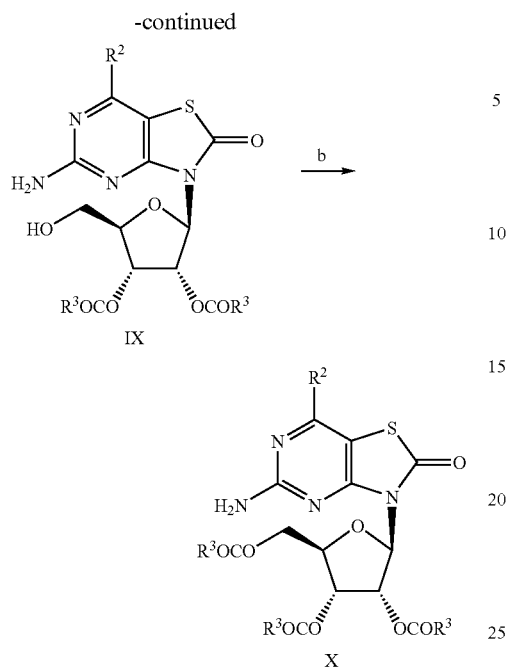

a) ᵗBuMe₂SiCl, imidazole, DMF
b) acid anhydride, Et₃N, CH₃CN
c) HF·pyr or nBu₄NF In a typical synthetic route, the 5'-hydroxyl group of the β-D-ribose moiety 5-amino-3-β-D-ribofuranosylthiazolo[4,5-d]pyrimidine is first selectively protected, preferably with an appropriate silyl group as shown for VII. The 2'- and 3'-hydroxyl groups can then be subjected to a variety of esterification methods to form VIII. The 5'-hydroxyl of the ribose unit is then subjected to appropriate deprotection conditions, to produce IX. IX can further be appropriately modified if so desired.

Scheme 8 shows a general procedure for esterification of 5-Amino-3-(5'-O-amino acid esters)-β-D-ribofuranosyl)-thiazolo[4,5-d]pyrimidin-2,7-diones.

-continued

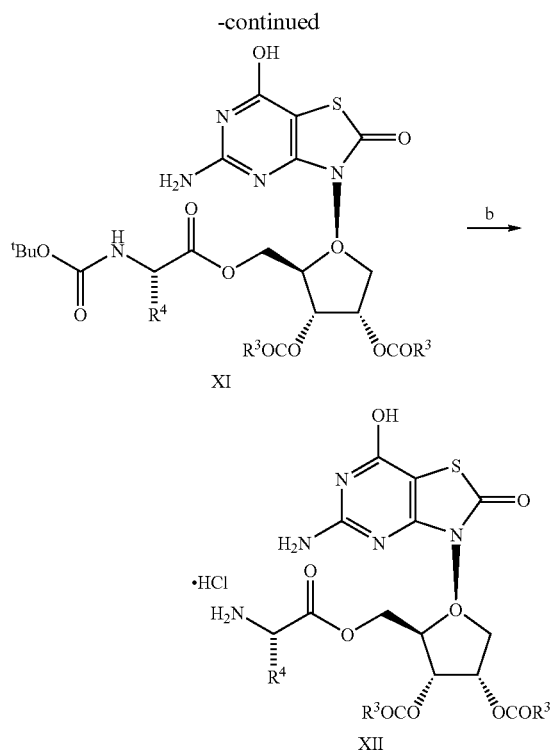

a) di-ᵗbutyldicarbonate, Et₃N, CH₃CN, acid anhydride
b) HCl, dioxane

In a typical synthetic route, the N-terminal amine of the 5'-amino acid ester of II is first selectively protected, preferably with an appropriate alkoxy-carbonyl group, followed by esterification of the 2' and 3' hydroxyl groups as shown for XI. The N-terminal amine is then subjected to appropriate deprotection conditions, to produce XII.

Scheme 9 shows a general procedure for esterification of 5-Amino-3-β-D-ribofuranosyl)-thiazolo[4,5-d]pyrimidin-2,7-diones at the 5' hydroxyl with N-terminal protected peptides.

Scheme 8

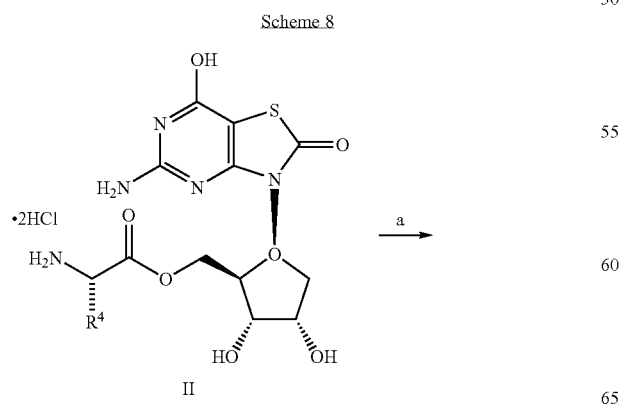

Scheme 9

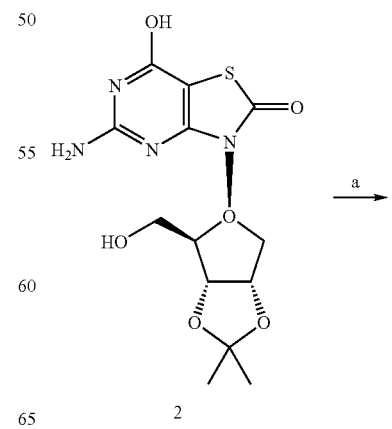

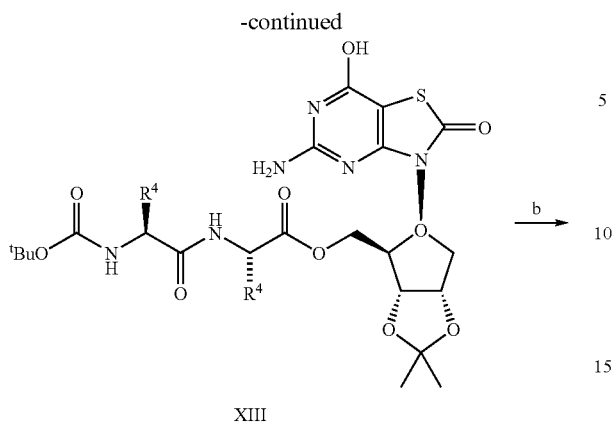

XIII

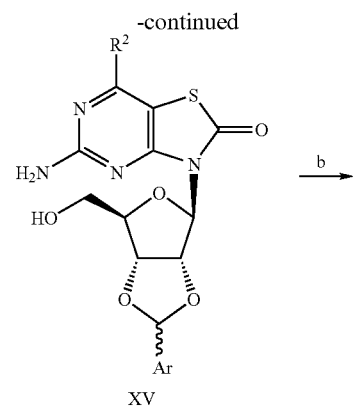

XV

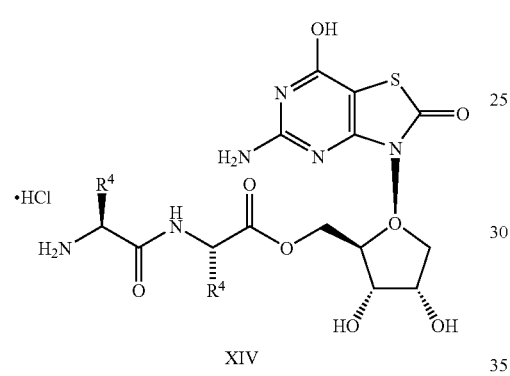

XIV

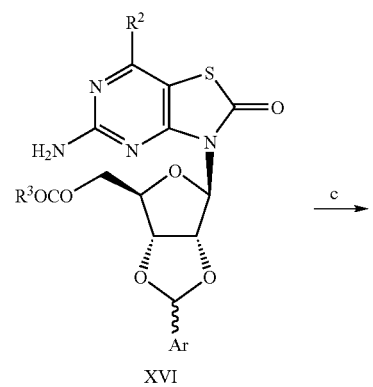

XVI a) BOCNHCH(R⁴)C(O)NHCH(R⁴)CO₂H, EDC, DMAP, pyr. DCE, 0° C.-rt
b) HCl, iPrOAc In a typical synthetic route, the 5'-hydroxyl group a 2',3'-hydroxy protected β-D-ribose moiety of 5-amino-3-β-D-ribofuranosylthiazolo[4,5-d]pyrimidine such as 2 is esterified with a N-protected terminal amine (preferably an appropriate alkoxy-carbonyl group) peptide to form the 5'-amino acid ester XIII. Both the N-terminal amine and 2',3'-hydroxy groups are then simultaneously subjected to appropriate deprotection conditions, to produce XIV.

Scheme 10 shows a general procedure for preparing 5' esters of 5-Amino-7 substituted and 7-unsubstituted-3-β-D-ribofuranosyl-3H-thiazolo[4,5-d]pyrimidin-2-one.

Scheme 10

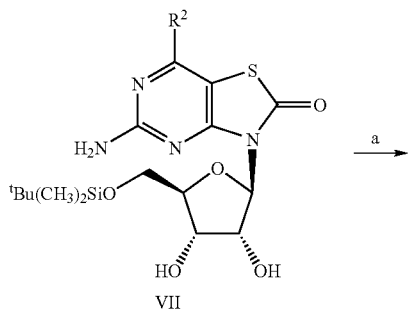

VII

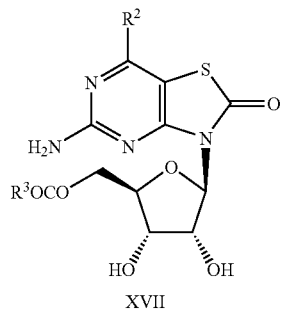

XVII a) ArCHO, H₂SO₄, THF
b) acid anhydride, Et₃N, CH₃CN
c) PPTS, CH₃OH

In a typical synthetic route, the 2'- and 3'-hydroxyl groups of 5' hydroxyl protected 5-amino-3-β-D-ribofuranosylthiazolo[4,5-d]pyrimidine such as in VII are protected. Ideally the free 5'-hydroxyl group is deprotected under conditions to protect the 2'- and 3'-hydroxyl groups as shown in XV. The 5'-hydroxyl of the ribose unit is then subjected to variety of esterification conditions with an appropriate carboxylic acid, or derivative thereof, to produce XVI. The 2',3'-hydroxyl groups of the ribose unit are then subjected to appropriate deprotection conditions, to produce XVII. XVII can further be appropriately modified if so desired.

EXAMPLE 13

5-Amino-7-isopropoxy-3-β-D-ribofuranosyl-thiazolo[4,5-d]pyrimidin-2-one (28)

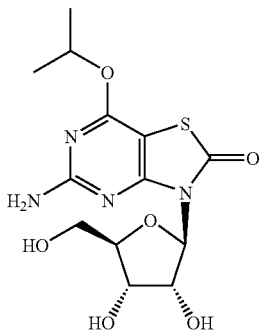

Step 1: Preparation of 5-Acetylamino-3-(2',3',5'-tri-O-acetyl-β-D-ribofuranosyl)-thiazolo[4,5-d]pyrimidine-2,7-dione (16)

Anhydrous 1 (8.17 g, 25.7 mmol) and DMAP (3.13 g, 25.7 mmol) were suspended in dry acetonitrile (125 ml). Acetic anhydride (24.5 ml, 257 mmol) was added slowly to the suspension. The reaction flask was equipped with a water-cooled reflux condenser and refluxed for 4.5 h. The reaction mixture was then poured into 600 ml of water. Solid was allowed to precipitate out for 1 h. The solid was collected, dried and triturated in ethyl ether (80 ml) for 18 h. This yielded 10.3 g (82.5%) of compound 16 as a tan solid: $^1$H NMR (400 MHz, $d_6$-DMSO) δ 12.19 (s, 1H), 11.81 (s, 1H), 5.95 (m, 2H), 5.49 (m, 1H), 4.38 (m, 1H), 4.25 (m, 1H), 4.07 (m, 1H), 2.20 (s, 3H), 2.06 (s, 3H), 2.05 (s, 3H), 2.00 (s, 3H); MS (+)-ES [M+H]$^+$ m/z 485. $R_f$=0.45 (75% Ethyl acetate-CHCl$_3$). Elemental Analysis for $C_{18}H_{20}N_4O_{10}S$: calc'd: C, 44.63; H, 4.16; N, 11.57; S, 6.62. Found: C, 44.40; H, 4.18; N, 11.58; S, 6.56.

Step 2: Preparation of 5-Acetylamino-7-isopropoxy-3-(2',3',5'-tri-O-acetyl-β-D-ribofuranosyl)-thiazolo[4,5-d]pyrimidin-2-one (27)

Compound 16 (650 mg, 1.34 mmol) and Argonaut PS-triphenylphosphine resin (4.02 mmol, 1.86 g) were placed under a dry nitrogen atmosphere in a flame-dried flask, and then dry THF (20 ml) was added. The flask was then cooled to 0° C. in an ice bath. Isopropanol (IPA) (0.20 ml, 2.68 mmol) was added followed by the dropwise addition of diethyl azodicarboxylate (DEAD) (0.366 ml, 2.0 mmol). The flask was removed from the ice bath and allowed to warm to ambient temperature. The reaction mixture was monitored for the disappearance of compound 16 by TLC. Upon consumption of 16, the solid supported material was filtered off. The crude reaction mixture was purified by flash chromatography using a 15 to 60% gradient of ethyl acetate in chloroform. Removal of the solvent afforded 460 mg (64.9%) of 27 as a white foam: MS (+)-ES [M+H]$^+$ m/z 527. $R_f$=0.7 (75% Ethyl acetate -CHCl$_3$).

Step 3: Preparation of 5-Amino-7-isopropoxy-3-β-D-ribofuranosyl-thiazolo[4,5-d]pyrimidin-2-one (28)

Compound 27 (600 mg, 1.14 mmol) was dissolved in methanol (15 ml) under a dry nitrogen atmosphere. K$_2$CO$_3$ (31.5 mg, 0.2 mmol) was added and the mixture was stirred for 18 h periodically being monitored by TLC (1:1 THF:Chloroform). The reaction mixture was concentrated under vacuum and purified by flash column chromatography (3% methanol in chloroform). The isolated solid was triturated with ethyl ether yielding 210 mg (51%) of pure 28 as a white solid: $^1$H NMR (400 MHz, $d_6$-DMSO) δ 6.83 (s, 2H), 5.86 (d, J=5.2 Hz, 1H), 5.34 (m, 1H), 5.26 (d, J=5.6 Hz, 2H), 4.95 (d, J=5.6 Hz, 1H), 4.77 (m, 1H), 4.67 (m, 1H), 4.09 (m, 1H), 3.75 (m, 1H), 3.58 (m, 1H), 3.43 (m, 1H), 1.29 (d, J=6.4 Hz, 6H); MS (+)-ES [M+H]$^+$ m/z 359, [2M+H]$^+$ m/z 717.3. $R_f$=0.2 (50% THF—CHCl$_3$). Elemental analysis for $C_{13}H_{18}N_4O_{16}S$: calc'd: C, 43.57; H, 5.06; N, 15.63; S, 8.95. Found: C, 43.39; H, 5.07; N, 15.45; S, 8.82.

EXAMPLE 14

5-Amino-7-ethoxy-3-β-D-ribofuranosyl-thiazolo[4,5-d]pyrimidin-2-one (30)

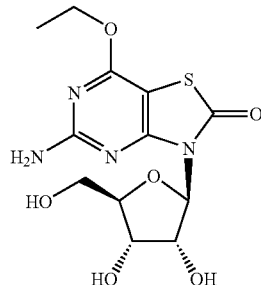

Step 1: Preparation of 5-Acetylamino-7-ethoxy-3-(2',3',5'-tri-O-acetyl-β-D-ribofuranosyl)-thiazolo[4,5-d]pyrimidin-2-one (29)

In a manner similar to Example 13, step 2, 29 was prepared from 16 and ethanol in 72% yield as a white foam: MS (+)-ES [M+H]$^+$ m/z 513. $R_f$=0.45 (75% Ethyl acetate-CHCl$_3$).

Step 2: Preparation of 5-Amino-7-ethoxy-3-β-D-ribofuranosyl-thiazolo[4,5-d]pyrimidine-2-one (30)

In a manner similar to Example 13, step 3, the title compound was prepared from 29 in 65% yield as a white solid: $^1$H NMR (400 MHz, $d_6$-DMSO) δ 6.87 (s, 2H), 5.85 (d, J=4.8 Hz, 1H), 5.27 (d, J=5.6 Hz, 1H), 4.96 (d, J=5.2 Hz, 1H), 4.78 (m, 1H), 4.66 (m, 1H), 4.36 (m, 2H), 4.09 (m, 1H), 3.74 (m, 1H), 3.58 (m, 1H), 3.40 (m, 1H), 1.29 (m, 3H); MS (+)-ES [M+H]$^+$ m/z 445, [2M+H]$^+$ m/z 689. $R_f$=0.2 (50% THF—CHCl$_3$). Elemental Analysis for $C_{12}H_{16}N_4O_6S \cdot 0.25H_2O$: calc'd: C, 41.31; H, 4.77; N, 16.06; S, 9.19. Found: C, 41.24; H, 4.71; N, 15.89; S, 9.06.

EXAMPLE 15

5-Amino-7-benzyloxy-3-β-D-ribofuranosyl-thiazolo[4,5-d]pyrimidin-2-one (32)

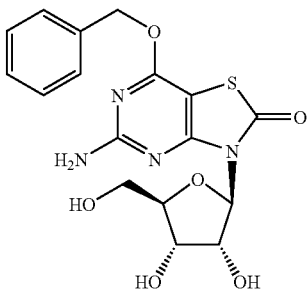

Step 1: Preparation of 5-Acetylamino-7-benzyloxy-3-(2',3',5'-tri-O-acetyl-β-D-ribofuranosyl)-thiazolo[4,5-d]pyrimidin-2-one (31)

In a manner similar to Example 13, step 2, 31 was prepared from 16 and benzyl alcohol in 77% yield as a white foam: MS (+)-ES [M+H]$^+$ 575. $R_f$=0.55 (75% Ethyl acetate-CHCl$_3$).

Step 2: Preparation of 5-Amino-7-benzyloxy-3-β-D-ribofuranosyl-thiazolo[4,5-d]pyrimidin-2-one (32)

In a manner similar to Example 13, step 3, the title compound was prepared from 31 in 62% yield as a white solid: $^1$H NMR (400 MHz, d$_6$-DMSO) δ 7.39 (bm, 5H), 6.95 (s, 2H), 5.86 (d, J=4.8 Hz, 1H), 5.43 (s, 2H), 5.28 (d, J=5.2 Hz, 1H), 4.96 (d, J=5.2 Hz, 1H), 4.80 (m, 1H), 4.66 (m, 1H), 4.09 (m, 1H), 3.76 (m, 1H), 3.42 (m, 1H); MS (+)-ES [M+H]$^+$ 407, [2M+H] 813. $R_f$=0.15 (50% THF—CHCl$_3$). Elemental Analysis for C$_{17}$H$_{18}$N$_4$O$_{16}$S: calc'd: C, 50.24; H, 4.46; N, 13.79; S, 7.89. Found: C, 49.97; H, 4.55; N, 13.44; S, 7.70.

EXAMPLE 16

5-Amino-7-(4-methoxy-benzyloxy)-3-β-D-ribofuranosyl-thiazolo[4,5-d]pyrimidin-2-one (34)

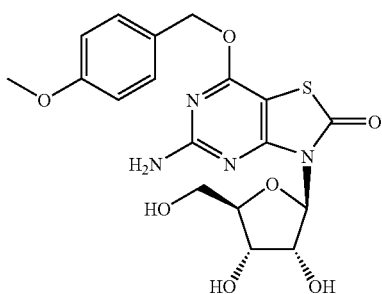

Step 1: Preparation of 5-Acetylamino-7-(4-methoxybenzyloxy)-3-(2',3',5'-tri-O-acetyl-β-D-ribofuranosyl)-thiazolo[4,5-d]pyrimidin-2-one In a manner similar to Example 13, step 2, 33 was obtained from 16 and 4-methoxyl-benzyl alcohol in 72% yield as a white foam: [M+H]$^+$ 605. $R_f$=0.5 (75% Ethyl acetate-CHCl$_3$).

Step 2: Preparation of 5-Amino-7-(4-methoxy-benzyloxy)-3-β-D-ribofuranosyl-thiazolo[4,5-d]pyrimidin-2-one (34)

In a manner similar to Example 13, step 3, the title compound was prepared from 33 in 68% yield as a white solid: $^1$H NMR (400 MHz, d$_6$-DMSO) δ 7.38 (dd, J=8.4, 2.0 Hz, 2H), 6.93 (s, 2H), 6.91 (dd, J=6.8, 2.0 Hz, 2H), 5.85 (d, J=5.2 Hz, 1H), 5.35 (s, 2H), 5.27 (d, J=5.6 Hz, 1H), 4.96 (d, J=5.2 Hz, 1H), 4.78 (m, 2H), 4.65 (m, 1H), 4.09 (m, 1H), 3.75 (m, 1H), 3.74 (m, 3H), 3.55 (m, 1H), 3.41 (m, 1H); MS (+)-ES [M+H]$^+$ 437, [2M+H]$^+$ 873. $R_f$=0.3 (50% THF—CHCl$_3$). Elemental analysis for C$_{18}$H$_{20}$N$_4$O$_7$S.1.0H$_2$O: calc'd: C, 47.57; H, 4.88; N, 12.33; S, 7.06. Found: C, 47.28; H, 4.91; N, 12.36; S, 7.10.

EXAMPLE 17

7-Allyloxy-5-Amino-3-β-D-ribofuranosyl-thiazolo[4,5-d]pyrimidin-2-one (36)

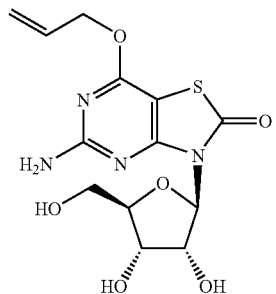

Step 1: Preparation of 5-Acetylamino-7-allyloxy-3-(2',3',5'-tri-O-acetyl-β-D-ribofuranosyl)-thiazolo[4,5-d]pyrimidin-2-one (35)

In a manner similar to Example 13, step 2, 35 was prepared from 16 and allyl alcohol in 73% yield as a white foam: [M+H]$^+$ 525. $R_f$=0.6 (75% Ethyl acetate/CHCl$_3$).

Step 2: Preparation of 7-Allyloxy-5-amino-3-β-D-ribofuranosyl-thiazolo[4,5-d]pyrimidin-2-one (36)

In a manner similar to Example 13, step 3, the title compound was prepared from 35 in 69% yield as a white foam. $^1$H NMR (400 MHz, d$_6$-DMSO) δ 6.90 (s, 2H), 6.04 (m, 1H), 5.86 (d, J=8.0 Hz, 1H), 5.26 (m, 2H), 4.96 (d, J=5.6 Hz, 1H), 4.86 (m, 1H), 4.79 (m, 2H), 4.66 (m, 1H), 4.08 (m, 1H), 3.76 (m, 1H), 3.58 (m, 1H), 3.45 (m, 1H); MS (+)-ES [M+H]$^+$ 357, [2M+H]$^+$ 713. $R_f$=0.3 (50% THF—CHCl$_3$). Elemental Analysis for C$_{13}$H$_{16}$N$_4$O$_6$S: calc'd: C, 43.82; H, 4.53; N, 15.72; S, 9.00. Found: C, 43.65; H, 4.65; N, 15.64; S, 8.96.

EXAMPLE 18

5-Amino-7-(3-methyl-but-2-enyloxy)-3-β-D-ribofuranosyl-thiazolo[4,5-d]pyrimidin-2-one (38)

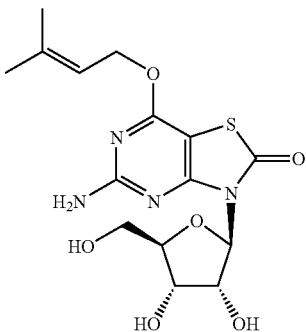

Step 1: Preparation of 5-Acetylamino-7-(3-methyl-but-2-enyloxy)-3-(2',3',5'-tri-O-acetyl-β-D-ribofuranosyl)-thiazolo[4,5-d]pyrimidin-2-one (37)

In a manner similar to Example 13, step 2, 37 was prepared from 16 and 3-methyl-but-2-en-1-ol in 76% yield as a white foam: MS (+)-ES [M+H]+ 553. $R_f$=0.8 (75% Ethyl acetate-CHCl$_3$).

Step 2: Preparation of 5-Amino-7-(3-methyl-but-2-enyloxy)-3-β-D-ribofuranosyl-thiazolo[4,5-d]pyrimidin-2-one (38)

In a manner similar to Example 13, step 3, the title compound was prepared from 37 in 68% yield as a white solid: $^1$H NMR (400 MHz, d$_6$-DMSO) δ 6.86 (s, 1H), 5.85 (d, J=4.8 Hz, 1H), 5.41 (m, 1H), 5.27 (d, J=5.6 Hz, 1H), 4.96 (d, J=5.2 Hz, 1H), 4.86 (d, J=6.8 Hz, 1H), 4.78 (m, 1H), 4.66 (m, 1H), 4.08 (m, 1H), 3.75 (m, 1H), 3.56 (m, 1H), 3.41 (m, 2H), 1.73 (s, 3H), 1.70 (s, 3H); MS (+)-ES [M+H]+ 385. $R_f$=0.35 (50% THF—CHCl$_3$). Elemental Analysis for C$_{15}$H$_{20}$N$_4$O$_6$S: calc'd: C, 46.87; H, 5.24; N, 14.57; S, 8.34. Found: C, 46.86; H, 5.24; N, 14.62; S, 8.34.

EXAMPLE 19

5-Amino-7-(prop-2-ynyl oxy)-3-β-D-ribofuranosyl-thiazolo[4,5-d]pyrimidin-2-one (40)

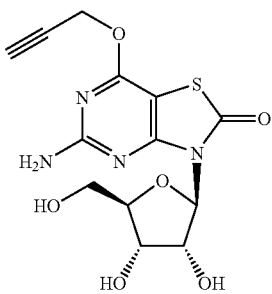

Step 1: Preparation of 5-Acetylamino-7-(prop-2-ynyl oxy)-3-(2',3',5'-tri-O-acetyl-3-β-D-ribofuranosyl)-thiazolo[4,5-d]pyrimidin-2-one (39)

In a manner similar to Example 13, step 2, 39 was prepared from 16 and propargyl alcohol in 62% yield as a white foam: MS (+)-ES [M+H]+ 523. $R_f$=0.7 (75% Ethyl acetate-CHCl$_3$).

Step 2: Preparation of 5-Amino-7-(prop-2-ynyl oxy)-3-β-D-ribofuranosyl-thiazolo[4,5-d]pyrimidin-2-one (40)

In a manner similar to Example 13, step 3, the title compound was prepared from 39 in 68% yield as a white solid: $^1$H NMR (400 MHz, d$_6$-DMSO) δ 6.99 (s, 2H), 5.86 (d, J=5.2 Hz, 1H), 5.29 (d, J=5.6 Hz, 1H), 5.04 (s, 2H), 4.97 (d, J=5.6 Hz, 1H), 4.78 (m, 1H), 4.65 (m, 2H), 4.08 (m, 1H), 3.76 (m, 1H), 3.58 (m, 1H), 3.28 (m, 1H); MS (+)-ES [M+H]+ 355. $R_f$=0.25 (50% THF—CHCl$_3$). Elemental Analysis for C$_{13}$H$_{14}$N$_4$O$_6$S.0.5H$_2$O: calc'd: C, 42.97; H, 4.16; N, 15.42; S, 9.82; found: C, 43.22; H, 4.27; N, 14.80; S, 8.47.

EXAMPLE 20

(5-Amino-2-oxo-3-β-D-ribofuranosyl-thiazolo[4,5-d]pyrimidin-7-yloxy)-acetic acid methyl ester (42)

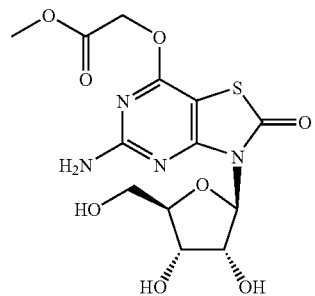

Step 1: Preparation of [5-Acetylamino-2-oxo-3-(2',3',5'-tri-O-acetyl-3-β-D-ribofuranosyl)-thiazolo[4,5-d]pyrimidin-7-yloxy]-acetic acid methyl ester (41)

In a manner similar to Example 13, step 2, 41 was prepared from 16 and hydroxyl-acetic acid methyl ester in 58% yield as a white foam: MS (+)-ES [M+H]+ 556. $R_f$=0.45 (75% Ethyl acetate-CHCl$_3$).

Step 2: Preparation of (5-Amino-2-oxo-3-β-D-ribofuranosyl-thiazolo[4,5-d]pyrimidin-7-yloxy)-acetic acid methyl ester (42)

In a manner similar to Example 13, step 3, the title compound was prepared from 41 in 57% yield as a white solid: $^1$H NMR (400 MHz, d$_6$-DMSO) δ 6.93 (s, 3H), 5.86 (d, J=5.6 Hz, 1H), 5.28 (m, 1H), 4.99 (s, 2H), 4.95 (s, 1H), 4.80 (m, 1H), 4.65 (m, 1H), 4.09 (m, 1H), 3.76 (m, 1H), 3.67 (s, 3H), 3.55 (m, 1H), 3.42 (m, 1H); MS (+)-ES [M+H]+ 389, [2M+H]+ 777.3. $R_f$=0.15 (75% THF—CHCl$_3$). Elemental Analysis for C$_{13}$H$_{16}$N$_4$O$_8$S: calc'd: C, 40.21; H, 4.15; N, 14.43; S, 8.26. Found: C, 40.07; H, 4.25; N, 14.20; S, 8.11.

EXAMPLE 21

2-(5-Amino-2-oxo-3-β-D-ribofuranosyl-thiazolo[4,5-d]pyrimidin-7-yloxy)-propionic acid methyl ester (44)

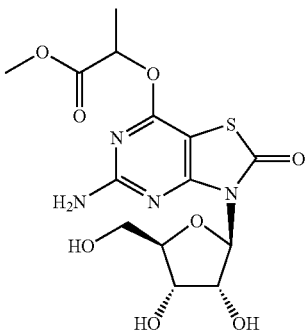

Step 1: 2-[5-Acetylamino-2-oxo-3-(2',3',5'-tri-O-acetyl-3-D-ribofuranosyl)-thiazolo[4,5-d]pyrimidin-7-yloxy]-propionic acid methyl ester (43)

In a manner similar to Example 13, step 2, 43 was prepared from 16 and (±)
2-hydroxy-propionic acid methyl ester in 55% yield as a white solid: MS (+)-ES [M+H]$^+$ 571. $R_f$=0.4 (75% Ethyl acetate-CHCl$_3$).

Step 2: 2-(5-Amino-2-oxo-3-β-D-ribofuranosyl-thiazolo[4,5-d]pyrimidin-7-yloxy)-propionic acid methyl ester (44)

In a manner similar to Example 13, step 3, the title compound was prepared from 43 in 63% yield as a white solid: $^1$H NMR (400 MHz, d$_6$-DMSO) δ 6.88 (s, 2H), 5.84 (d, J=4.0 Hz, 1H), 5.39 (m, 1H), 5.29 (d, J=5.6 Hz, 1H), 4.97 (d, J=5.6 Hz, 1H), 4.80 (m, 1H), 4.66 (m, 1H), 4.10 (m, 1H), 3.76 (m, 1H), 3.66 (s, 3H), 3.56 (m, 1H), 3.43 (m, 1H), 1.51 (d, J=6.8 Hz, 3H); MS (+)-ES [M+H]$^+$ 403, [2M+H]$^+$ 805. $R_f$=0.15 (50% THF—CHCl$_3$). Elemental Analysis for C$_{14}$H$_{18}$N$_4$O$_8$S: calc'd: C, 41.79; H, 4.51; N, 13.92; S, 7.97. Found: C, 41.77; H, 4.50; N, 13.88; S, 7.94.

EXAMPLE 22

5-Amino-7-methoxy-3-β-D-ribofuranosyl-thiazolo[4,5-d]pyrimidin-2-one (14)

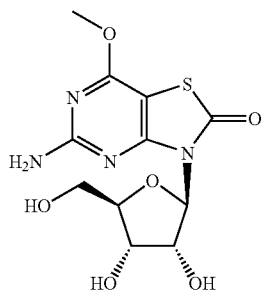

Step 1: Preparation of 5-Acetylamino-7-methoxy-3-(2',3',5'-tri-O-acetyl-β-D-ribofuranosyl)-thiazolo[4,5-d]pyrimidin-2-one (45)

In a manner similar to Example 13, step 2, 45 was prepared from 16 and methanol in 65% yield as a white foam: MS (+)-ES [M+H]$^+$ 499. $R_f$=0.5 (75% Ethyl acetate-CHCl$_3$).

Step 2: Preparation of 5-Amino-7-methoxy-3-β-D-ribofuranosyl-thiazolo[4, 5-d]pyrimidin-2-one (14)

In a manner similar to Example 13, step 3, the title compound was prepared from 45 in 78% yield as a white solid: $^1$H NMR (400 MHz, d$_6$-DMSO) δ 6.91 (s, 2H), 5.86 (d, J=5.2 Hz, 1H), 5.28 (d, J=5.2 Hz, 1H), 4.96 (d, J=5.2 Hz, 1H), 4.77 (m, 1H), 4.66 (m, 1H), 4.09 (m, 1H), 3.90 (s, 3H), 3.75 (m, 1H), 3.56 (m, 1H), 3.43 (m, 1H); MS (+)-ES [M+H]$^+$ 331. $R_f$=0.2 (50% THF—CHCl$_3$). Elemental Analysis for C$_{11}$H$_{14}$N$_4$O$_6$S.0.25H$_2$O: calc'd: C, 39.46; H, 4.37; N, 16.73; S, 9.58. Found: C, 39.59; H, 4.17; N, 16.55; S, 9.52.

EXAMPLE 23

5-Amino-7-propoxy-3-β-D-ribofuranosyl-thiazolo[4,5-d]pyrimidin-2-one (47)

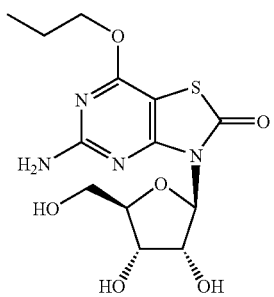

Step 1: Preparation of 5-Acetylamino-7-propoxy-3-(2',3',5'-tri-O-acetyl-β-D-ribofuranosyl)-thiazolo[4,5-d]pyrimidin-2-one (46)

In a manner similar to Example 13, step 2, 46 was prepared from 16 and n-propanol in 65% yield as a white foam: MS (+)-ES [M+H]$^+$ 527. $R_f$=0.55 (75% Ethyl acetate-CHCl$_3$).

Step 2: Preparation of 5-Amino-7-propoxy-3-D-ribofuranosyl-thiazolo[4,5-d]pyrimidin-2-one (47)

In a manner similar to Example 13, step 3, the title compound was prepared from 47 in 70% yield as a white solid: $^1$H NMR (400 MHz, d$_6$-DMSO) δ 6.87 (s, 2H), 5.85 (J=5.2 Hz, 1H), 5.28 (d, J=5.6 Hz, 1H), 4.96 (d, J=1.2 Hz, 1H), 4.80 (m, 1H), 4.66 (m, 1H), 4.29 (m, 2H), 4.08 (m, 1H), 3.75 (m, 1H), 3.56 (m, 1H), 3.42 (m, 1H), 1.71 (m, 2H), 0.92 (m, 3H); MS (+)-ES [M+H]$^+$ 359. $R_f$=0.3 (50% THF—CHCl$_3$). Elemental Analysis for C$_{13}$H$_{18}$N$_4$O$_6$S: calc'd: C, 43.57; H, 5.06; N, 15.63; S, 8.95. Found: C, 43.77; H, 5.29; N, 15.39; S, 8.81.

EXAMPLE 24

5-Amino-7-butoxy-3-β-D-ribofuranosyl-thiazolo[4,5-d]pyrimidin-2-one (49)

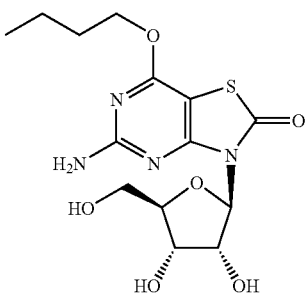

Step 1: Preparation of 5-Acetylamino-7-butoxy-3-(2',3',5'-tri-O-acetyl-β-D-ribofuranosyl)-thiazolo[4,5-d]pyrimidin-2-one(48)

In a manner similar to Example 13, step 2, 48 was prepared from 16 and n-butanol in 64% yield as a white paste: MS (+)-ES [M+H]$^+$ 541. $R_f$=0.65 (75% Ethyl acetate-CHCl$_3$).

Step 2: Preparation of 5-Amino-7-butoxy-3-β-D-ribofuranosyl-thiazolo[4,5-d]pyrimidin-2-one (49)

In a manner similar to Example 13, step 3, the title compound was prepared from 48 in 72% yield as a white solid: $^1$H NMR (400 MHz, d$_6$-DMSO) δ 6.87 (s, 2H), 5.85 (d, J=4.8 Hz, 1H), 5.28 (d, J=5.2 Hz, 1H), 4.95 (d, J=5.6 Hz, 1H), 4.77 (m, 1H), 4.34 (m, 1H), 4.07 (m, 1H), 3.74 (m, 1H), 3.58 (m, 1H), 3.41 (m, 1H), 1.63 (m, 2H), 1.31 (m, 2H), 0.92 (m, 3H); MS (+)-ES [M+H]$^+$ 373. $R_f$=0.25 (50% THF—CHCl$_3$). Elemental Analysis for C$_{14}$H$_{20}$N$_4$O$_6$S: calc'd: C, 45.15; H, 5.41; N, 15.04; S, 8.61. Found: C, 44.79; H, 5.34; N, 15.02; S, 8.60.

EXAMPLE 25

5-Amino-7-(4-fluorobenzyloxy)-3-β-D-ribofuranosyl-thiazolo-[4,5-d]pyrimidin-2-one (51)

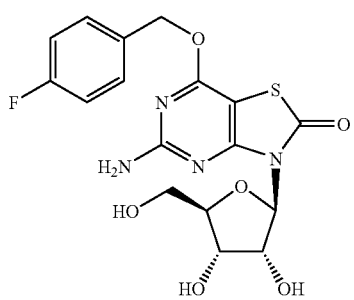

Step 1: Preparation of 5-Acetylamino-7-(4-fluorobenzyloxy)-3-(2',3',5'-tri-O-acetyl-β-D-ribofuranosyl)thiazolo-[4,5-d]pyrimidin-2-one (50)

In a manner similar to Example 13, step 2, 50 was prepared was prepared from 16 and 4-fluorobenzyl alcohol. $^1$H NMR (400 MHz, CDCl$_3$) δ 8.20 (m, 1H), 7.44 (m, 1H), 7.06 (m, 1H), 6.10 (d, J=3.2 Hz, 1H), 6.02 (dd, J=3.0, 6.0 Hz, 1H), 5.92 (t, J=5.0 Hz, 1H), 5.48 (s, 2H), 4.51 (dd, J=4.0, 6.0 Hz, 1H), 4.34 (m, 1), 4.23 (dd, J=4.0, 8.0 Hz, 1H), 2.44 (s, 3H), 2.13 (s, 3H), 2.11 (s, 3H), 2.04 (s, 3H).

Step 2: Preparation of 5-Amino-7-(4-fluorobenzyloxy)-3-β-D-ribofuranosyl-thiazolo-[4,5-d]pyrimidin-2-one (51)

In a manner similar to Example 13, step 3, the title compound was prepared from 50. $^1$H NMR (400 MHz, d$_6$-DMSO) δ 7.50 (m, 2H), 7.19 (m, 2H), 6.96 (s, 2H), 5.86 (d, J=4.8 Hz, 1H), 5.41 (s, 2H), 5.28 (d, J=5.6 Hz, 1H), 4.96 (d, J=5.6 Hz, 1H), 4.78 (q, J=5.2 Hz, 1H), 4.66 (t, J=6.0 Hz, 1H), 4.09 (q, J=5.2 Hz, 1H), 3.75 (q, J=4.8 Hz, 1H), 3.57 (m, 1H), 3.42 (m, 1H).

EXAMPLE 26

5-Amino-7-(3-hydroxy-1-propoxy)-3-β-D-ribofuranosyl-thiazolo-[4,5-d]pyrimidin-2-one (53)

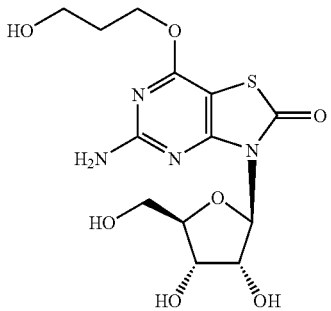

Step 1: Preparation of 5-Acetylamino-7-(3-acetoxy-1-propoxy)-3-(2',3',5'-tri-O-acetyl-β-D-ribofuranosyl)thiazolo-[4,5-d]pyrimidin-2-one (52)

In a manner similar to Example 13, step 2, 52 was prepared was prepared from 16 and 1,3-propanediol monoacetate (Dittmer, JACS, 79, 4431-35) (1957)). $^1$H NMR (400 MHz, CDCl$_3$) δ 8.17 (s, 1H), 6.10 (d, J=3.2 Hz, 1H), 6.02 (dd, J=2.8, 6.0 Hz, 1H), 5.89 (t, J=6.8 Hz, 1H), 4.56-4.89 (m, 3H), 4.34 (m, 1H), 4.26-4.20 (m, 3H), 2.46 (s, 3H), 2.15 (m, 2H), 2.13 (s, 3H), 2.11 (s, 3H), 2.07 (s, 3H), 2.06 (s, 3H).

Step 2: Preparation of 5-Amino-7-(3-hydroxy-1-propoxy)-3-β-D-ribofuranosyl-thiazolo-[4,5-d]pyrimidin-2-one (53)

In a manner similar to Example 13, step 3, the title compound was prepared from 52. $^1$H NMR (400 MHz, d$_6$-DMSO) δ 6.87 (s, 2), 5.86 (d, J=5.2 Hz, 1H), 5.28 (d, J=5.6 Hz, 1H), 4.96 (d, J=5.2 Hz, 1H), 4.78 (q, J=5.6 Hz, 1H), 4.67 (t, J=5.6 Hz, 1H), 4.53 (t, J=5.2 Hz, 1H), 4.40 (t, J=6.8 Hz, 2H), 4.09 (q, J=5.2 Hz, 1H), 3.75 (q, J=4.8 Hz, 1H), 3.57 (m, 1H), 3.50 (q, J=6.4 Hz, 2H), 3.42 (m, 1H), 1.83 (m, 2H).

EXAMPLE 27

5-Amino-7-(4-hydroxy-1-butoxy)-3-β-D-ribofuranosyl-thiazolo-[4,5-d]pyrimidin-2-one (55)

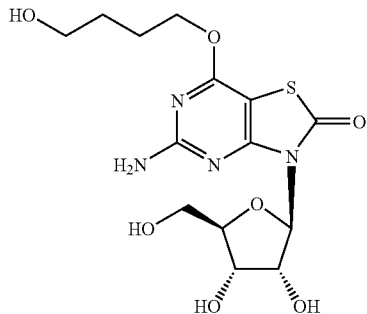

Step 1: Preparation of 5-Acetylamino-7-(4-acetoxy-1-butoxy)-3-(2',3',5'-tri-O-acetyl-β-D-ribofuranosyl)thiazolo-[4,5-d]pyrimidin-2-one (54)

In a manner similar to Example 13, step 2, 54 was prepared was prepared from 16 and 1,4-butanediol monoacetate (Clarke, *Tet. Lett.*, 43(27), 4761-64 (2002)). $^1$H NMR (400 MHz, CDCl$_3$) δ 8.15 (s, 1H), 6.10 (d, J=3.2 Hz, 1H), 6.02 (dd, J=3.2, 6.4 Hz, 1H), 5.89 (t, J=6.4 Hz, 1H), 4.50 (m, 3H), 4.32 (m, 1H), 4.24 (dd, J=6.4, 12.0 Hz, 1H), 4.13 (t, J=6.4 Hz, 1H), 2.45 (s, 3H), 2.13 (s, 3H), 2.10 (s, 3H), 2.06 (s, 3H), 2.05 (s, 3H), 1.88 (s, 3H), 1.78 (m, 2H).

Step 2: Preparation of 5-Amino-7-(4-hydroxy-1-butoxy)-3-β-D-ribofuranosyl-thiazolo-[4,5-d]pyrimidin-2-one (55)

In a manner similar to Example 13, step 3, the title compound was prepared from 54. $^1$H NMR (400 MHz, d$_6$-DMSO) δ 6.87 (s, 2H), 5.85 (d, J=5.2 Hz, 1H), 5.29 (s, 1H), 4.98 (s, 1H), 4.79 (t, J=5.2 Hz, 1H), 4.67 (s, 1H), 4.43 (t, J=4.8 Hz, 1H), 4.35 (t, J=6.8 Hz, 2H), 4.09 (t, J=5.2 Hz, 1H), 3.75 (q, J=4.8 Hz, 1H), 3.57 (m, 1H), 3.42 (m, 3H), 1.72 (m, 2H), 1.50 (m, 2H).

EXAMPLE 28

(5-Amino-2-oxo-3-β-D-ribofuranosyl-2,3-dihydrothiazolo[4,5-d]pyrimidin-7-yloxymethyl)-ethyl-carbamic acid ethyl ester (58)

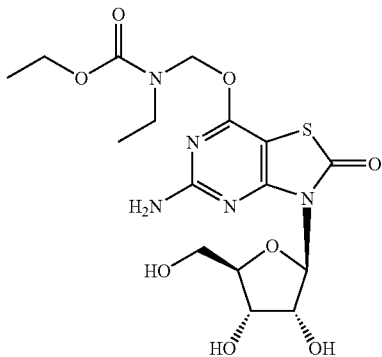

Step 1: Preparation of N-ethyl-N-(hydroxymethyl)urethane (56)

Under general experimental conditions reported by Kelper, *JOC*, 52, 453-55 (1987), a slurry of Ba(OH)$_2$ (46.0 mg, 266 μmol) in water (480 μL) was added to a mixture of N-ethylurethane (2.04 mL, 17.1 mmol) and a 37% aqueous solution of formalin (1.28 mL, 17.1 mmol) in one portion with stirring. The mixture became cool and gradually formed a cloudy solution. The mixture was stirred at room temperature and the disappearance of N-ethylurethane monitored by TLC analysis. After 2 h, the reaction was quenched by adding solid CO$_2$, stirred for 30 minutes and filtered to remove the precipitated barium carbonate. The solvent was removed under vacuum to provide an oily residue. The trace amounts of water were removed by azeotropic distillation with benzene (3×100 mL) to provide 56 as a clear oil (2.50 g, quant.): $^1$H NMR (400 MHz, CDCl$_3$) δ 4.88 (d, J=7.6 Hz, 1H), 4.79 (d, J=7.6 Hz, 2H), 4.18 (q, J=7.6 Hz, 2H), 3.40 (q, J=6.4 Hz, 2H), 1.30 (t, J=7.6 Hz, 3H), 1.19 (t, J=7.6 Hz, 3H).

Step 2: Preparation of 5-Acetylamino-3-(2',3',5'-tri-O-acetyl-β-D-ribofuranosyl)-2,3-dihydro-thiazolo[4,5-d]pyrimidin-7-yloxymethyl)-ethyl-carbamic acid ethyl ester (57)

In a manner similar to Example 13, step 2, compound 57 was prepared from 16 and 56 as a white solid in 24% yield: R$_f$=0.4 (33% EtOAc—CHCl$_3$); $^1$H NMR (400 MHz, CDCl$_3$) δ 11.49 (br s, 1H), 6.08 (d, J=4.0 Hz, 1H), 5.75 (t, J=6.0 Hz, 1H), 5.53 (s, 2H), 4.49 (dd, J=13.5, 8.4 Hz, 1H), 4.30 (m, 5H), 3.62 (q, J=7.2 Hz, 2H), 2.30 (s, 3H), 2.12 (s, 3H), 2.09 (s, 3H), 2.08 (s, 3H), 1.36 (t, J=6.8 Hz, 3H), 1.20 (t, J=6.8 Hz, 3H); [M+H]$^+$ 614.2.

Step 3: Preparation of (5-Amino-2-oxo-3-β-D-ribofuranosyl-2,3-dihydro-thiazolo[4,5-d]pyrimidin-7-yloxymethyl)-ethyl-carbamic acid ethyl ester (58)

In a manner similar to Example 13, step 3, the title compound was prepared from 57 as a white solid in 30% yield: $^1$H NMR (400 MHz, d$_6$-DMSO) δ 7.89 (br s, 2H), 5.82 (d, J=4.8 Hz, 1H), 5.49 (m, 3H), 5.32 (d, J=5.2 Hz, 1H), 5.01 (d, J=5.6 Hz, 1H), 4.82 (q, J=5.6 Hz, 1H), 4.69 (t, J=5.6 Hz, 1H), 4.20 (q, J=7.2 Hz, 2H), 4.11 (q, J=5.6 Hz, 2H), 3.78 (q, J=5.2 Hz, 1H), 3.60 (m, 1H), 3.45 (m, 1H), 1.27 (t, J=7.2 Hz, 3H), 1.09 (t, J=6.0 Hz, 3H); [M+H]$^+$ 446.3.

EXAMPLE 29

(5-Amino-2-oxo-3-β-D-ribofuranosyl-2,3-dihydro-thiazolo[4,5-d]pyrimidin-7-yloxymethyl)-methyl-carbamic acid ethyl ester (61)

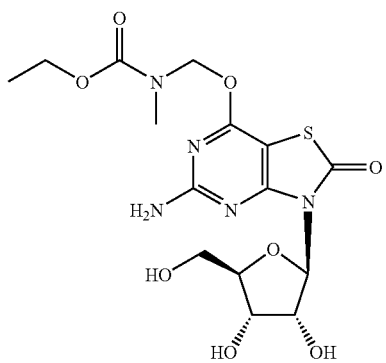

Step 1: Preparation of N-methyl-N-(hydroxymethyl)urethane (59)

In a manner similar to Example 28, step 1, compound 59 was prepared from N-methylurethane and formalin as a thick oil in quantitative yield: $^1$H NMR (400 MHz, CDCl$_3$) δ 5.02 (d, J=7.6 Hz, 1H), 4.79 (d, J=7.6 Hz, 2H), 4.18 (q, J=4.4 Hz, 2H), 3.01 (s, 3H), 1.30 (t, J=7.6 Hz, 3H).

Step 2: Preparation of (5-Amino-2-oxo-3-(2',3',5'-tri-O-acetyl-β-D-ribofuranosyl)-2,3-dihydro-thiazolo[4,5-d]pyrimidin-7-yloxymethyl)-methyl-carbamic acid ethyl ester (60)

In a manner similar to Example 13, step 2, compound 60 was prepared from 16 and 59 as a white solid in 24% yield: R$_f$=0.4 (33% EtOAc—CHCl$_3$); $^1$H NMR (400 MHz, CDCl$_3$) δ 11.49 (br s, 1H), 6.08 (d, J=4.0 Hz, 1H), 5.75 (t, J=6.0 Hz, 1H), 5.53 (s, 2H), 4.49 (dd, J=13.5, 8.4 Hz, 1H), 4.30 (m, 5H), 3.62 (q, J=7.2 Hz, 2H), 2.30 (s, 3H), 2.12 (s, 3H), 2.09 (s, 3H), 2.08 (s, 3H), 1.36 (t, J=6.8 Hz, 3H), 1.20 (t, J=6.8 Hz, 3H); [M+H]$^+$ 614.2.

Step 3: Preparation of (5-Amino-2-oxo-3-β-D-ribofuranosyl-2,3-dihydro-thiazolo[4,5-d]pyrimidin-7-yloxymethyl)-methyl-carbamic acid ethyl ester (61)

In a manner similar to Example 13, step 3, the title compound was prepared from 60 as a white solid in 20% yield: $^1$H NMR (400 MHz, d$_6$-DMSO) δ 7.86 (br s, 2H), 5.82 (d, J=4.8 Hz, 1H), 5.47 (s, 2H), 5.31 (d, J=5.2 Hz, 1H), 5.00 (d, J=5.6 Hz, 1H), 4.82 (q, J=5.2 Hz, 1H), 4.67 (q, J=5.6 Hz, 1H), 4.18 (q, J=6.4 Hz, 2H), 4.12 (m, 1H), 3.78 (q, J=6.0 Hz, 1H), 3.60 (m, 1H), 3.47 (m, 1H), 3.30 (s, 3H), 1.27 (t, J=6.8 Hz, 3H); [M+H]$^+$ 432.3.

EXAMPLE 30

5-Amino-7-cyclopropylmethoxy-3-β-D-ribofuranosyl-thiazolo[4,5-d]pyrimidin-2-one (63)

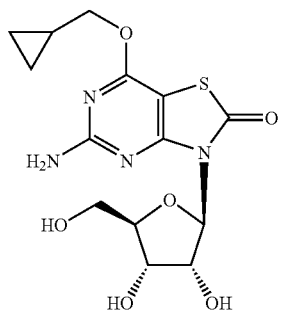

Step 1: Preparation of 5-Amino-3-(2',3',5'-tri-O-acetyl-β-D-ribofuranosyl)-3H-thiazolo[4,5-d]pyrimidin-2,7-dione (25)

To a suspension of 1 (5.00 g, 15.8 mmol) in acetonitrile (160 mL) at 0° C. was added successively Et$_3$N (11.0 mL, 79.0 mmol), DMAP (195 mg, 1.59 mmol), and Ac$_2$O (4.47 mL, 47.4 mmol). The reaction mixture was stirred at room temperature for 2 h, whereupon it was concentrated to a brown syrup. The residue was purified by flash column chromatography (silica, MeOH/CHCl$_3$=1-10%) to afford 6.22 g (89%) of triacetate 25 as a white solid: mp 198-199° C.; $^1$H (400 MHz, d$_6$-DMSO) δ 11.34 (s, 1H), 7.02 (br s, 2H), 5.90 (m, 2H), 5.51 (t, J=6.0 Hz, 1H), 4.36 (dd, J=12.4, 3.2 Hz, 1H), 4.21 (m, 1H), 4.08 (q, J=6.0 Hz, 1H), 2.06 (s, 3H), 2.06 (s, 3H), 2.00 (s, 3H); MS (+)-ES [M+H]$^+$ m/z 443.3.

Step 2: Preparation of 5-Amino-7-cyclopropyl-methoxy-3-(2',3',5'-tri-O-acetyl-β-D-ribofuranosyl)-thiazolo[4,5-d]pyrimidin-2-one (62)

To a heterogeneous mixture of the above triacetate 25 (1.49 g, 3.37 mmol), Argonaut polymer supported-triphenylphosphine resin (5.98 g, 10.1 mmol), and cyclopropylmethyl carbinol (546 uL, 6.74 mmol) in THF (70 mL) at 0° C. was added DEAD (742 uL, 4.72 mmol). The reaction mixture was warmed to room temperature, stirred 16 h, then filtered through a short pad of SiO$_2$. The concentrated filtrate was chromatographed (SiO$_2$, gradient elution, 0-5% EtOAc—CHCl$_3$), affording 680 mg (42%) of a white solid: $^1$H (400 MHz, d$_6$-DMSO) δ 6.95 (s, 2H), 5.99 (d, J=4.0 Hz, 1H), 5.91 (dd, J=6.2, 4.0 Hz, 1H), 5.55 (dd, J=6.6, 6.2 Hz, 1H), 4.37 (dd, J=12.1, 3.7 Hz, 1H), 4.22-4.26 (m, 1H), 4.19 (d, J=7.0 Hz, 2H), 4.09 (dd, J=11.7, 5.9 Hz, 1H), 2.07 (s, 3H), 2.06 (s, 3H), 1.99 (s, 3H), 1.20-1.26 (m, 1H), 0.53-0.58 (m, 2H), 0.31-0.35 (m, 2H); MS (+)-ES [M+H]$^+$ m/z 497. Elemental Analysis calc'd for C$_{20}$H$_{24}$N$_4$O$_9$S: C, 48.38; H, 4.87; N, 11.28; S, 6.46. Found: C, 48.53; H, 4.99; N, 11.27; S, 6.18.

Step 3: Preparation of 5-Amino-7-cyclopropyl-methoxy-3-β-D-ribofuranosyl-thiazolo[4,5-d]pyrimidin-2-one (63)

To a suspension of 62 (570 mg, 1.18 mmol) in MeOH was added K$_2$CO$_3$ (50 mg, 0.36 mmol) at room temperature. The reaction mixture was stirred 1 h, concentrated, partitioned between 20% IPA-CHCl$_3$ and water, and then triturated with Et$_2$O to afford 128 mg (29%) of 63 as a white solid: $^1$H (400 MHz, d$_6$-DMSO) δ 6.86 (s, 2H), 5.85 (d, J=5.1 Hz, 1H), 5.27 (d, J=5.5 Hz, 1H), 4.96 (d, J=5.5 Hz, 1H), 4.77 (q, J=5.5 Hz, 1H), 4.66 (t, J=5.9 Hz, 1H), 4.18 (dd, J=7.3, 1.1 Hz, 1H), 4.09 (q, J=5.5 Hz, 1H), 3.75 (q, J=5.1 Hz, 1H), 3.39-3.60 (m, 2H), 1.20-1.27 (m, 1H), 0.53-0.57 (m, 2H), 0.31-0.34 (m, 2H); MS (+)-ES [M+H]$^+$ m/z 371. Elemental Analysis calc'd for C$_{14}$H$_{18}$N$_4$O$_6$S: C, 45.40; H, 4.90; N, 15.13; S, 8.66. Found: C, 44.98; H, 4.92; N, 14.92; S, 8.49.

EXAMPLE 31

5-Amino-7-(3-phenyl-allyloxy)-3-β-D-ribofuranosyl-thiazolo[4,5-d]pyrimidin-2-one (66)

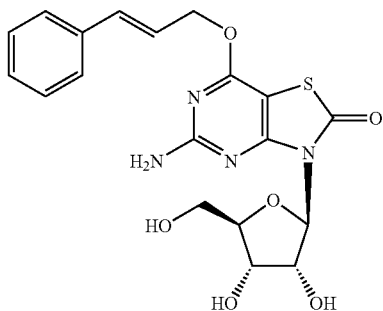

Step 1: Preparation of 5-Amino-7-(3-phenyl-allyloxy)-3-(2',3',5'-tri-O-acetyl-β-D-ribofuranosyl)-thiazolo[4,5-d]pyrimidin-2-one (64)

In a manner similar to Step 2 of Example 25, compound 64 was prepared from 25 and cinnamyl alcohol in a 69% yield: MS (+)-ES [M+H]$^+$ m/z 601.

Step 2: Preparation of 5-Amino-7-(3-phenyl-allyloxy)-3-β-D-ribofuranosyl-thiazolo[4,5-d]pyrimidin-2-one (65)

In a manner similar to Steps 3 of Example 25, the title compound was prepared from 64 in a 19% yield as a white solid: $^1$H (400 MHz, d$_6$-DMSO) δ 7.46 (d, J=7.0 Hz, 1H), 7.34 (t, J=7.3 Hz, 1H), 7.23-7.27 (m, 1H), 6.93 (s, 2H), 6.74 (d, J=16.1 Hz, 1H), 6.45-6.53 (m, 1H), 5.86 (d, J=5.1 Hz, 1H), 5.28 (d, J=5.5 Hz, 1H), 5.04 (d, J=6.2 Hz, 1H), 4.96 (d, J=5.5 Hz, 1H), 4.79 (q, J=5.5 Hz, 1H), 4.67 (t, J=5.5 Hz, H), 4.09 (q, J=5.1 Hz, 1H), 3.76 (q, J=4.8 Hz, 1H), 3.30-3.60 (m, 2H); MS (+)-ES [M+H]$^+$ m/z 433. Elemental Analysis calc'd for C$_{19}$H$_{20}$N$_4$O$_6$S: C, 52.77; H, 4.66; N, 12.96; S, 7.41. Found: C, 52.28; H, 4.66; N, 12.66; S, 7.27.

EXAMPLE 32

5-Amino-7-(5-methyl-2-oxo-[1,3]dioxol-4-yl-methoxy)-3-(2',3',5'-tri-O-acetyl-β-D-ribofuranosyl)-thiazolo[4,5-d]pyrimidin-2-one (66)

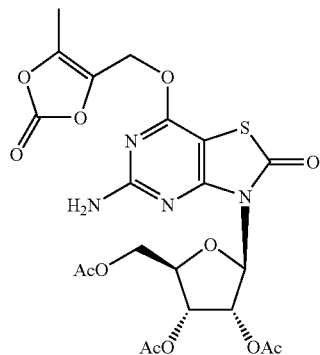

To a solution of triacetate 25 (1.55 g, 3.50 mmol) in THF (50 mL) at 0° C. was added polymer supported-triphenylphosphine (4.95 g, 10.50 mmol, Argonaut). To this mixture was added 4-hydroxymethyl-5-methyl-[1,3]dioxol-2-one (0.91 g, 7.00 mmol), prepared according to the procedure of Alepegiani, Syn. Comm., 22(9), 1277-82 (1992) Diethyl azodicarboxylate (0.73 ml, 4.60 mmol) was then added dropwise. The resulting mixture was stirred at room temperature for 48 h, filtered and washed with MeOH and CHCl$_3$. The filtrate was concentrated and purified by flash column chromatography (silica, acetone/CHCl$_3$=10-20%) to afford dioxolone derivative 66 (1.38 g, 71%) as white solid: $^1$H (400 MHz, d$_6$-DMSO) 66; δ 7.06 (s, 2H), 6.00 (d, J=4.0 Hz, 1H), 5.92 (dd, J=6.6, 4.4 Hz, 1H), 5.56 (t, J=6.4 Hz, 1H), 5.30 (s, 2H), 4.38 (dd, J=11.6, 3.6 Hz, 1H), 4.25 (t, J=3.6 Hz, 1H), 4.10 (q, J=6.0 Hz, 1H), 2.23 (s, 3H), 2.08 (s, 3H), 2.07 (s, 3H), 2.00 (s, 3H); MS (+)-ES [M+H]$^+$ m/z 555.3. Elemental Analysis calc'd for C$_{21}$H$_{22}$N$_4$O$_{12}$S.Me$_2$CO: C, 47.06; H, 4.61; N, 9.15; S, 5.23. Found: C, 47.25; H, 4.37; N, 9.53; S, 5.52.

EXAMPLE 33

(5-Amino-2-oxo-3-β-D-ribofuranosyl-2,3-dihydro-thiazolo[4,5-d]pyrimidin-7-yloxymethyl)-carbamic acid ethyl ester (68)

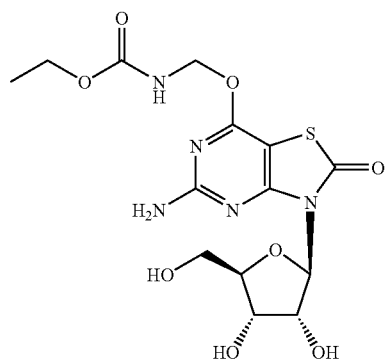

Step 1: Preparation of 5-Amino-3-(2',3',5'-tris-O-triethylsilanyl-β-D-ribofuranosyl)-thiazolo[4,5-d]pyrimidin-2,7-dione (26)

To a suspension of 1 (1.00 g, 3.16 mmol) in DMF (20 mL) at room temperature was added successively imidazole (753 mg, 11.06 mmol), DMAP (39 mg, 0.32 mmol), and chlorotriethylsilane (1.64 mL, 9.80 mmol). The reaction mixture was stirred at room temperature for 2 h, whereupon it was quenched by saturated $NaHCO_3$ solution (20 mL). The mixture was extracted with $CHCl_3$ (3×20 mL), dried over $MgSO_4$ and concentrated. The residue was purified by flash column chromatography (silica, $MeOH/CHCl_3$=1-5%) to afford 1.91 g (92%) of compound 26 as a white solid: $^1H$ (400 MHz, $d_6$-DMSO) δ 5.99 (s, 1H), 5.62 (br s, 2H), 5.19 (dd, J=4.4, 6.0 Hz, 1H), 4.35 (dd, J=2.8, 4.4 Hz, 1H), 3.99 (m, 1H), 3.77 (dd, J=7.6, 10.8 Hz, 1H), 3.68 (dd, J=4.8, 10.4 Hz, 1H), 1.10 (t, J=7.1 Hz, 3H), 0.96 (t, J=7.1 Hz, 3H), 0.89 (t, J=7.1 Hz, 3H), 0.68 (q, J=7.1 Hz, 2H), 0.61 (q, J=7.1 Hz, 2H), 0.54 (m, 2H); MS (+)-ES $[M+H]^+$ m/z 660.0.

Step 2: Preparation of 5-Amino-3-(2',3',5'-tris-O-triethylsilanyl-β-D-ribofuranosyl)-2,3-dihydro-thiazolo[4,5-d]pyrimidin-7-yloxymethyl)-carbamic acid ethyl ester (67)

In a manner similar to Step 2 of Example 13, compound 67 was prepared from 26 and N-ethylurethane as a white solid in 31% yield: $[M+H]^+$ 760.5; $^1H$ NMR (400 MHz, $CDCl_3$) δ 6.43 (br s, 2H), 6.09 (t, J=7.6 Hz, 1H), 5.94 (d, J=6.0 Hz, 1H), 5.31 (d, J=4.8 Hz, 2H), 5.19 (dd, J=6.0, 4.8 Hz, 1H), 4.35 (dd, J=4.8, 2.8 Hz, 1H), 4.19 (q, J=6.4 Hz, 2H), 3.98 (m, 1H), 3.76 (dd, J=10.8, 7.6 Hz, 1H), 3.68 (dd, J=10.4, 4.8 Hz, 1H), 1.29 (t, J=6.8 Hz, 3H), 1.02 (t, J=8.0 Hz, 3H), 0.96 (t, J=7.6 Hz, 3H), 0.90 (t, J=8.0 Hz, 3H), 0.69 (q, J=8.0 Hz, 2H), 0.61 (q, J=8.0 Hz, 2H), 0.55 (m, 2H); $[M+H]^+$ 760.5.

Step 3: Preparation of (5-Amino-2-oxo-3-β-D-ribofuranosyl-2,3-dihydro-thiazolo[4,5-d]pyrimidin-7-yloxymethyl)-carbamic acid ethyl ester (68)

A solution of 67 (244 mg, 321 µmol), 5M HF in pyridine (321 µL, 1.60 mmol) and THF (3.20 mL) were stirred at room temperature for 5 h. Removal of the solvents under vacuum left a residue that was purified by flash chromatography ($SiO_2$, 10% MeOH—$CHCl_3$) to afford 68 (119 mg, 90%) as a white solid: $^1H$ NMR (400 MHz, $d_6$-DMSO) δ 8.43 (br s, 1H), 7.76 (br s, 2H), 5.82 (d, J=5.2 Hz, 1H), 5.78 (s, 2H), 5.32 (d, J=5.6 Hz, 1H), 5.24 (dd, J=6.0, 4.8 Hz, 1H), 5.00 (d, J=5.6 Hz, 1H), 4.82 (q, J=5.6 Hz, 1H), 4.68 (t, J=6.0 Hz, 1H), 4.11 (q, J=5.2 Hz, 1H), 4.09 (q, J=7.2 Hz, 2H), 3.78 (q, J=5.6 Hz, 1H), 3.60 (m, 1H), 3.46 (m, 1H), 1.21 (t, J=7.2 Hz, 3H); $[M+H]^+$ 418.2.

EXAMPLE 34

5-Amino-7-(5-methyl-2-oxo-[1,3]dioxol-4-ylmethoxy)-3-β-D-ribofuranosyl-thiazolo[4,5-d]pyrimidin-2-one (70)

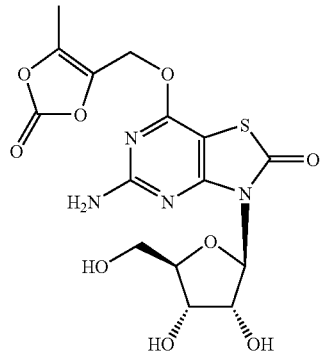

Step 1: Preparation of 5-Amino-7-(5-methyl-2-oxo-[1,3]dioxol-4-ylmethoxy)-3-(2',3',5'-tris-O-triethylsilanyl-β-D-ribofuranosyl)-thiazolo[4,5-d]pyrimidin-2-one (69)

In a manner similar to Example 32, compound 69 was prepared from 26 and 4-hydroxymethyl-5-methyl-[1,3]dioxol-2-one as a white solid in 45% yield: $^1H$ NMR (400 MHz, $CDCl_3$) δ 6.06 (d, J=6.0 Hz, 1H), 5.21 (dd, J=6.0, 4.8 Hz, 1H), 5.18 (d, J=3.2 Hz, 2H), 4.94 (br s, 2H), 4.38 (dd, J=4.8, 2.8 Hz, 1H), 4.00 (m, 1H), 3.79 (dd, J=11.2, 8.0 Hz, 1H), 3.69 (dd, J=10.8, 5.2 Hz, 1H), 2.23 (s, 3H), 1.02 (t, J=8.0 Hz, 3H), 0.96 (t, J=7.6 Hz, 3H), 0.89 (t, J=8.4 Hz, 3H), 0.70 (q, J=7.6 Hz, 2H), 0.61 (q, J=8.0 Hz, 2H), 0.53 (m, 2H); $[M+H]^+$ 771.5.

Step 2: Preparation of 5-Amino-7-(5-methyl-2-oxo-[1,3]dioxol-4-ylmethoxy)-3-β-D-ribofuranosyl-thiazolo[4,5-d]pyrimidin-2-one (70)

In a manner similar to Steps 3 of Example 33, the title compound was prepared from 69 as a white solid in 89% yield: $^1H$ NMR (400 MHz, $d_6$-DMSO) δ 7.03 (br s, 2H), 5.90 (d, J=5.2 Hz, 1H), 5.33 (s, 2H), 5.02 (d, J=4.8 Hz, 1H), 4.83 (q, J=5.6 Hz, 1H), 4.71 (t, J=6.0 Hz, 1H), 4.14 (q, J=5.2 Hz, 1H), 3.80 (q, J=4.8 Hz, 1H), 3.62 (m, 1H), 3.47 (m, 1H), 2.27 (s, 3H); $[M+H]^+$ 429.2.

EXAMPLE 35

4-(5-Amino-2-oxo-3-β-D-ribofuranosyl-thiazolo[4,5-d]pyrimidin-7-yloxy)-butyric acid tert-butyl ester (72)

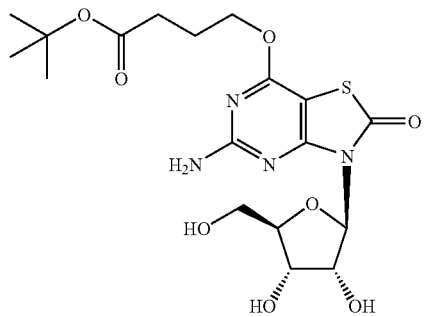

Step 1: Preparation of 4-(5-Amino-2-oxo-3-(2',3',5'-tris-O-triethylsilanyl-β-D-ribofuranosyl)-thiazolo[4,5-d]pyrimidin-7-yloxy)-butyric acid tert-butyl-ester (71)

In a manner similar to Step 2 of Example 13, compound 71 was prepared from 26 and 4-hydroxy-butyric acid tert-butyl-ester (Lui, *JOC,* 68(17), 6679-6684 (2003)) as a white solid in 92% yield: $^1$H NMR (400 MHz, CDCl$_3$) δ 6.06 (d, J=6.4 Hz, 1H), 5.22 (dd, J=6.0, 4.8 Hz, 1H), 4.98 (br s, 2H), 4.42 (t, J=6.0 Hz, 2H), 4.38 (dd, J=6.0, 4.8 Hz, 1H), 4.00 (m, 1H), 3.80 (dd, J=10.8, 7.6 Hz, 1H), 3.69 (dd, J=10.8, 5.2 Hz, 1H), 2.38 (t, J=7.2 Hz, 2H), 2.06 (quint, J=7.2 Hz, 3H), 1.47 (s, 9H), 1.02 (t, J=8.0 Hz, 3H), 0.96 (t, J=8.0 Hz, 3H), 0.88 (t, J=8.0 Hz, 3H), 0.70 (q, J=7.6 Hz, 2H), 0.61 (q, J=8.0 Hz, 2H), 0.53 (m, 2H); [M+H]$^+$ 801.5.

Step 2: Preparation of 4-(5-Amino-2-oxo-3-β-D-ribofuranosyl-thiazolo[4,5-d]pyrimidin-7-yloxy)-butyric acid tert-butyl-ester (72)

In a manner similar to Steps 3 of Example 33, the title compound was prepared from 71 as a white solid in 66% yield: $^1$H NMR (400 MHz, d$_6$-DMSO) δ 6.93 (br s, 2H), 5.90 (d, J=4.8 Hz, 1H), 5.32 (d, J=5.6 Hz, 1H), 5.10 (d, J=5.6 Hz, 1H), 4.83 (q, J=5.6 Hz, 1H), 4.71 (t, J=5.6 Hz, 1H), 4.38 (t, J=6.4 Hz, 2H), 4.13 (q, J=5.6 Hz, 1H), 3.80 (q, J=5.6 Hz, 1H), 3.62 (m, 1H), 3.47 (m, 1H), 2.35 (t, J=7.6 Hz, 2H), 1.96 (quint, J=6.8 Hz, 2H), 1.44 (s, 9H); [M+H]$^+$ 459.3.

EXAMPLE 36

5-Amino-7-(4-acetoxy-1-butoxy)-3-β-D-ribofuranosyl-thiazolo-[4,5-d]pyrimidin-2-one (74)

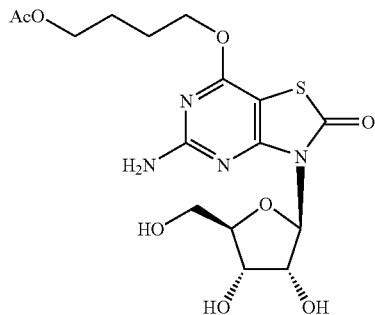

Step 1: Preparation of 5-amino-7-(4-acetoxy-1-butoxy)-3-(2',3',5'-tris-O-triethylsilanyl-β-D-ribofuranosyl)-thiazolo[4,5-d]pyrimidin-2-one (73)

In a manner similar to Example 13, step 2, 73 was prepared was prepared from 26 and 1,4-butanediol monoacetate as a white solid in 81% yield: $^1$H NMR (400 MHz, CDCl$_3$) δ 6.06 (d, J=6.0 Hz, 1H), 5.23 (dd, J=5.6, 5.2 Hz, 1H), 4.93 (br s, 2H), 4.41 (t, J=6.4 Hz, 2H), 4.37 (dd, J=4.8, 2.8 Hz, 1H), 4.14 (t, J=6.4 Hz, 2H), 4.00 (m, 1H), 3.80 (dd, J=11.2, 7.6 Hz, 1H), 3.69 (dd, J=10.8, 4.8 Hz, 1H), 2.07 (s, 3H), 1.85 (m, 2H), 1.78 (m, 2H), 1.02 (t, J=7.6 Hz, 3H), 0.96 (t, J=8.0 Hz, 3H), 0.88 (t, J=7.6 Hz, 3H), 0.70 (q, J=7.6 Hz, 2H), 0.61 (q, J=8.0 Hz, 2H), 0.56 (m, 2H); [M+H]$^+$ 773.5.

Step 2: Preparation of 5-amino-7-(4-acetoxy-1-butoxy)-3-β-D-ribofuranosyl-thiazolo[4,5-d]pyrimidin-2-one (74)

A solution of 73 (188 mg, 243 μmol) and 1M HF in acetonitrile (1.22 mL, 1.22 mmol) were stirred at room temperature for 18 h. Removal of the solvents under vacuum left a residue that was purified by flash chromatography (SiO$_2$, 10% MeOH—CHCl$_3$) to afford 74 (91.1 mg, 88%) as a white solid: $^1$H NMR (400 MHz, d$_6$-DMSO) δ 6.93 (br s, 2H), 5.90 (d, J=5.2 Hz, 1H), 5.32 (d, J=5.6 Hz, 1H), 5.01 (d, J=5.6 Hz, 1H), 4.83 (q, J=5.6 Hz, 1H), 4.71 (t, J=6.0 Hz, 1H), 4.41 (t, J=6.0 Hz, 2H), 4.14 (q, J=4.8 Hz, 1H), 4.07 (t, J=6.4 Hz, 1H), 3.80 (q, J=6.0 Hz, 1H), 3.62 (m, 1H), 3.47 (m, 1H), 2.04 (s, 3H), 1.80 (m, 2H), 1.71 (m, 2H); [M+H]$^+$ 431.3.

EXAMPLE 37

5-Amino-7-(4-acetoxy-1-propoxy)-3-β-D-ribofuranosyl-thiazolo-[4,5-d]pyrimidin-2-one (76)

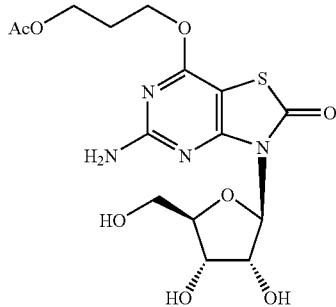

Step 1: Preparation of 5-amino-7-(4-acetoxy-1-propoxy)-3-(2',3',5'-tris-O-triethylsilanyl-β-D-ribofuranosyl)-thiazolo[4,5-d]pyrimidin-2-one (75)

In a manner similar to Example 13, step 2, 75 was prepared was prepared from 26 and 1,3-propanediol monoacetate as a white solid in 70% yield: $^1$H NMR (400 MHz, CDCl$_3$) δ 6.06 (d, J=6.4 Hz, 1H), 5.23 (dd, J=6.4, 4.8 Hz, 1H), 4.93 (br s, 2H), 4.46 (t, J=6.4 Hz, 2H), 4.38 (dd, J=4.4, 2.4 Hz, 1H), 4.22 (t, J=6.4 Hz, 2H), 4.00 (m, 1H), 3.80 (dd, J=10.8, 7.6 Hz, 1H), 3.69 (dd, J=10.8, 5.2 Hz, 1H), 2.12 (quint, J=6.4 Hz, 2H), 2.08 (s, 3H), 1.02 (t, J=8.0 Hz, 3H), 0.96 (t, J=8.0 Hz, 3H), 0.88 (t, J=8.0 Hz, 3H), 0.70 (q, J=8.4 Hz, 2H), 0.61 (q, J=8.4 Hz, 2H), 0.54 (m, 2H); [M+H]$^+$ 759.5.

Step 2: Preparation of 5-amino-7-(4-acetoxy-1-propoxy)-3-β-D-ribofuranosyl-thiazolo[4,5-d]pyrimidin-2-one (76)

In a manner similar to Example 36, step 2, 76 was prepared was prepared from 75 as a white solid in 92% yield: $^1$H NMR (400 MHz, d$_6$-DMSO) δ 6.94 (br s, 2H), 5.90 (d, J=5.2 Hz, 1H), 5.32 (d, J=4.8 Hz, 1H), 5.00 (d, J=4.8 Hz, 1H), 4.83 (q, J=4.8 Hz, 1H), 4.71 (t, J=6.0 Hz, 1H), 4.46 (t, J=6.4 Hz, 2H), 4.14 (t, J=6.4 Hz, 2H), 3.80 (q, J=5.2 Hz, 1H), 3.62 (dd, J=11.2, 8.0 Hz, 1H), 3.47 (dd, J=11.2, 6.0 Hz, 1H), 2.06 (quint, J=6.4 Hz, 2H), 2.04 (s, 3H); [M+H]$^+$ 417.2.

EXAMPLE 38

5-Amino-3-β-D-ribofuranosyl-3H-thiazolo-[4,5-d]pyrimidin-2-one (79)

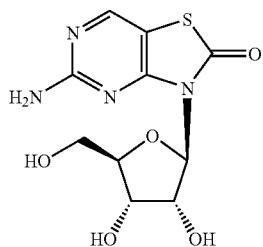

Step 1: Preparation of 5-Amino-7-thioxo-3-(2',3',5'-tri-O-acetyl-β-D-ribofuranosyl)-thiazolo[4,5-d]pyrimidin-2-one (77)

To a solution of 25 (1 g, 2.26 mmol) in pyridine (50 mL) was added at room temperature $P_2S_5$ (2.13 g, 4.79 mmol). The solution was refluxed gently (bath temperature 130-140° C.) for 29 h. The reaction mixture was evaporated to dryness in vacuo. The excess $P_2S_5$ was decomposed by the addition of $H_2O$ (40 mL) at 60° C. The mixture was stirred for 1 h at 60° C. and then cooled to room temperature. The mixture was extracted with $CHCl_3$ (3×40 mL). The dried ($MgSO_4$) organic layer was evaporated to yield a syrup, which was purified by flash column chromatography (silica, acetone/$CHCl_3$=15%) to afford 0.93 g (90%) of 77 as a yellow solid: $^1H$ (400 MHz, $d_6$-DMSO) δ 12.50 (s, 1H), 7.35 (br s, 2H), 5.89 (m, 2H), 5.51 (t, J=6.4 Hz, 1H), 4.36 (dd, J=12.0, 4.0 Hz, 1H), 4.24 (m, 1H), 4.10 (q, J=6.0 Hz, 1H), 2.07 (s, 3H), 2.06 (s, 3H), 2.01 (s, 3H); MS (+)-ES [M+H]$^+$ m/z 459.3.

Step 2: Preparation of 5-Amino-3-(2',3',5'-tri-O-acetyl-β-D-ribofuranosyl)-3H-thiazolo[4,5-d]pyrimidin-2-one (78)

A suspension of Raney® 2800 nickel (3 big spatula, prewashed with $H_2O$, MeOH and acetone) in acetone (50 mL) was stirred at refluxing for 1 h. Triacetate 77 (0.93 g, 2.03 mmol) was subsequently added into the above suspension at reflux. The mixture was stirred for 5 min, cooled to room temperature over 30 min. The reaction was quenched by bubbling $H_2S$ (g) into the mixture for 2 h. The resulting mixture was filtered through a short pad of Celite® and washed with EtOH. The filtrate was concentrated and purified by flash column chromatography (silica, MeOH/$CHCl_3$=1-2%) to afford 0.52 g (60%) of 78 as a white solid: mp 121-123° C.; $^1H$ (400 MHz, $d_6$-DMSO) δ 8.38 (s, 1H), 6.93 (s, 2H), 6.03 (d, J=3.6 Hz, 1H), 5.93 (dd, J=6.4, 3.6 Hz, 1H), 5.58 (t, J=6.0 Hz, 1H), 4.38 (dd, J=11.6, 3.6 Hz, 1H), 4.26 (m, 1H), 4.11 (q, J=6.0 Hz, 1H), 2.08 (s, 3H), 2.07 (s, 3H), 2.00 (s, 3H); MS (+)-ES [M+H]$^+$ m/z 427.2. Elemental Analysis calc'd for $C_{16}H_{18}N_4O_8S.0.5\ CH_3OH.0.25H_2O$: C, 44.34; H, 4.62; N, 12.54; S 7.17. Found: C, 44.54; H, 4.88; N, 12.16; S, 7.17.

Step 3: Preparation of 5-Amino-3-β-D-ribofuranosyl-3H-thiazolo[4,5-d]pyrimidin-2-one (79)

To a solution of 78 (0.52 g, 1.22 mmol) in MeOH (20 mL) was added $K_2CO_3$ (25 mg, 0.18 mmol). The reaction was stirred at room temperature overnight, then neutralized with AcOH (21 μL, 0.36 mmol). The resulting mixture was stirred at room temperature for additional 30 min, concentrated, and triturated with $H_2O$ (2 ml) to afford 0.33 g of compound 79 (89%) as a white solid: mp 220° C. (Dec); $^1H$ (400 MHz, $d_6$-DMSO) δ 8.34 (s, 1H), 6.85 (s, 2H), 5.90 (d, J=4.8 Hz, 1H), 5.31 (d, J=5.6 Hz, 1H), 4.98 (d, J=5.6 Hz, 1H), 4.81 (q, J=5.2 Hz, 1H), 4.67 (t, J=6.0 Hz, 1H), 4.11 (q, J=5.2 Hz, 1H), 3.77 (dd, J=10.8, 4.8 Hz, 3H), 358 (m, 1H), 3.44 (m, 1H); MS (+)-ES [M+H]$^+$ m/z 301.1. Elemental Analysis calc'd for $C_{10}H_{12}N_4O_5S.0.3H_2O$: C, 39.29; H, 4.15; N, 18.33; S10.49. Found: C, 39.51; H, 4.18; N, 17.95; S, 10.27.

EXAMPLE 39

5-Amino-3-β-D-ribofuranosyl-3H-thiazolo-[4,5-d]pyrimidin-2-one (79)

Alternative Synthetic Route A

Step 1: Preparation of 5-Amino-7-chloro-3-(2',3',5'-tri-O-acetyl-β-D-ribofuranosyl)-thiazolo[4,5-d]pyrimidin-2-one (80)

To a solution of 25 (0.84 g, 1.90 mmol) in $CHCl_3$ (9 mL) was added triethylamine (0.50 mL, 3.59 mmol) and $POCl_3$ (1.60 mL, 17.1 mmol). After heating at reflux for 16 h, the reaction mixture was cooled to room temperature and poured onto ice and sat. aq. $NaHCO_3$ (150 mL). The resulting mixture was extracted with $CH_2Cl_2$ (3×75 mL) and the combined organic layers dried ($MgSO_4$). Concentration followed by flash chromatography (9:1/$CH_2Cl_2$:EtOAc) afforded 708 mg (87%) of product as a white solid, m.p. 101-103° C. $^1H$ NMR (400 MHz, $CDCl_3$) δ 6.10 (d, J=2.8 Hz, 1H), 6.01 (dd, J=5.6, 3.2 Hz, 1H), 5.92 (t, J=6.0 Hz, 1H), 5.42 (s, 2), 4.97 (dd, J=11.6, 3.6 Hz, 1H), 4.32 (m, 1), 4.21 (dd, J=12.0, 5.2 Hz, 1H), 2.12 (s, 6H), 2.06 (s, 3H).

Step 2: Preparation of 5-Amino-3-(2',3',5'-tri-O-acetyl-β-D-ribofuranosyl)-3H-thiazolo[4,5-d]pyrimidin-2-one (78)

A flame-dried round bottom flask was charged with 80 (4.37 g, 9.48 mmol) and glacial acetic acid (61 mL). The flask was sealed with a septum and flushed with nitrogen. Zinc-copper couple (6.07 g, Aldrich) was added and the reaction stirred at room temperature for a period of 21 h. The reaction was then heated to 80° C. for 1 h. The reaction mixture was cooled to room temperature, filtered thru a pad of Celite®, washed with EtOAc (200 mL) and concentrated under vacuum. The resulting white solid (residue) was diluted with $CH_2Cl_2$ (250 mL) and washed with 0.5 M NaOH (500 mL). The aqueous layer was extracted with $CH_2Cl_2$ (2×150 mL) and the combined organic layers were dried ($MgSO_4$), filtered and concentrated. Purification by flash chromatography ($SiO_2$, 5% Acetone-$CH_2Cl_2$) afforded 78 (3.64 g, 90%) as a white powder identical in all respects to material isolated in Example 38, step 2.

Step 3: Preparation of 5-Amino-3-(2',3',5'-tri-O-acetyl-β-D-ribofuranosyl)-3H-thiazolo[4,5-d]pyrimidin-2-one (79)

The preparation of the title compound is described in Example 38, step 3.

EXAMPLE 40

5-Amino-3-β-D-ribofuranosyl-3H-thiazolo-[4,5-d]pyrimidin-2-one (79)

Alternative Synthetic Route B

Step 1: Preparation of 5-Acetylamino-7-chloro-3-(2',3',5'-tri-O-acetyl-β-D-ribofuranosyl)-thiazolo[4,5-d]pyrimidin-2-one (81)

Phosphorus oxychloride (6.42 mL, 70.2 mmol) was added dropwise to a solution of 16 (3.40 g, 7.02 mmol), triethylamine (1.96 mL, 14.04 mmol), and chloroform (14 mL) over 30 minutes at room temperature under nitrogen. The reaction mixture was then heated to 70° C. for 30 h. The mixture was cooled to ambient temperature, added dropwise over 2 h to a 0° C. solution of saturated aq. NaHCO$_3$ (500 mL), and stirred for an additional 1 h. The layers were separated, aqueous layer back extracted with methylene chloride (2×100 mL), combined organic layers were dried (MgSO$_4$), filtered and concentrated to a yellow solid. Purification was achieved via flash chromatography (SiO$_2$, 5% Acetone-CHCl$_3$) to afford 81 (3.17 g, 90%) as a white solid: $^1$H NMR (400 MHz, d$_6$-DMSO) δ 11.08 (s, 1H), 6.09 (d, J=4.0 Hz, 1H), 5.99 (dd, J=6.0, 4.0 Hz, 1H), 5.76 (t, J=6.8 Hz, 1H), 4.41 (dd, J=11.2, 3.2 Hz, 1H), 4.32 (td, J=7.2, 3.2 Hz, 1H), 4.24 (dd, J=11.6, 6.8 Hz, 1H), 2.18 (s, 3H), 2.12 (s, 3H), 2.11 (s, 3H), 2.03 (s, 3H); [M+H]$^+$ 503.3.

Step 2: Preparation of 5-Acetylamino-3-(2',3',5'-tri-O-acetyl-β-D-ribofuranosyl)-thiazolo[4,5-d]pyrimidin-2-one (82)

10% Palladium on carbon (862 mg) was added to a solution of 81 (2.07 mg, 4.12 mmol), sodium acetate (675 mg, 8.23 mmol) and absolute ethanol (100 mL) under nitrogen. The mixture was stirred under 250-300 psi H$_2$ (g) in a bomb for a period of 48 h. The mixture was filtered through Celite®, washed with ethyl acetate (200 mL), and concentrated to a yellow solid. The mixture was diluted with H$_2$O (200 mL) and extracted with CH$_2$Cl$_2$ (3×100 mL). The combined organic layers were dried (MgSO$_4$), filtered, and concentrated. The residue was purified via Flash chromatography (SiO$_2$, 10% Acetone-CHCl$_3$) to afford 82 (1.74 g, 90%) as a white powder: $^1$H NMR (400 MHz, d$_6$-DMSO) δ 10.78 (s, 1H), 8.82 (s, 1H), 6.10 (d, J=4.0 Hz, 1H), 6.04 (dd, J=6.0, 4.0 Hz, 1H), 5.77 (t, J=6.0 Hz, 1H), 4.41 (dd, J=11.6, 3.2 Hz, 1H), 4.30 (m, 1H), 4.23 (dd, J=12.0, 6.8 Hz, 1H), 2.20 (s, 3H), 2.12 (s, 3H), 2.10 (s, 3H), 2.03 (s, 3H); [M+H]$^+$ 469.4.

Step 3: Preparation of 5-Amino-3-β-D-ribofuranosyl-3H-thiazolo[4,5-d]pyrimidin-2-one (79)

In a manner similar to Example 13, step 3, the title compound was prepared from 82.

EXAMPLE 41

5-Amino-3-β-D-ribofuranosyl-3H-thiazolo-[4,5-d]pyrimidin-2-one (79)

Alternative Synthetic Route C

Step 1: Preparation of N'-(7-Chloro-2-oxo-3-(2',3',5'-tri-O-acetyl-β-D-ribofuranosyl)-2,3-dihydro-thiazolo[4,5-d]pyrimidin-5-yl)-N,N-dimethyl-formamidine (83a)

Thionyl chloride (2.58 mL, 35.4 mmol) was added dropwise over 1 h to a mixture of 16 (500 mg, 1.03 mmol) and DMF (1.29 mL, 16.7 mmol) in CHCl$_3$ (28 mL) at room temperature under N$_2$. The reaction mixture was heated to 60° C. for a period of 23 h. The mixture was carefully poured into an ice-cold sat. NaHCO$_3$ solution and stirred for 30 minutes. The layers were separated, the aqueous layer extracted with CH$_2$Cl$_2$ (2×80 mL) and the combined organic layers were dried over MgSO$_4$, filtered and concentrated to afford 83a (519 mg, quant.) as a white foam: $^1$H NMR (400 MHz, d$_6$-DMSO) δ 8.65 (s, 1H), 6.14 (d, J=4.0 Hz, 1H), 5.97 (dd, J=6.4, 3.6 Hz, 1H), 5.62 (t, J=6.8 Hz, 1H), 4.43 (dd, J=12.0, 3.6 Hz, 1H), 4.32 (m, 1H), 4.16 (dd, J=12.0, 5.2 Hz, 1H), 3.23 (s, 3H), 3.11 (s, 3H), 2.13 (s, 3H), 2.12 (s, 3H), 2.02 (s, 3H); [M+H]$^+$ 516.1.

Step 1a: Preparation of N'-(7-Bromo-2-oxo-3-(2',3',5'-tri-O-acetyl-β-D-ribofuranosyl)-2,3-dihydro-thiazolo[4,5-d]pyrimidin-5-yl)-N,N-dimethyl-formamidine (83b)

Thionyl bromide (11.2 mL, 145 mmol) was added dropwise over 1 h to a mixture of 16 (2.34 g, 4.83 mmol), DMF (5.61 mL, 72.5 mmol), CHCl$_3$ (50 mL), and toluene (55 mL) at room temperature under N$_2$. The reaction mixture was heated to 110° C. for a period of 20 h. The mixture was carefully poured into an ice-cold sat. NaHCO$_3$ solution and stirred for 1 h. The layers were separated, the aqueous layer extracted with CH$_2$Cl$_2$ (2×80 mL) and the combined organic layers were dried over MgSO$_4$, filtered and concentrated to a yellow residue. The product was purified by flash chromatography (SiO$_2$, 20% Acetone-CHCl$_3$) to afford 83b (1.53 g, 57%) as a white foam: $^1$H NMR (400 MHz, d$_6$-DMSO) δ 8.64 (s, 1H), 6.12 (d, J=3.2 Hz, 1H), 5.96 (dd, J=6.4, 3.2 Hz, 1H), 5.61 (t, J=6.8 Hz, 1H), 4.42 (dd, J=8.8, 3.2 Hz, 1H), 4.31 (m, 1H), 4.16 (dd, J=12.4, 5.6 Hz, 1H), 3.23 (s, 3H), 3.11 (s, 3H), 2.13 (s, 3H), 2.12 (s, 3H), 2.02 (s, 3H); [M+H]$^+$ 560.2.

Step 2: Preparation of 5-Amino-3-(2',3',5'-tri-O-acetyl-β-D-ribofuranosyl)-3H-thiazolo[4,5-d]pyrimidin-2-one (78)

A flame-dried round bottom flask was charged with 83a (1.08 g, 2.11 mmol) and glacial acetic acid (21 mL). The flask was sealed with a septum and flushed with nitrogen. Zinc dust (1.38 g, 21.1 mmol) was added and the reaction heated to 80° C. for 48 h. The reaction mixture was cooled to room temperature, filtered thru a pad of Celite®, washed with EtOAc (100 mL) and concentrated under vacuum. The resulting white solid (residue) was diluted with CH$_2$Cl$_2$ (100 mL) and washed with sat. aqueous NaHCO$_3$ (500 mL). The aqueous layer was extracted with CH$_2$Cl$_2$ (2×50 mL) and the combined organic layers were dried (MgSO$_4$), filtered and concentrated. Purification by flash chromatography (SiO$_2$, 5% Acetone-CH$_2$Cl$_2$) afforded 78 (464 mg, 52%) as a white powder identical in all respects to material isolated in Example 38, step 2.

Step 3: Preparation of 5-Amino-3-(2',3',5'-tri-O-acetyl-β-D-ribofuranosyl)-3H-thiazolo[4,5-d]pyrimidin-2-one (79)

The preparation of the title compound is described in Example 38, step 3.

EXAMPLE 42

5-Amino-3-β-D-ribofuranosyl-3H-thiazolo-[4,5-d]pyrimidin-2-one (79)

Alternative Synthetic Route D

Step 1: Preparation of 4-Chloro-2-oxo-2,3-dihydro-thiazole-5-carbaldehyde(85)

Compound 85, originally synthesized by Baranov, et al, *Chem. Het. Compounds* (Engl. Trsl.), 1975, 11, p. 73 was prepared using a modification of the procedure reported. Commercially available 2,4-thiazolidinedione 84 (25.0 g, 213 mmol) was suspended in POCl$_3$ (59 ml, 641 mmol) cooled to 0° C. with an ice bath to cool. DMF (24.8 mL, 320 mmol) was added drop wise to the reaction over 15 min. The reaction was heated to 90° C. for 2 h then at 115° C. for 20 min. After 20 minutes, the reaction was cooled to 90° C. and maintained for an additional hour. After 1 h the mixture was heated to 115° C. for 15 min. The hot reaction mixture was poured into 1 L of water with vigorously stirring. After 10 min the mixture is filtered. The aqueous phase was extracted 5 times with ethyl ether (600 mL) and the organic phase was separated and concentrated under vacuum. The solid residue was dissolved in a minimum volume of aq. sat. NaHCO$_3$. The mixture was carefully acidified with 6M HCl to pH=2, whereupon a precipitate forms after about 30 min. Filtration yields 20.9 gm of compound 85 in 62% yield: R$_f$=0.3 (2% H$_2$O, 8% Methanol, 90% Ethyl acetate); $^1$H NMR (400 MHz, CDCl$_3$) δ 9.79 (s, 1H), 8.95 (s, 1H); MS (+)-ES [M+H]$^+$ 164.

Step 2: Preparation of 5-Amino-3H-thiazol[4,5-d]pyrimidin-2-one (86)

Compound 85 (1.22 g, 7.47 mmol), guanidine hydrochloride (2.13 g, 22.4 mmol), K$_2$CO$_3$ (1.03 g, 7.47 mmol), and NaHCO$_3$ (1.88 g, 22.3 mmol) was suspended in DMF and heated for two days at 110° C. Upon consumption of the starting material as determined by TLC, the solvent was removed under vacuum. The solid residue was triturated with water. An analytically pure sample of 86 was obtained by HPLC (ODS-A C18; 3-97% CH$_3$CN/H$_2$O gradient; 1.0 mL/min). Tan solid: HPLC R$_t$=1.63 min; R$_f$=0.45 (2% H$_2$O, 8% Methanol, 90% Ethyl acetate); $^1$H NMR (400 MHz, d$_6$-DMSO) δ 8.11 (s, 1H), 6.67 (s, 2H); MS (+)-ES [M+H]$^+$ 169; Elemental analysis for C$_5$H$_4$N$_4$OS.0.1 CH$_3$CN.0.1H$_2$O: calc'd: C, 35.88; H, 2.61; N, 32.99; S, 18.42. Found: C, 35.96; H, 2.75; N, 32.56; S, 18.42.

Step 3: Preparation of 5-Amino-3-(2',3',5'-tri-O-acetyl-β-D-ribofuranosyl)-3H-thiazolo[4,5-d]pyrimidin-2-one (79)

Compound 86 (62 mg, 0.4 mmol), 1,2,3,5-tetra-O-acetyl-β-D-ribofuranose tetraacetate (128 mg, 0.4 mmol), and catalytic bis(p-nitrophenyl)hydrogen phosphate (13 mg, 0.04 mmol) were mixed and placed in a 500 ml flask. The reaction vessel was carefully placed under vacuum (~5.0 mmHg) and lowered into an oil bath heated at 150° C. for 10 minutes. After cooling to room temperature, the solids were washed with ethyl acetate. The crude product was purified by flash column. (silica, 5 to 35% ethyl acetate gradient in chloroform) to yield 68 mg of compound 79 (40%) as a white solid as a white powder identical in all respects to material isolated in Example 38, step 2.

EXAMPLE 43

5-Amino-3-(2',3'-di-O-acetyl-β-D-ribofuranosyl)-3H-thiazolo[4,5-d]pyrimidin-2-one (89)

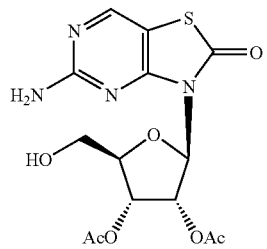

Step 1: Preparation of 5-Amino-3-(5'-O-tert-butyl-dimethylsilanyl-β-D-ribofuranosyl)-3H-thiazolo[4,5-d]pyrimidin-2-one (87)

To a solution of 79 (0.68 g, 2.28 mmol) in DMF (10 mL) was added imidazole (0.54 g, 7.93 mmol) and tert-butyldimethylsilyl chloride (0.68 g, 4.56 mmol) sequentially. The reaction mixture was stirred at room temperature for 2 h, at which point it was concentrated and purified by flash column chromatography (silica, MeOH/CHCl$_3$; gradient=5-20%) to afford 0.49 g (52%) 87 as a white solid: $^1$H (400 MHz, d$_6$-DMSO) δ 8.33 (s, 1H), 6.87 (s, 2H), 5.90 (d, J=4.0 Hz, 1H), 5.33 (d, J=5.6 Hz, 1H), 5.00 (d, J=5.2 Hz, 1H), 4.79 (q, J=5.2 Hz, 1H), 4.16 (q, J=5.2 Hz, 1H), 3.77 (m, 2H), 3.64 (dd, J=12.0, 7.2 Hz, 1H), 0.84 (s, 9H), 0.00 (s, 6H); MS (+)-ES [M+H]$^+$ m/z 415.4.

Step 2: Preparation of 5-Amino-3-(2,3'-di-O-acetyl, 5'-O-tert-butyl-dimethylsilanyl-β-D-ribofuranosyl)-3H-thiazolo[4,5-d]pyrimidin-2-one (88)

To a solution of 87 (0.20 g, 0.48 mmol) in acetonitrile (5 mL) at 0° C. was added successively Et$_3$N (0.26 mL, 1.86 mmol) and Ac$_2$O (91 μL, 0.96 mmol). The reaction mixture was stirred at room temperature for 24 h, whereupon it was concentrated and purified by flash column chromatography (silica, acetone/CHCl$_3$: gradient=5-10%) to afford 0.22 g (92%) of 88 as a white solid: $^1$H (400 MHz, d$_6$-DMSO) δ 8.36 (s, 1H), 6.90 (s, 2H), 6.00 (m, 2H), 5.57 (t, J=6.0 Hz, 1H), 4.07 (q, J=5.2 Hz, 1H), 3.77 (m, 2H), 2.07 (s, 3H), 2.06 (s, 3H), 0.83 (s, 9H), 0.00 (d, J=2.4 Hz, 6H); MS (+)-ES [M+H]$^+$ m/z 499.5.

Step 3: Preparation of 5-Amino-3-(2,3'-di-O-acetyl-β-D-ribofuranosyl)-3H-thiazolo[4,5-d]pyrimidin-2-one (89)

To a solution of 88 (0.22 g, 0.44 mmol) in THF (5 mL) in a plastic vial was added HF/pyridine (0.70 mL). The reaction was stirred for 2 h, concentrated and purified by flash column chromatography (silica, MeOH/CHCl$_3$: gradient=5-10%) to afford 0.17 g (100%) of the title compound as a white solid: mp 109-111° C.; $^1$H (400 MHz, d$_6$-DMSO) δ 8.37 (s, 1H), 6.91 (s, 2H), 6.00 (m, 2H), 5.48 (t, J=6.0 Hz, 1H), 4.91 (t, J=6.0 Hz, 1H), 4.04 (dd, J=10.4, 6.0 Hz, 1H), 3.64 (m, 1H), 3.52 (m, 1H), 2.08 (s, 3H), 2.05 (s, 3H); MS (+)-ES [M+H]$^+$ m/z 385.3. Elemental Analysis calc'd for C$_{14}$H$_{16}$N$_4$O$_7$S.0.5 CH$_3$OH.0.2 CHCl$_3$: C, 41.61; H, 4.32; N, 13.21; S 7.56: Found: C, 41.73; H, 4.29; N, 12.86; S, 7.33.

EXAMPLE 44

5-Amino-3-(2',3'-di-O-acetyl-β-D-ribofuranosyl)-3H-thiazolo[4,5-d]pyrimidin-2-one (89)

Alternative Synthetic Route A

Step 1: Preparation of 5-Amino-3-(2,3'-di-O-acetyl-β-D-ribofuranosyl)-3H-thiazolo[4,5-d]pyrimidin-2-one (89)

To a clear solution of 78 (500 mg) in acetone (5 mL) was added sodium phosphate buffer (pH=7.0, 0.1 M, 25 mL), upon which the solution became cloudy (white precipitate). *Candida antarctica* lipase resin (250 mg) was added to the mixture and the suspension was subsequently gently shaken for 10 h at room temperature. The resulting clear mixture was filtered, and organic solvent was removed under vacuum. The aqueous solution was then extracted with ethyl acetate (3×25 mL) and the organic layers were combined, dried over MgSO$_4$, and concentrated. The resulting solid could be further purified in a manner similar to that described in Example 43, step 3.

EXAMPLE 45

5-Amino-3-(2',3'-di-O-acetyl-β-D-ribofuranosyl)-thiazolo[4,5-d]pyrimidin-2,7-dione (92)

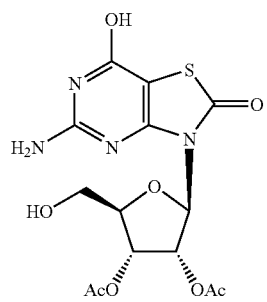

Step 1: Preparation of 5-Amino-3-(5'-O-tert-butyl-dimethylsilanyl-β-D-ribofuranosyl)-thiazolo[4,5-d]pyrimidin-2,7-dione (90)

To a mixture of 1 (12.0 g, 37.9 mmol) and imidazole (7.75 g, 114 mmol) in DMF was added tert-butyldimethylsilyl chloride 1 (5.72 g, 37.9 mmol) as a solution in DMF (25 mL). TLC analysis (20% MeOH—CHCl$_3$) indicated that reaction proceeded to ~60% completion. Additional tert-butyldimethylsilyl chloride (5.72 g, 37.9 mmol) was added portion-wise until the reaction was complete, whereupon it was quenched with MeOH (10 mL), and then concentrated to a brown residue. The residue was dissolved in EtOAc (800 mL), and then washed with water (3×200 mL). The organic phase was dried over anhydrous Na$_2$SO$_4$-charcoal, and then filtered through a short pad of SiO$_2$ to give a solution that was concentrated to a tan solid. Trituration of the crude product with Et$_2$O provided 90 12.41 g (76%) as a white solid: $^1$H (400 MHz, d$_6$-DMSO) δ 11.16 (s, 1H), 6.92 (br s, 2H), 5.77 (d, J=4.4 Hz, 1H), 5.27 (d, J=5.5 Hz, 1H), 4.95 (d, J=5.9 Hz, 1H), 4.73 (dd, J=9.9, 5.1 Hz, 1H), 4.11 (dd, J=10.6, 5.1 Hz, 1H), 3.70-3.76 (m, 2H), 3.59-3.64 (m, 1H), 0.84 (s, 9H), 0.0 (s, 6H).

Step 2: Preparation of 5-Amino-3-(2',3'-di-O-acetyl, 5'-O-tert-butyl-dimethylsilanyl-β-D-ribofuranosyl)-thiazolo[4,5-d]pyrimidin-2,7-dione (91)

To a homogeneous solution of diol 90 (2.44 g, 5.67 mmol) and Et$_3$N (2.37 mL, 17.0 mmol) in MeCN (40 mL) was added sequentially Ac$_2$O (1.06 mL, 11.3 mmol) and DMAP (69 mg, 0.57 mmol). The reaction mixture was stirred 3 h, then concentrated and chromatographed (SiO$_2$, gradient elution, 40-60% EtOAc—CHCl$_3$), affording 1.2 g (41%) of 91 as a white solid: $^1$H (400 MHz, d$_6$-DMSO) δ 11.25 (s, 1H), 7.96-8.00 (m, 1H), 7.54-7.57 (m, 2H), 7.24-7.28 (m, 2H) 6.96 (br s, 2H), 6.12 (s, 1H), 5.96 (s, 1H), 5.39-5.41 (m, 1H), 5.01-5.04 (m, 1H), 4.12-4.17 (m, 1H), 3.48-3.59 (m, 3H); MS (+)-ES [M+H]$^+$ m/z 515.

Step 3: Preparation of 5-Amino-3-(2,3'-di-O-acetyl-β-D-ribofuranosyl)-thiazolo[4,5-d]pyrimidin-2,7-dione (92)

To a homogeneous solution of 91 (1.2 g, 2.3 mmol) in THF (20 mL) was added 1.0 M tetrabutylammonium fluoride in THF (4.7 mL, 4.7 mmol). The reaction mixture was stirred 16 h, then concentrated and chromatographed to afford 800 mg (86%) of a white solid: $^1$H (400 MHz, d$_6$-DMSO) δ 11.25 (s, 1H), 6.97 (br s, 2H), 5.95 (dd, J=5.9, 4.4 Hz, 1H), 5.89 (d, J=4.8 Hz, 1H), 5.41 (t, J=6.2 Hz, 1H), 4.90 (t, J=5.9 Hz, 1H), 4.00 (q, J=5.9 Hz, 1H), 3.48-3.64 (m, 2H), 2.06 (s, 3H), 2.04 (s, 3H); MS (+)-ES [M+H]$^+$ m/z 401.

EXAMPLE 46

5-Amino-3-(2',3'-di-O-acetyl-5'-O-pivalyl-β-D-ribofuranosyl)-thiazolo[4,5-d]pyrimidin-2,7-dione (93)

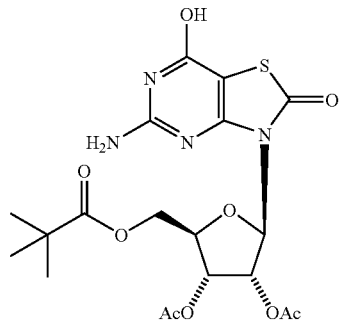

Step 1: Preparation of 5-Amino-3-(2',3'-di-O-acetyl-5'-O-pivalyl-β-D-ribofuranosyl)-thiazolo[4,5-d]pyrimidin-2,7-dione (93)

In a manner similar to Example 30, step 1, compound 93 was prepared from 92 and pivalic anhydride in a 21% yield as a white solid: $^1$H (400 MHz, $d_6$-DMSO) δ 11.27 (s, 1H), 6.98 (br s, 2H), 5.88-5.91 (m, 2H), 5.55 (dd, J=7.0, 5.9 Hz, 1H), 4.29 (dd, J=12.1, 4.0 Hz, 1H), 4.18-4.27 (m, 1H), 4.11 (dd, J=12.1, 5.1 Hz, 1H), 2.06 (s, 3H), 2.05 (s, 3H), 1.13 (s, 9H); MS (+)-ES [M+H]$^+$ m/z 485. Elemental Analysis calc'd for $C_{19}H_{24}N_4O_9S \cdot 0.75H_2O$: C, 45.82; H, 5.16; N, 11.25; S, 6.44. Found: C, 45.93; H, 5.20; N, 11.29; S, 6.44.

EXAMPLE 47

5-Amino-3-(2',3'-di-O-acetyl-5'-O-lauryl-β-D-ribofuranosyl)-thiazolo[4,5-d]pyrimidin-2,7-dione (94)

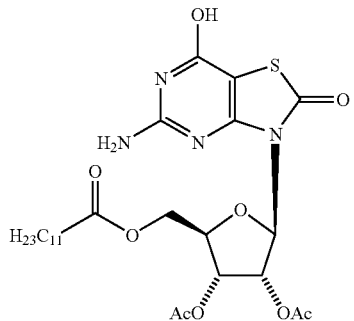

Step 1: Preparation of 5-Amino-3-(2',3'-di-O-acetyl-5'-O-lauryl-β-D-ribofuranosyl)-thiazolo[4,5-d]pyrimidin-2,7-dione (94)

In a manner similar to Example 30, step 1, compound 94 was prepared from 92 and lauric anhydride in 59% yield as a white solid: $^1$H (400 MHz, $d_6$-DMSO) δ 11.26 (s, 1H), 6.97 (br s, 2H), 5.87-5.91 (m, 2H), 5.51 (t, J=6.4 Hz, 1H), 4.36 (dd, J=12.1, 3.5 Hz, 1H), 4.18-4.22 (m, 1H), 4.08 (dd, J=12.1, 5.9 Hz, 1H), 2.27 (t, J=7.3 Hz, 1H), 2.06 (s, 6H), 1.46-1.50 (m, 1H), 1.17-1.28 (m, 16H), 0.85 (t, J=6.0 Hz, 3H); MS (+)-ES [M+H]$^+$ m/z 583. Elemental Analysis calc'd for $C_{26}H_{38}N_4O_9S$: C, 52.55; H, 6.49; N, 9.25; S, 5.29. Found: C, 52.58; H, 6.57; N, 9.49; S, 5.38.

EXAMPLE 48

5-Amino-3-(2',3',5'-tri-O-butyryl-β-D-ribofuranosyl)-thiazolo[4,5-d]pyrimidin-2,7-dione (95)

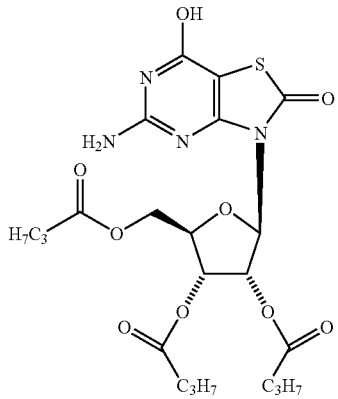

Step 1: Preparation of 5-Amino-3-(2',3',5'-tri-O-butyryl-β-D-ribofuranosyl)-thiazolo[4,5-d]pyrimidin-2,7-dione (95)

In a manner similar to Example 30, step 1, compound 95 was prepared from 1 and butyric anhydride. Purification by column chromatography (SiO$_2$, 40% EtOAc—CHCl$_3$) and trituration with Et$_2$O-hexanes to afforded a white solid in 17% yield: $^1$H (400 MHz, $d_6$-DMSO) δ 11.27 (s, 1H), 6.97 (br s, 2H), 5.87-5.91 (m, 2H), 5.54 (dd, J=12.8, 6.2 Hz, 1H), 4.37 (dd, J=12.1, 3.7 Hz, 1H), 4.18-4.22 (m, 1H), 4.10 (dd, J=12.1, 5.9 Hz, 1H), 2.25-2.38 (m, 6H), 1.47-1.59 (m, 6H), 0.84-0.91 (m, 9H); MS (+)-ES [M+H]$^+$ m/z 527. Elemental Analysis calc'd for $C_{22}H_{30}N_4O_9S$: C, 50.18; H, 5.74; N, 10.64; S, 6.09. Found: C, 50.18; H, 5.64; N, 10.56; S, 6.02.

EXAMPLE 49

5-Amino-3-(2',3',5'-tri-O-capryl-β-D-ribofuranosyl)-thiazolo[4,5-d]pyrimidin-2,7-dione (96)

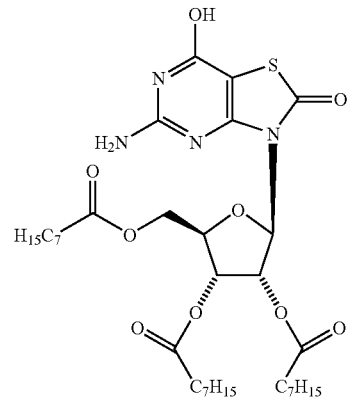

Step 1: Preparation of 5-Amino-3-(2',3',5'-tri-O-capryl-β-D-ribofuranosyl)-thiazolo[4,5-d]pyrimidin-2,7-dione (96)

In a manner similar to Example 30, step 1, compound 96 was prepared from 1 and caprylic anhydride in a 30% yield as a white solid: $^1$H (400 MHz, $d_6$-DMSO) δ 11.28 (s, 1H), 6.96 (br s, 2H), 5.87-5.92 (m, 2H), 5.35 (dd, J=12.8, 6.2 Hz, 1H), 4.35 (dd, J=11.7, 3.3 Hz, 1H), 4.17-4.21 (m, 1H), 4.09 (dd, J=11.7, 5.9 Hz, 1H), 2.24-2.39 (m, 6H), 1.48-1.53 (m, 6H), 1.22-1.25 (m, 2H), 0.82-0.87 (m, 9H); MS (+)-ES [M+H]$^+$ m/z 695. Elemental Analysis calc'd for $C_{34}H_{54}N_4O_9S$: C, 58.77; H, 7.83; N, 8.06; S, 4.61. Found: C, 58.65; N, 7.92; N, 7.98; S, 4.55.

EXAMPLE 50

5-Amino-3-(2',3'-di-O-acetyl-5'-O-L-valinyl-β-D-ribofuranosyl)-thiazolo[4,5-d]pyrimidin-2,7-dione hydrochloride (98)

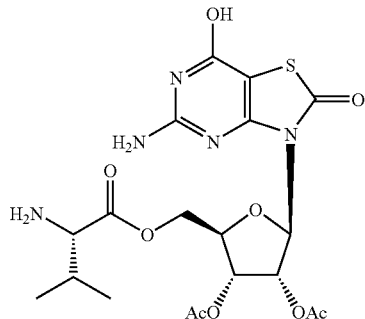

Step 1: Preparation of 5-Amino-3-[2,3'-di-O-acetyl-5'-O—(N-tert-butoxycarbonyl-L-valinyl])-β-D-ribofuranosyl)-thiazolo[4,5-d]pyrimidin-2,7-dione (97)

To a suspension of 3 (2.00 g, 4.09 mmol) in MeCN (10 mL) at room temperature was added $Et_3N$ (1.14 mL, 8.19 mmol). The resultant mixture was stirred 30 min, treated with di-tert-butyldicarbonate (894 mg, 4.09 mmol), and then stirred 16 h. To this mixture were added sequentially $Et_3N$ (1.40 mL, 10.0 mmol) and $Ac_2O$ (950 uL, 10.0 mmol). After 3 h, the mixture was concentrated, partitioned between EtOAc (200 mL) and water (100 mL), dried over anhydrous $Na_2SO_4$, concentrated, and then chromatographed ($SiO_2$, 80% EtOAc—$CHCl_3$), providing a white foam. The foam was triturated in $CHCl_3$-$Et_2O$-hexanes to give 1.38 g of diacetate 97 as a white solid: $^1H$ (400 MHz, $d_6$-DMSO) δ 11.29 (s, 1H), 7.05 (d, J=8.1 Hz, 1H), 6.99 (br s, 2H), 5.91 (d, J=1.5 Hz, 1H), 5.50 (s, 1H), 4.34 (dd, J=11.0, 2.2 Hz, 1H), 4.13-4.23 (m, 2H), 3.84 (dd, J=8.1, 6.6 Hz, 1H), 2.06 (s, 3H), 2.06 (s, 3H), 1.97-2.03 (m, 1H), 1.35 (s, 9H), 0.82 (d, J=6.6 Hz, 6H); MS (–)-ES [M–H]$^+$ m/z 598.

Step 2: Preparation of 5-Amino-3-(2',3'-di-O-acetyl-5'-O-L-valinyl-β-D-ribofuranosyl)-thiazolo[4,5-d]pyrimidin-2,7-dione hydrochloride (98)

To a mixture of 4 M HCl in dioxane (50 mL) and i-PrOAc was added solid 97 (1.35 g, 2.25 mmol). The resultant solution formed a heterogeneous mixture within several minutes. After 1 h, the suspension was filtered, washed with $Et_2O$, and then dried under high vacuum to afford 0.66 g (55%) of a white solid: $^1H$ (400 MHz, $d_6$-DMSO) δ 11.46 (s, 1H), 8.40 (s, 3H), 7.19 (br s, 2H), 4.46 (dd, J=12.5, 3.7 Hz, 1H), 4.28-4.44 (m, 2H), 3.85 (s, 1H), 3.68 (br s, 1H), 2.13-2.24 (m, 1H), 2.08 (s, 3H), 2.06 (s, 3H), 0.95 (d, J=7.3 Hz, 3H), 0.91 (d, J=6.6 Hz, 3H); MS (+)-ES [M+H]$^+$ m/z 498. Elemental analysis calc'd for $C_{19}H_{25}N_5O_9S1.0HCl.1.0H_2O$: C, 41.19; H, 5.09; Cl, 6.40; N, 12.64; S, 5.79. Found: C, 41.52; H, 5.01; Cl, 6.64; N, 12.85; S, 5.85.

EXAMPLE 51

5-Amino-3-(2',3'-di-O-butyryl-5'-O-L-valinyl-β-D-ribofuranosyl)-thiazolo[4,5-d]pyrimidin-2,7-dione hydrochloride (100)

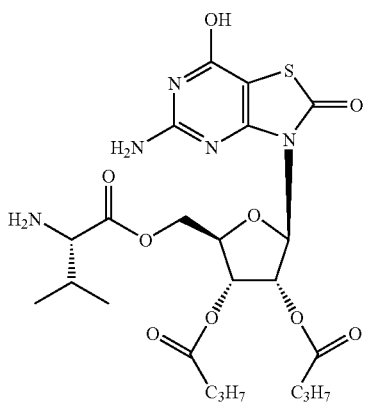

Step 1: Preparation of 5-Amino-3-(2,3'-di-O-butyryl-5'-N-tert-butoxycarbonyl-L-valinyl)-β-D-ribofuranosyl)-thiazolo[4,5-d]pyrimidin-2,7-dione (99)

In a manner similar to Example 49, step 1, 99 was prepared was prepared from 3 and butyric anhydride as a white waxy solid in 62% yield: $^1H$ (400 MHz, $d_6$-DMSO) δ 11.27 (s, 1H), 7.05 (d, J=8.1 Hz, 1H), 6.97 (br s, 2H), 5.92 (dd, J=6.6, 3.7 Hz, 1H), 5.88 (d, J=3.7 Hz, 1H), 4.35 (dd, J=11.7, 2.9 Hz, 1H), 4.13-4.23 (m, 2H), 3.84 (dd, J=8.1, 6.6 Hz, 1H), 2.24-2.39 (m, 4H), 1.98-2.03 (m, 1H), 1.46-1.59 (m, 4H), 1.35 (s, 9H), 0.85-0.91 (m, 12H); MS (–)-ES [M–H]$^+$ m/z 654.

Step 2: Preparation of 5-Amino-3-(2,3'-di-O-butyryl-5'-O-L-valinyl-β-D-ribofuranosyl)-thiazolo[4,5-d]pyrimidin-2,7-dione hydrochloride (100)

In a manner similar to Step 2 of Example 49 was prepared the title compound in a 60% yield as a white solid: $^1H$ (400 MHz, $d_6$-DMSO) δ 11.48 (s, 1H), 8.42 (s, 3H), 7.19 (br s, 2H), 6.00 (dd, J=6.6, 4.4 Hz, 1H), 5.92 (d, J=4.4 Hz, 1H), 5.57 (dd, J=12.5, 5.9 Hz, 1H), 4.47 (dd, J=12.5, 2.9 Hz, 1H), 4.35-4.40 (m, 1H), 4.27-4.31 (m, 1H), 3.83-3.85 (m, 1H), 2.28-2.40 (m, 4H), 2.14-2.25 (m, 1H), 1.46-1.60 (m, 4H), 0.83-0.96 (m, 12H); MS (–)-ES [M–H]$^+$ m/z 554. Elemental Analysis calc'd for $C_{23}H_{33}N_5O_9S.1.1HCl$ $0.5H_2O$: C, 45.68; H, 5.85; Cl, 6.45; N, 11.58; S, 5.30. Found: C, 45.34; H, 5.70; Cl, 6.59; N, 11.62; S, 5.42.

EXAMPLE 52

5-Amino-3-(2',3'-O-carbonyl-5'-O-L-valinyl-β-D-ribofuranosyl)-thiazolo[4,5-d]pyrimidin-2,7-dione hydrochloride (102)

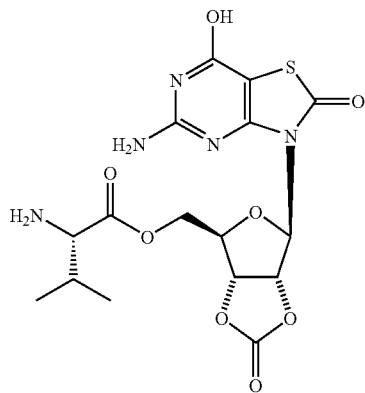

Step 1: Preparation of 5-Amino-3-[2',3'-O-carbonyl-5'-O—(N-tert-butoxycarbonyl-L-valinyl)-β-D-ribofuranosyl)]-thiazolo[4,5-d]pyrimidin-2,7-dione (101)

In a manner similar to Example 49, step 1, 101 was prepared was prepared from 3 and triphosgene as a white solid in 54% yield: $^1$H (400 MHz, $d_6$-DMSO) δ 11.34 (s, 1H), 7.09 (d, J=8.1 Hz, 1H), 7.06 (br s, 2H), 6.12 (s, 1H), 5.83 (d, J=8.1, 1H), 5.67-5.72 (m, 1H), 4.46-4.51 (m, 1H), 4.23-4.32 (m, 2H), 3.82 (dd, J=13.9, 5.9 Hz, 1H), 1.94-1.99 (m, 1H), 1.34 (s, 9H), 0.81 (d, J=6.6 Hz, 6H); MS (−)-ES [M−H]$^+$ m/z 540.

Step 2: Preparation of 5-Amino-3-(2',3'-O-carbonyl-5'-O-L-valinyl-β-D-ribofuranosyl)-thiazolo[4,5-d]pyrimidin-2,7-dione hydrochloride (102)

In a manner similar to Example 49, step 2, 102 was prepared was prepared in 65% yield as a white solid: $^1$H (400 MHz, $d_6$-DMSO) δ 11.51 (s, 1H), 8.36 (s, 3H), 7.25 (br s, 2H), 6.13 (s, 1H), 5.88 (d, J=7.3 Hz, 1H), 5.76-5.82 (m, 2H), 4.39 (dd, J=10.3, 2.9 Hz, 1H), 3.86 (s, 1H), 3.41-3.54 (m, 1H), 2.01-2.32 (m, 1H), 0.91 (d, J=7.3 Hz, 3H), 0.85 (d, J=6.6 Hz, 3H); MS (−)-ES [M−H]$^+$ m/z 440. Elemental Analysis calc'd for $C_{16}H_{19}N_5O_8S \cdot 1.1HCl \cdot 0.5H_2O \cdot 0.75$ $Et_2O$: C, 40.21; H, 4.22; Cl, 7.42; N, 14.66; S, 6.71. Found: C, 41.48; H, 5.08; Cl, 7.16; N, 12.75; S, 5.79.

EXAMPLE 53

5-Amino-3-(5'-O-(L-valinyl-L-valinyl)-β-D-ribofuranosyl)-thiazolo[4,5-d]pyrimidin-2,7-dione hydrochloride (104)

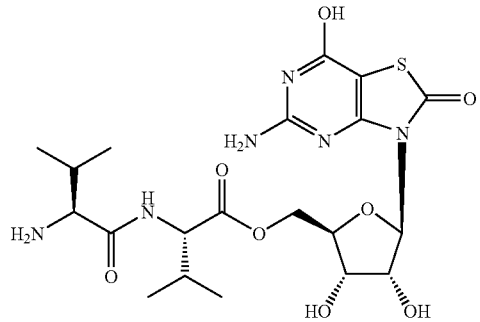

Step 1: Preparation of 5-Amino-3-[2',3'-O-isopropylidene-5'-O—(N-tert-butoxycarbonyl-L-valinyl-L-valinyl)-β-D-ribofuranosyl]-thiazolo[4,5-d]pyrimidin-2,7-dione (103)

To a heterogeneous mixture of Boc-Val-Val-OH (3.00 g, 9.48 mmol) and EDC (1.82 g, 9.48 mmol) in DCE (22.5 mL) at room temperature was added pyridine (7.5 mL). Upon becoming homogeneous, the mixture was stirred 1 h at room temperature, and then cooled to 0° C. To this solution was added sequentially 2 (3.07 g, 8.62 mmol) and DMAP (1.16 g, 9.48 mmol). The reaction mixture was stirred 30 min at 0° C., and then 16 h at room temperature. The mixture was evaporated to dryness, and then partitioned between EtOAc (200 mL) and water (100 mL). The organic phase was dried over anhydrous $Na_2SO_4$, concentrated, chromatographed ($SiO_2$, gradient elution 60% EtOAc—$CHCl_3$ to 100% EtOAc), and concentrated to a sticky solid. Trituration of the solid in $Et_2O$—$CHCl_3$ provided 2.048 g (36%) of 103 as a crystalline solid: $^1$H (400 MHz, $d_6$-DMSO) δ 11.63 (s, 1H), 11.37 (s, 1H), 11.25 (s, 1H), 7.92 (dd, J=13.2, 8.1 Hz, 1H), 6.98 (br s, 2H), 6.61 (dd, J=11.7, 8.8 Hz, 1H), 6.01 (s, 1H), 5.23-5.27 (m, 1H), 5.05 (br s, 1H), 4.10-4.35 (m, 3H), 3.76-3.90 (m, 2H), 3.57-3.60 (m, 1H), 1.80-2.06 (m, 2H), 1.47 (s, 3H), 1.36 (s, 3H), 1.35 (s, 3H), 1.29 (s, 3H), 0.77-0.86 (m, 12H); [M−H]$^+$ m/z 653.

Step 2: Preparation of 5-Amino-3-(5'-O-[L-valinyl-L-valinyl]-β-D-ribofuranosyl)-thiazolo[4,5-d]pyrimidine-2,7-dione hydrochloride (104)

To a mixture of 4 M HCl in dioxane (50 mL) and i-PrOAc was added solid 103 (1.48 g, 2.26 mmol). The resultant solution formed a heterogeneous mixture within several minutes. After 1 h, the suspension was filtered, washed with $Et_2O$, and then dried under high vacuum to afford 948 mg (74%) of 104 as a white solid: $^1$H (400 MHz, $d_6$-DMSO) δ 11.29 (s, 1H), 8.52 (d, J=7.7 Hz, 1H), 8.06 (br s, 3H), 7.03 (br s, 2H), 5.79 (d, J=4.0 Hz, 1H), 5.42 (d, J=5.5 Hz, 1H), 5.13 (d, J=5.9 Hz, 1H), 4.71 (dd, J=9.9, 5.5 Hz, 1H), 4.35 (dd, J=11.7, 3.3 Hz, 1H), 4.18-4.22 (m, 2H), 4.06 (dd, J=11.7, 8.0 Hz, 1H), 3.88-3.92 (m, 1H), 3.69 (s, 1H), 2.02-2.13 (m, 2H), 0.87-0.92 (m, 12H); MS (−)-ES [M−H]$^+$ m/z 513.

EXAMPLE 54

5-Amino-3-(5'-O-(L-phenylalinyl-L-valinyl)-β-D-ribofuranosyl)-thiazolo[4,5-d]pyrimidin-2,7-dione hydrochloride (106)

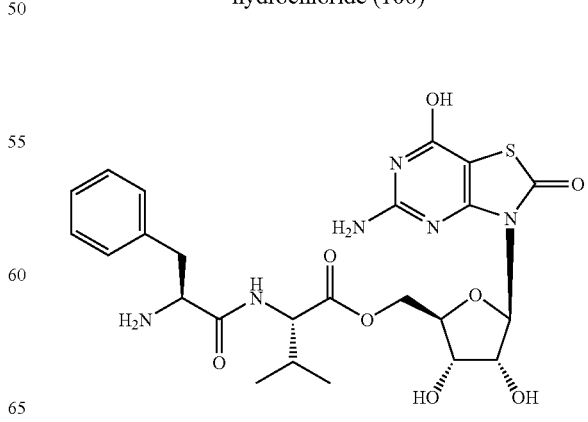

Step 1: Preparation of 5-Amino-3-[2',3'-O-isopropylidene-5'-O—(N-tert-butoxycarbonyl-L-phenylalinyl-L-valinyl)-β-D-ribofuranosyl]-thiazolo[4,5-d]pyrimidin-2,7-dione (105)

In a manner similar to Step 1 of Example 52 was prepared the title compound in a 64% yield as a white solid: $^1$H (400 MHz, d$_6$-DMSO) δ 11.24 (s, 1H), 8.00-8.08 (m, 1H), 7.22-7.23 (m, 4H), 7.13-7.16 (m, 1H), 6.98 (br s, 2H), 6.83-6.87 (m, 1H), 6.02 (d, J=3.7 Hz, 1H), 5.25-5.28 (m, 1H), 5.06 (s, 1H), 4.12-4.34 (m, 4H), 2.88-2.94 (m, 1H), 2.66-2.75 (m, 1H), 1.97-2.04 (m, 1H), 1.46 (d, J=7.3 Hz, 2H), 1.17-1.28 (m, 14H), 0.77-0.85 (m, 6H); MS (−)-ES [M−H]$^+$ m/z 701.

Step 2: Preparation of 5-Amino-3-(5'-O-[L-phenylalinyl-L-valinyl]-β-D-ribofuranosyl)-thiazolo[4,5-d]pyrimidin-2,7-dione hydrochloride (106)

In a manner similar to Step 2 of Example 52 was prepared the title compound in a 74% yield as a white solid: $^1$H (400 MHz, d$_6$-DMSO) δ 11.32 (s, 1H), 8.72 (d, J=8.0 Hz, 1H), 8.16 (br s, 3H), 7.19-7.28 (m, 5H), 7.09 (br s, 2H), 5.79 (d, J=4.0 Hz, 1H), 5.20 (br s, 3H), 4.70 (dd, J=5.5, 4.4 Hz, 1H), 4.36 (dd, J=11.7, 3.3 Hz, 1H), 4.03-4.24 (m, 3H), 3.90-3.94 (m, 1H), 3.09 (dd, J=14.0, 5.9 Hz, 1H), 2.92 (dd, J=14.0, 7.7 Hz, 1H), 2.01-2.10 (m, 1H), 0.89 (d, J=6.6 Hz, 3H), 0.88 (d, J=6.6 Hz, 3H); MS (−)-ES M$^+$ m/z 562.

EXAMPLE 55

5-Amino-3-(5'-O-capryl-β-D-ribofuranosyl)-thiazolo[4,5-d]pyrimidin-2,7-dione hydrochloride (109)

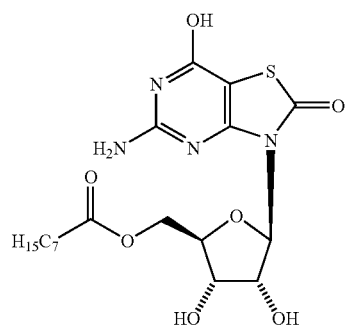

Step 1: Preparation of 5-Amino-3-[2',3'-O-(4-fluorobenzylidene)-β-D-ribofuranosyl]-thiazolo[4,5-d]pyrimidin-2,7-dione (107)

To a homogeneous solution of the 90 (750 mg, 1.74 mmol) and 4-fluorobenzaldehyde (1.86 mL, 17.4 mmol) in THF was added H$_2$SO$_4$ (1 drop). The resultant mixture was stirred 16 h, whereupon a precipitate had formed. Filtration afforded 360 mg (49%) of benzylidene acetal 107 as a yellow solid: $^1$H (400 MHz, d$_6$-DMSO) δ 11.24 (s, 1H), 7.96-8.00 (m, 1H), 7.54-7.57 (m, 2H), 7.24-7.28 (m, 2H), 6.96 (br s, 2H), 6.12 (s, 1H), 5.96 (s, 1H), 5.39-5.41 (m, 1H), 5.01-5.04 (m, 1H), 4.12-4.17 (m, 1H), 3.48-3.59 (m, 3H); MS (+)-ES [M+H]$^+$ m/z 423.

Step 2: Preparation of 5-Amino-3-[2',3'-O-(4-fluorobenzylidene)-5'-capryloxy-β-D-ribofuranosyl]-thiazolo[4,5-d]pyrimidin-2,7-dione (108)

To a heterogeneous mixture of 107 (360 mg, 0.605 mmol), Et$_3$N (278 uL, 2.00 mmol), and DMAP (5 mg, 0.04 mmol) in MeCN (5 mL) was added caprylic anhydride (180 uL, 0.605 mmol). The reaction mixture was stirred 16 h, whereupon it was concentrated and chromatographed (SiO$_2$, gradient elution 40-60% EtOAc—CHCl$_3$), affording 407 mg (87%) of 108 as a white solid: $^1$H (400 MHz, d$_6$-DMSO) δ 11.28 (s, 1H), 7.56 (dd, J=8.4, 6.2 Hz, 2H), 7.25 (dd, J=9.2, 8.8 Hz, 2H), 7.00 (br s, 2H), 6.14 (s, 1H), 5.97 (s, 1H), 5.39 (d, J=7.0 Hz, 1H), 5.15-5.18 (m, 1H), 4.27-4.35 (m, 2H), 4.14 (dd, J=11.4, 7.7 Hz, 1H), 2.26 (t, J=7.0 Hz, 2H), 1.45-1.47 (m, 2H), 1.20-1.23 (m, 8H), 0.82 (t, J=5.9 Hz, 3H); MS (+)-ES [M+H]$^+$ m/z 549.

Step 4: Preparation of 5-Amino-3-(5'-O-capryl-β-D-ribofuranosyl)-thiazolo[4,5-d]pyrimidin-2,7-dione (109)

A mixture of 108 (200 mg, 0.365 mmol) and PPTS (5 mg, 0.02 mmol) in MeOH (40 mL) was heated to 45° C. for 20 min, concentrated and submitted to HPLC purification affording 69 mg (43%) of the title compound as a white solid: $^1$H (400 MHz, d$_6$-DMSO) δ 11.18 (s, 1H), 6.93 (br s, 2H), 5.77 (d, J=4.0 Hz, 1H), 5.35 (d, J=5.3 Hz, 1H), 5.08 (d, J=6.0 Hz, 1H), 4.67 (dd, J=9.9, 5.3 Hz, 1H), 4.30 (dd, J=11.9, 3.7 Hz, 1H), 4.21 (dd, J=12.1, 6.4 Hz, 1H), 3.98 (dd, J=11.9, 6.8 Hz, 1H), 3.84-3.88 (m, 1H), 2.27 (t, J=7.1 Hz, 2H), 1.47-0.150 (m, 2H), 1.19-1.25 (m, 8H), 0.84 (t, J=6.8 Hz, 3H); MS (+)-ES [M+H]$^+$ m/z 443. Elemental Analysis calc'd for C$_{18}$H$_{26}$N$_4$O$_7$S.1.0H$_2$O: C, 46.71; H, 5.78; N, 11.47; S, 6.56. Found: C, 46.62; H, 6.09; N, 12.01; S, 6.89.

EXAMPLE 56

(5-Amino-3-(2',3',5'-tri-O-acetyl-β-D-ribofuranosyl)-2,3-dihydro-thiazolo[4,5-d]pyrimidin-7-yl)-toluene-4-sulfonic acid-ester (110)

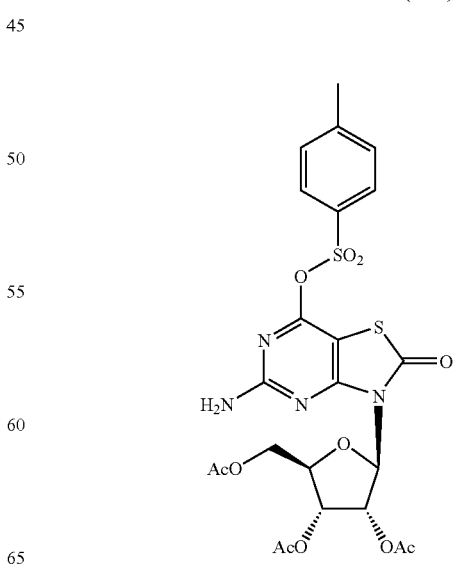

Step 1: 5-Amino-3-(2',3',5'-tri-O-acetyl-β-D-ribo-furanosyl)-thiazolo[4,5-d]pyrimidin-7-(4-toluene-sulfonyloxy)-2-one (110)

Compound 25 (250 mg, 0.56 mmol) was dissolved in $CH_2Cl_2$ (10 mL) and DMAP (3.4 mg, 0.028 mmol) and the TEA (0.24 mL, 1.70 mmol) were added. To this mixture was added p-toluenesulfonyl chloride (21.5 mg, 113 mmol) in aliquots of one fifth of one equivalent every 40 min. The progress of the reaction was monitored by TLC. After 3 h most of the starting material was consumed. The crude reaction mixture was passed through a silica plug, concentrated and purified by flash column using 25% ethyl acetate in chloroform. The product was dissolved in ethyl ether and upon the addition of hexanes compound 16 (190 mg, 0.32 mmol) precipitated as a white solid: $^1H$ NMR (400 MHz, $d_6$-DMSO) δ 8.00 (d, J=8.0 Hz, 2H), 7.47 (d, J=8.0 Hz, 2H), 7.35 (s, 2H), 5.97 (d, J=4.0 Hz, 1H), 5.86 (m, 1H), 5.52 (m, 1H), 4.35 (m, 1H), 4.24 (m, 1H), 4.08 (m, 1H), 2.43 (s, 3H), 2.05 (s, 3H), 2.04 (s, 3H), 1.97 (s, 3H); MS (+)-ES $[M+H]^+$ 597. $R_f$=0.65 (75% Ethyl acetate-$CHCl_3$). Elemental Analysis for $C_{23}H_{24}N_4O_{11}S$: calc'd: C, 46.30; H, 4.05; N, 9.39; S, 10.75. Found: C, 46.54; H, 4.27; N, 9.19; S, 10.44.

Biological Testing

The ability of compounds of Formula I to demonstrate favorable oral delivery characteristics and to induce immune responses when administered by a selected route was readily demonstrated in experiments in mice and beagle dogs. The results of such measurements for compounds of Formula I can be compared with the results of similar experiments with compounds described in the literature referenced in the present disclosure (e.g., U.S. Pat. Nos. 5,041,426 and 4,880,784) to reveal the advantages of Formula I compounds with respect to pharmacokinetic and pharmacodynamic properties.

Interferon Alpha (Mu-IFN-α) Concentrations in Mice

The normal mouse provides a useful system for the assessment of the degree to which the inventions described herein provide material improvement in the oral delivery of 1 (isatoribine). Not only can one measure the plasma concentrations of isatoribine arising from oral administration of the said prodrug(s) but also the extensive immunological research conducted in the mouse has provided reagents suitable for measuring the levels of interferon alpha, a cytokine of interest reflecting one of the desired biologic activities of isatoribine.

We have used the murine system in a series of experiments that demonstrate that 3, the 5'-valine ester of 1 (val-isatoribine) elicits an interferon response substantially improved over that resulting from administration of isatoribine itself.

Table 1 records the results of an assay for murine interferon alpha in the plasma of mice that were dosed two times with isatoribine, formulated in bicarbonate, at a level of 50 mg/kg by the oral route. It is evident that no interferon was measurable even when the dose was repeated after an interval of four hours.

TABLE 1

Interferon Alpha (Mu-IFN-α) Plasma Concentration (pg/mL) in Mice Following Two Oral 50 mg/kg Doses of Isatoribine 4 Hours Apart

| Time, h | Individual Value | | | Mean | SD |
|---|---|---|---|---|---|
| | First Dose | | | | |
| 0.00 | $BQL^{50}$ | $BQL^{125}$ | $BQL^{50}$ | 0.00 | 0.00 |
| 0.03 | $BQL^{25}$ | $BQL^{250}$ | $BQL^{25}$ | 0.00 | 0.00 |
| 0.08 | $BQL^{25}$ | $BQL^{25}$ | $BQL^{25}$ | 0.00 | 0.00 |
| 0.25 | $BQL^{50}$ | $BQL^{25}$ | $BQL^{25}$ | 0.00 | 0.00 |

TABLE 1-continued

Interferon Alpha (Mu-IFN-α) Plasma Concentration (pg/mL) in Mice Following Two Oral 50 mg/kg Doses of Isatoribine 4 Hours Apart

| Time, h | Individual Value | | | Mean | SD |
|---|---|---|---|---|---|
| 0.50 | $BQL^{25}$ | $BQL^{25}$ | $BQL^{25}$ | 0.00 | 0.00 |
| 1.00 | $BQL^{25}$ | $BQL^{25}$ | $BQL^{25}$ | 0.00 | 0.00 |
| 1.50 | $BQL^{100}$ | $BQL^{25}$ | $BQL^{25}$ | 0.00 | 0.00 |
| 2.00 | $BQL^{25}$ | $BQL^{75}$ | $BQL^{25}$ | 0.00 | 0.00 |
| 3.00 | $BQL^{25}$ | $BQL^{25}$ | $BQL^{25}$ | 0.00 | 0.00 |
| 4.00 | $BQL^{25}$ | $BQL^{25}$ | $BQL^{25}$ | 0.00 | 0.00 |
| | Second Dose | | | | |
| 4.03 | $BQL^{25}$ | $BQL^{25}$ | $BQL^{25}$ | 0.00 | 0.00 |
| 4.08 | $BQL^{25}$ | $BQL^{25}$ | $BQL^{25}$ | 0.00 | 0.00 |
| 4.25 | $BQL^{25}$ | $BQL^{25}$ | $BQL^{25}$ | 0.00 | 0.00 |
| 4.50 | $BQL^{50}$ | $BQL^{37.5}$ | $BQL^{50}$ | 0.00 | 0.00 |
| 5.00 | $BQL^{50}$ | $BQL^{50}$ | $BQL^{50}$ | 0.00 | 0.00 |
| 5.50 | $BQL^{37.5}$ | $BQL^{37.5}$ | $BQL^{37.5}$ | 0.00 | 0.00 |
| 6.00 | $BQL^{50}$ | $BQL^{41.3}$ | $BQL^{37.5}$ | 0.00 | 0.00 |
| 7.00 | $BQL^{50}$ | $BQL^{50}$ | $BQL^{50}$ | 0.00 | 0.00 |
| 8.00 | $BQL^{50}$ | $BQL^{25}$ | $BQL^{50}$ | 0.00 | 0.00 |

$BQL^n$—Below Elevated Quantifiable Limit < n pg/mL.

Table 2 records the results of assays for murine interferon alpha in the plasma of mice that first were dosed with bicarbonate and then four hours later were dosed orally with isatoribine, formulated in bicarbonate, at a level of 50 mg/kg. Interferon was reported in the plasma from four mice, including two that had received the bicarbonate vehicle dose. All the values reported in this experiment were low, and the reported interferon levels were not consistently reported for all three mice assessed at each time point, suggesting that these signals may be artifacts arising from measurement near the lower limits of the assay.

TABLE 2

Interferon Alpha (Mu-IFN-α) Plasma Concentration (pg/mL) in Mice Following One Vehicle Dose and One 50 mg/kg Dose of Isatoribine 4 Hours Later

| Time, h | Individual Value | | | Mean | SD |
|---|---|---|---|---|---|
| | First Dose | | | | |
| 0.00 | $BQL^{50}$ | $BQL^{100}$ | $BQL^{62.5}$ | 0.00 | 0.00 |
| 0.03 | $BQL^{50}$ | $BQL^{50}$ | $BQL^{37.5}$ | 0.00 | 0.00 |
| 0.08 | $BQL^{50}$ | $BQL^{50}$ | $BQL^{50}$ | 0.00 | 0.00 |
| 0.25 | $BQL^{50}$ | $BQL^{62.5}$ | $BQL^{50}$ | 0.00 | 0.00 |
| 0.50 | $BQL^{50}$ | $BQL^{50}$ | $BQL^{50}$ | 0.00 | 0.00 |
| 1.00 | $BQL^{50}$ | $BQL^{50}$ | $BQL^{100}$ | 0.00 | 0.00 |
| 1.50 | $BQL^{50}$ | $BQL^{100}$ | $BQL^{50}$ | 0.00 | 0.00 |
| 2.00 | 34.9 | $BQL^{25}$ | $BQL^{25}$ | 11.6 | 20.15 |
| 3.00 | $BQL^{25}$ | $BQL^{25}$ | $BQL^{25}$ | 0.00 | 0.00 |
| 4.00 | $BQL^{25}$ | 35.4 | $BQL^{100}$ | 11.8 | 20.44 |
| | Second Dose | | | | |
| 4.03 | $BQL^{25}$ | $BQL^{25}$ | $BQL^{25}$ | 0.00 | 0.00 |
| 4.08 | $BQL^{25}$ | $BQL^{25}$ | $BQL^{25}$ | 0.00 | 0.00 |
| 4.25 | $BQL^{25}$ | $BQL^{25}$ | $BQL^{25}$ | 0.00 | 0.00 |
| 4.50 | $BQL^{100}$ | $BQL^{25}$ | 133.2 | 44.4 | 76.90 |
| 5.00 | 74.9 | $BQL^{50}$ | NR | 37.5 | 52.96 |
| 5.50 | $BQL^{250}$ | $BQL^{75}$ | $BQL^{25}$ | 0.00 | 0.00 |
| 6.00 | $BQL^{25}$ | $BQL^{75}$ | $BQL^{75}$ | 0.00 | 0.00 |
| 7.00 | $BQL^{50}$ | $BQL^{50}$ | $BQL^{25}$ | 0.00 | 0.00 |
| 8.00 | $BQL^{25}$ | $BQL^{25}$ | $BQL^{25}$ | 0.00 | 0.00 |

$BQL^n$—Below Elevated Quantifiable Limit < n pg/mL.
NR—Not reportable.

Table 3 records the results of assays for murine interferon alpha in the plasma of mice that were dosed orally with val-isatoribine, dissolved in bicarbonate, at a dose that is equivalent to 50/mg/kg of isatoribine on a molar basis. It is evident that interferon was readily measurable at 1.0 hour, 1.5 hours, and 2.0 hours after dosing. Interferon was detected in all mice assayed at a given time point, indicating the reliability of the effect following val-isatoribine administration. Thus a single administration of val-isatoribine was superior to either a single dose or a repeated dose of isatoribine.

TABLE 3

Plasma Concentration (pg/mL) of Interferon Alpha (Mu-IFN-α) in Mice Following a Single 73.0 mg/kg Dose of Val-Isatoribine

| Time, h | Individual Value | | | Mean | SD |
|---|---|---|---|---|---|
| 0.00 | BQL | BQL[125] | BQL[25] | 0.00 | 0.00 |
| 0.25 | BQL | BQL | BQL | 0.00 | 0.00 |
| 0.50 | BQL[25] | BQL[25] | BQL | 0.00 | 0.00 |
| 0.75 | BQL | BQL | BQL[25] | 0.00 | 0.00 |
| 1.00 | 173.2 | 125.1 | 89.0 | 129.1 | 42.24 |
| 1.50 | 202.9 | 145.9 | 294.8 | 214.5 | 75.13 |
| 2.00 | 49.2 | 137.9 | 138.3 | 108.5 | 51.33 |
| 3.00 | BQL[25] | NR | NR | 0.00 | 0.00 |
| 4.00 | BQL[25] | 27.6 | BQL | 9.20 | 15.90 |
| 5.00 | BQL | BQL[25] | BQL[25] | 0.00 | 0.00 |

BQL—Below the Quantifiable Limit <12.5 pg/mL
BQL[n]—Below the Elevated Quantifiable Limit < n pg/mL
NR—Not Reportable The data tabulated in Tables 1, 2, and 3 may be also considered from the point of view of the incidence of measurable interferon levels. Interferon was detected in the plasma of only 4 of the 114 mice used in the studies of isatoribine, whereas 10 of the 30 mice dosed with val-isatoribine had detectable interferon in their plasma. Thus, the prodrug increased the proportion of mice exhibiting an interferon response from 4% to 30% and the magnitude of both the average and peak response was increased twofold.

In other experiments, plasma levels of isatoribine and interferon alpha were measured in mice that were dosed with isatoribine by the intravenous route, and these levels were compared to the levels of isatoribine and interferon alpha arising after oral administration of val-isatoribine. These data are summarized in FIG. 1.

In this figure it is evident that the levels of interferon alpha induced by oral val-isatoribine ("val-isator") (at 50 mg/kg isatoribine molar equivalent) was similar to that from intravenous isatoribine ("isator") at 25 mg/kg. Thus, oral val-isatoribine provides levels of isatoribine and interferon that are approximately 50% of those observed after intravenous administration of isatoribine itself.

Beagle Dog

The effect of a prodrug (val-isatoribine, 3) on the systemic exposure to isatoribine (1) after oral administration to beagle dogs was investigated. Isatoribine was prepared in sodium bicarbonate solution. Val-isatoribine and isatoribine were prepared as the following formulations, which were chosen to ensure solubility:

Formulation 1: Isatoribine in sodium bicarbonate solution, 1 and 4 mg/mL.
Formulation 2: Val-isatoribine in phosphate buffered saline, 1.62 and 6.48 mg/mL, equivalent to 1 and 4 mg/mL of isatoribine on a molar basis.

Four male and four female adult beagle dogs weighing between 15 to 27 kg and approximately 1-2 years old were used at the beginning of the study. The animals were divided into 2 groups of 2 males and 2 females each. The test material was administered by gavage on Days 1 and 8, allowing a 7-day washout period between administrations. Blood samples (2 mL) were collected from each animal at predose, 15, 30 minutes, 1, 2, 3, 4, 6, 8 and 10 hours into lithium heparin tubes after each dosing. The plasma was frozen at −70° C. until analysis. The plasma was analyzed for isatoribine by an HPLC-MS/MS assay.

The pharmacokinetic parameters for isatoribine arising from isatoribine or val-isatoribine in each dog are summarized in Tables 4 and 5. The ratios for the key pharmacokinetic parameters defining the maximum concentration (Cmax) and total exposure as measured by the area under the time-concentration curve (AUC) for the prodrug and the bicarbonate solution at the 50 mg/kg dose are summarized in Table 6. For the prodrug 3, the Cmax ratio was 2.98±0.695 and the AUC ratio was 2.38±0.485. These results indicate that at 50 mg/kg dose, the prodrug val-isatoribine provided substantially higher Cmax and greater bioavailability than isatoribine in bicarbonate solution.

The ratios for the Cmax and AUC for the prodrug to the bicarbonate solution for the 10 mg/kg dose are summarized in Table 7. For the prodrug, the Cmax ratio was 2.24±0.249 and the AUC ratio was 1.82±0.529. These results indicate that at 10 mg/kg dose, the prodrug val-isatoribine provided higher Cmax and greater bioavailability than isatoribine in bicarbonate solution.

Thus, the maximum concentrations of isatoribine achieved after oral dosing are at least doubled, and the systemic exposure to isatoribine is enhanced by approximately 2-fold following oral administration of the prodrug val-isatoribine, compared to isatoribine itself, at both 10 and 50 mg/kg dose.

TABLE 4

Pharmacokinetic Parameters of Isatoribine in Dogs dosed at 50 mg/kg

| | | Dosing Period | |
|---|---|---|---|
| | | 1 | 2 |
| | | Formulation | |
| | | Isatoribine | Val-isatoribine |
| | | Dose, mg/kg molar equivalent isatoribine | |
| Animal Number | | 50 | 50 |
| Dog 3517322 | Cmax, ng/mL | 3038.7 | 11741.5 |
| | Tmax, h | 0.50 | 0.50 |
| | AUC (0-inf), ng · h/mL | 15227.0 | 33038.1 |
| | $T_{1/2}$, h | 6.4 | 2.4 |
| Dog 3521451 | Cmax, ng/mL | 3354.0 | 10652.1 |
| | Tmax, h | 1.00 | 1.00 |
| | AUC (0-inf), ng · h/mL | 9422.2 | 26552.7 |
| | $T_{1/2}$, h | 1.9 | 1.6 |
| Dog 3528707 | Cmax, ng/mL | 8915.3 | 20340.6 |
| | Tmax, h | 0.50 | 0.50 |
| | AUC (0-inf), ng · h/mL | 29701.7 | 53273.0 |
| | $T_{1/2}$, h | 2.2 | 2.3 |
| Dog 3532828 | Cmax, ng/mL | 6134.7 | 15987.9 |
| | Tmax, h | 0.50 | 0.50 |
| | AUC (0-inf), ng · h/mL | 12069.7 | 32987.0 |
| | $T_{1/2}$, h | 1.4 | 1.6 |

TABLE 5

Pharmacokinetic Parameters of Isatoribine in Dogs Dosed at 10 mg/kg

| | | Dosing Period | |
|---|---|---|---|
| | | 1 | 2 |
| | | Formulation | |
| | | Isatoribine | Val-isatoribine |
| | | Dose, mg/kg molar equivalent isatoribine | |
| Animal Number | | 10 | 10 |
| Dog 3524523 | Cmax, ng/mL | 4091.5 | 8594.6 |
| | Tmax, h | 1.00 | 0.50 |
| | AUC (0-inf), ng · h/mL | 13305.8 | 17166.2 |
| | $T_{1/2}$, h | 2.1 | 1.7 |
| Dog 3526402 | Cmax, ng/mL | 1859.5 | 4047.0 |
| | Tmax, h | 1.00 | 1.00 |
| | AUC (0-inf), ng · h/mL | 5774.4 | 10548.9 |
| | $T_{1/2}$, h | 1.6 | 2.2 |
| Dog 357450 | Cmax, ng/mL | 1620.3 | 4228.7 |
| | Tmax, h | 0.50 | 1.00 |
| | AUC (0-inf), ng · h/mL | 4387.3 | 11158.0 |
| | $T_{1/2}$, h | 1.5 | 2.3 |
| Dog 354708 | Cmax, ng/mL | 2781.2 | 5784.8 |
| | Tmax, h | 0.50 | 0.50 |
| | AUC (0-inf), ng · h/mL | 7522.1 | 12259.1 |
| | $T_{1/2}$, h | 1.6 | 2.0 |

TABLE 6

Ratio of Pharmacokinetic Parameters of Isatoribine in Dogs Dosed at 50 mg/kg

| | | Formulation | |
|---|---|---|---|
| Animal Number | | Isatoribine | Val-isatoribine |
| Dog 3517322 | Cmax Ratio | 1.00 | 3.86 |
| | AUC Ratio | 1.00 | 2.17 |
| Dog 3521451 | Cmax Ratio | 1.00 | 3.18 |
| | AUC Ratio | 1.00 | 2.82 |
| Dog 3528707 | Cmax Ratio | 1.00 | 2.28 |
| | AUC Ratio | 1.00 | 1.79 |
| Dog 3532828 | Cmax Ratio | 1.00 | 2.61 |
| | AUC Ratio | 1.00 | 2.73 |
| | Mean Cmax Ratio | N/A | 2.98 |
| | SD Cmax Ratio | N/A | 0.695 |
| | Mean AUC Ratio | N/A | 2.38 |
| | SD AUC Ratio | N/A | 0.485 |

TABLE 7

Ratio of Pharmacokinetic Parameters of Isatoribine in Dogs Dosed at 10 mg/kg

| | | Formulation | |
|---|---|---|---|
| Animal Number | | Isatoribine | Val-isatoribine |
| Dog 3524523 | Cmax Ratio | 1.00 | 2.10 |
| | AUC Ratio | 1.00 | 1.29 |
| Dog 3526402 | Cmax Ratio | 1.00 | 2.18 |
| | AUC Ratio | 1.00 | 2.20 |
| Dog 3527450 | Cmax Ratio | 1.00 | 2.61 |
| | AUC Ratio | 1.00 | 2.54 |
| Dog 355708 | Cmax Ratio | 1.00 | 2.08 |
| | AUC Ratio | 1.00 | 1.63 |
| | Mean Cmax Ratio | N/A | 2.24 |
| | SD Cmax Ratio | N/A | 0.249 |

TABLE 7-continued

Ratio of Pharmacokinetic Parameters of Isatoribine in Dogs Dosed at 10 mg/kg

| | Formulation | |
|---|---|---|
| Animal Number | Isatoribine | Val-isatoribine |
| Mean AUC Ratio | N/A | 1.82 |
| SD AUC Ratio | N/A | 0.529 |

The prodrug is preferred for several reasons. First, the prodrug is easily formulated to provide a high proportion of active agent. This results in small capsule sizes for a given dose, which is an advantage for an oral product. Second, the prodrugs offer the prospect of masking the active structure as the agent passes through lymphoid tissue lining the gut, which should minimize activation of this tissue and thereby improve oral tolerability. Finally, at the doses tested, val-isatoribine provides plasma levels of isatoribine that are well within the range desirable for biologic effect after oral administration, which is not the case for isatoribine itself.

Reduction of Gastrointestinal Irritancy

Formula I compounds of the invention also demonstrate unexpected and greatly reduced toxicology effects, and in particular reduced GI irritancy. The gastrointestinal ("GI") tract is lined with substantial immune tissue (e.g., Peyer's patches, etc.). Formula I compounds offer the prospect of masking the active structure as the agent passes through lymphoid tissue lining the gut, which should minimize activation of this tissue and thereby reduce GI irritancy.

Robins et al. have shown that elimination of the 5'-hydroxyl of isatoribine nucleoside eliminates activity. See Robins et al., Adv. Enzyme Regul., 29, 97-121 (1989). Without being limited to any particular theory, it was hypothesized that blockade of this hydroxyl site by an ester substitution would similarly eliminate activity but allow transport in the systemic circulation, where the valine ester would be cleaved and result in exposure to isatoribine.

We have found that the hypothesis was confirmed. Formal toxicology studies of intravenously administered isatoribine and orally administered isatoribine and val-isatoribine were conducted in beagle dogs. The toxicology results for orally administered isatoribine are from a study conducted by ICN/Nucleic Acid Research Institute.

We compared in the dog the oral toxicology of 1 and 3, and the intravenous toxicology of 1. We observed that the oral toxicology of 3 was much more like intravenous 1 than it was like oral 1. In particular, the dose limiting toxicology of oral 3 was similar in nature to that of intravenous 1, and occurred at blood exposures that were similar to those observed after intravenous 1. In contrast, oral 1 had a different limiting toxicity (gastrointestinal lesions) and this toxicity was observed at a dose lower than the toxic dose of either intravenous 1 or oral 3. Also, emesis was observed in dogs treated with oral 1 at doses lower than the dose of oral 3 that resulted in emesis. See Table 8. Other systems for assessment of emesis also are known, such as in ferrets, allowing comparison of oral and intravenous administration of compounds. See, e.g., Strominger N. et al., Brain Res. Bull, 5, 445-451 (2001).

In each case the compound was administered as a solution, by gavage or by intravenous infusion. Multiple parameters were assessed, as is customary in a toxicology study. In the studies providing higher potential exposure to isatoribine, the plasma concentration of isatoribine was assessed by a LC/MS method. The notable GI findings were graded and are listed in Table 8.

TABLE 8

Effect on GI Tolerance in Dogs after Dosing of Isatoribine or Val-Isatoribine Ranked by Systemic Exposure (AUC) to Isatoribine in Toxicology Studies.

| Isatoribine equivalent applied dose (mg/kg) | $AUC_{0-24\,hrs}$ (µg · hr/ml) | Oral Isatoribine | | IV Isatoribine | | Oral Val-Isatoribine | |
|---|---|---|---|---|---|---|---|
| | | Emesis or loose stool | GI lesions or irritation | Emesis or loose stool | GI lesions or irritation | Emesis or loose stool | GI lesions or irritation |
| 2.5 | n.d | Neg. | Neg. | | | | |
| 5 | n.d. | + | Neg. | | | | |
| 10 | n.d. | ++ | ++ | | | | |
| 8.1 | 11.4 | | | | | Neg. | Neg. |
| 16 | 15.6 | | | | | Neg. | Neg. |
| 12.5 | 19.5 | | | Neg. | Neg. | | |
| 32 | 31.7 | | | | | Neg. | Neg. |
| 25 | 42.8 | | | Neg. | Neg. | | |
| 64 | 71 | | | | | Neg. | Neg. |
| 130 | 75.3 | | | | | + | Neg. |
| 50 | 87.8 | | | + | Neg. | | |
| 260 | 127 | | | | | ++ | Neg. |
| 390 | 180 | | | | | +++ | Neg. |
| 100 | 209 | | | ++ | Neg. | | |

For orally administered isatoribine the principal findings were related to GI tolerability as measured by GI irritancy. The clinical signs noted in Table 8 were emesis and/or loose stools. These clinical signs were more frequent in the 10 mg/kg group, and in one animal at this dose a bloody stool was noted. Gross histopathologic evaluation of the GI tract noted multiple, scattered red lesions on the intestinal mucosa in four of eight dogs at 10 mg/kg, which on microscopic evaluation revealed cellular congestion and hemorrhage, as might be expected for an ongoing localized inflammatory process. The GI effects established the NOAEL as 5 mg/kg.

Intravenously administered isatoribine resulted in emesis and/or loose stools as a common finding in dogs; this effect occurred at substantially higher applied doses than orally administered isatoribine. No lesions were seen in the GI tract either at necropsy or histopathologic evaluation of tissues. The GI toxicity did not affect the NOAEL, which was established as 12.5 mg/kg on the basis of other findings.

Orally administered val-isatoribine demonstrated a toxicology profile similar to intravenously administered isatoribine. At higher applied doses, emesis and loose stools were observed. No GI lesions were found, although this was a focus of evaluation in this study. As for intravenously administered isatoribine, the NOAEL was established on the basis of other findings. The correspondence of observed toxicity to systemic exposures of isatoribine is of interest in this study; the threshold of isatoribine AUC for observation of emesis and loose stools is similar for intravenously administered isatoribine and orally administered val-isatoribine (Table 8).

The data in Table 8 indicate that orally administered val-isatoribine provides an improved toxicity profile over orally administered isatoribine, and is consistent with the hypothesis that chemical masking of the activity of isatoribine is afforded by chemically substituting an ester for one of the hydroxyls of the nucleoside, preferably by chemically substituting an ester at the 5'-hydroxyl position of the nucleoside. Engineering this substitution to be cleavable upon entry into the body affords systemic exposure to the useful activity of the compound without the limiting GI toxicity arising from the anatomical structure of the GI tract. This enables administration of doses that are substantially higher on a molar basis than otherwise would be acceptable, with the result of greater efficacy and reduced side effects when compared to administration of the parental "unmasked" compound alone.

Assessment of Systemic Exposure to 1 (isatoribine) after Oral Dosing of Formula I Compounds

TABLE 9

Pharmacokinetic Parameters for Formula I Compounds when $R^2$ = H

| | Pharmacokinetic Parameters | | |
|---|---|---|---|
| Compound | Caco2 (nm/s) | Monkey Hepatocytes (%) | Monkey PK ((ng/ml) * hr)/(mg/kg) |
| 79 | 100 | 10 | 390 |
| 89 | 200 | 45 | 560 |
| 78 | 600 | 20 | 630 |

Caco2 Assay

In vitro drug transport assays using differentiated and P-glycoprotein-expressing Caco2 cell monolayers are widely used to predict absorption rates of candidate drug compounds across the intestinal epithelial cell barrier. See, e.g., Hilgers, A. R. et al., Pharm. Res., 20(8), 1149-55 (August 2003).

Caco-2 cells (obtained from ATCC) are grown to confluency on permeable membranes in chambers allowing access to both the apical and basolateral sides of the membrane. The intact nature of the resulting cellular membrane is assessed using transepithelial electrical resistance. The test compound is added at a known concentration to the apical side of the membrane and the rate of appearance of the compound on the basolateral side of the membrane is assessed by analysis using either HPLC or LC-MS/MS. Higher transport rates in Caco-2 cells are associated with improved gastrointestinal absorption.

The purpose of the assessment of compounds 79, 89, and 78 in this system was to determine if 89 and 78 were transported to a greater extent than 79. The findings confirm that 89 and 78 show significantly improved transport over 79.

Monkey Hepatocytes

The compounds of the present invention must be converted to 1 in the body if they are to serve as effective prodrugs. Hepatocyes often are used to assess the degree to which a compound may be transformed in the body of an animal, and it is known that such transformations may vary with hepatocytes from different species in a way that reflects metabolism in the whole animal. See Seddon T. et al., *Biochem Pharmacol.*, 38(10), 1657-65 (May 1989).

Cynomolgus monkey hepatocytes were purchased from a commercial supplier and used within 48 hours of preparation. Compounds were prepared in culture media at a concentration of 10 μm/ml and incubated in a standard system with 1,000,000 viable hepatocytes per ml for 2 hours at 37 degrees. The extent of conversion at the end of the incubation period was assessed by measuring 1 by LC-MS/MS.

The purpose of the assessment of compounds 79, 89, and 78 in this system was to determine the extent of their conversion to 1. The findings confirm that 89 and 78 are more extensively converted to 1 than is 79.

Animal PK Experiments

Assessment of the ability of compounds of the present invention to deliver 1 to the systemic circulation after oral dosing was assessed by methods well known in the art. For Tables 9 and 10, each test compound was formulated into a solution for oral dosing by dissolving the compound in either an aqueous buffer such as PBS at pH3 or in a solution containing a solubilizer such as Cremaphor, Tween80, or PEG400. The solution of the compound was dosed by oral gavage to Sprague-Dawley rats or to cynomolgus monkeys, generally using a group of three animals for each experiment. Plasma samples were collected from the animals at several time points (usually, from 6 to 12 time points were used) within 6 to 24 hours. The plasma samples were frozen quickly after collection, and thawed immediately before sample preparation for bioanalysis.

Reference values for compound 1 were obtained by similar procedures after either oral or intravenous dosing. Intravenous administration of 1 resulted in recovery of the majority (>75%) of the administered dose in the urine as intact 1; thus, measurement of 1 in the urine provided a convenient measure of systemic exposure to 1. For this reason, in some experiments the amount of 1 in urine collected over a period of 24 hours after dosing was used to assess compounds.

Bioanalysis

An aliquot (usually, 50 μL) of each sample collected in animal PK studies or in vitro studies was quenched with acetonitrile (3:1 acetonitrile-to-plasma ratio) containing an internal standard (usually, nebularine). The suspension was centrifuged at 14,000 rpm for 5-10 min. An aliquot of the resulting supernatant was transferred into a clean vial and dried under nitrogen. The dried sample was reconstituted and submitted to LC-MS/MS analysis by the MRM (multiple reaction monitoring) method. Calibration standards were prepared by serial dilution of an initial concentrated standard of the analyte with either animal plasma or cell culture media. Calibration standards were prepared for LC-MS/MS analysis as described above for animal PK samples. The LC-MS/MS analysis was performed in a batch mode with at least two sets of calibration standards, bracketing the study samples. An LC-MS/MS trace for both the analyte and the internal standard was integrated, and the ratio of their peak areas was used to calculate a relative response of analyte in both the study samples and the calibration standards. A combined calibration curve was developed by applying curve-fitting methods to responses from the calibration standards. The fitted calibration curve was used to calculate the quantity of analyte in samples. The useful dynamic range of the calibration curve was 1-5 ng/mL to 2,000-10,000 ng/mL.

PK Calculations

The plasma concentration-time profile of 1 after oral administration of a known dose of the compound was used to calculate an AUC (area-under-the-curve) of 1 in systemic circulation. The AUC was normalized according to the total theoretical content of 1 in the compound, based on molecular weight. For Table 8, the AUC was further normalized to a dose of 1 mg/kg.

From Table 8 the AUC data illustrates that compounds 89 and 78 deliver more of 1 (44%-69% increase) to the systemic circulation after oral dosing than 79.

TABLE 10

Pharmacokinetic Parameters for Formula I Compounds when $R^2 = OR^5$

| Cmpd No. | | SD rat, PO ANA245 AUC (0-24 h) | SD rat, PO ANA245 AUC (0-1 h) | Cyno Monkey, PO ANA245 AUC (0-24 h) |
|---|---|---|---|---|
| 1 | IV doses | 341 | 256 | 740 |
|   | PO doses | 23 |  | 15 |
| 14 |  | 16 |  |  |
| 30 |  | 169; 136 | 73 | 205 |
| 28 |  | 156 |  | 153 |
| 62 |  |  | 34 |  |
| 63 |  |  | 46 |  |
| 32 |  | 157 |  |  |
| 66 |  |  | 9 |  |
| 38 |  |  | 6 |  |
| 40 |  |  | 14 |  |
| 36 |  |  | 16 |  |
| 34 |  |  | 6 |  |
| 66 |  | 130 | 81; 60 | 127 |
| 68 |  |  |  | 27 |
| 51 |  |  | 0 |  |
| 72 |  |  |  | 0 |
| 70 |  |  |  | 0 |
| 61 |  |  |  | 104 |

Anti-Viral Activity of Compounds

A number of assays may be employed in accordance with the present invention in order to determine the degree of anti-viral activity of a compound of the invention such as cell culture, animal models, and administration to human subjects. The assays described herein may be used to assay viral growth over time to determine the growth characteristics of a virus in the presence of a compound of the invention.

In another embodiment, a virus and a compound of the invention are administered to animal subjects susceptible to infection with the virus. The incidence, severity, length, virus load, mortality rate of infection, etc. can be compared to the incidence, severity, length, virus load, mortality rate of infection, etc. observed when subjects are administered the virus alone (in the absence of a compound of the invention). Antivirus activity of the compound of the invention is demonstrated by a decrease in incidence, severity, length, virus load, mortality rate of infection, etc. in the presence of the compound of the invention. In a specific embodiment, the virus and the compound of the invention are administered to the animal subject at the same time. In another specific embodiment, the virus is administered to the animal subject before the compound of the invention. In another specific embodiment, the compound of the invention is administered to the animal subject before the virus.

In another embodiment, the growth rate of the virus can be tested by sampling biological fluids/clinical samples (e.g., nasal aspirate, throat swab, sputum, broncho-alveolar lavage, urine, saliva, blood, or serum) from human or animal subjects at multiple time points post-infection either in the presence or absence of a compound of the invention and measuring levels of virus. In specific embodiments, the growth rate of a virus is assayed by assessing the presence of virus in a sample after growth in cell culture, growth on a permissible growth medium, or growth in subject using any method well-known in the art, for example, but not limited to, immunoassay (e.g., ELISA; for discussion regarding ELISAs see, e.g. Ausubel et al., eds, 1994, Current Protocols in Molecular Biology, Vol. I, John Wiley & Sons, Inc., New York at 11.2.1), immunofluorescent staining, or immunoblot analysis using an antibody which immunospecifically recognizes the virus to be assayed or detection of a virus-specific nucleic acid (e.g., by Southern blot or RT-PCR analysis, etc.).

In a specific embodiment, viral titers can be determined by obtaining biological fluids/clinical samples from infected cells or an infected subject, preparing a serial dilution of the sample and infecting a monolayer of cells that are susceptible to infection with the virus (e.g. primary cells, transformed cell lines, patient tissue samples, etc) at a dilution of the virus that allows for the emergence of single plaques. The plaques can then be counted and the viral titer expressed as plaque forming units per milliliter of sample.

In one specific embodiment, the growth rate of a virus in a subject can be estimated by the titer of antibodies against the virus in the subject. Antibody serum titer can be determined by any method well-known in the art, for example, but not limited to, the amount of antibody or antibody fragment in serum samples can be quantitated by, e.g., ELISA. Additionally, in vivo activity of a Formula I compound can be determined by directly administering the compound to a test animal, collecting biological fluids (e.g., nasal aspirate, throat swab, sputum, broncho-alveolar lavage, urine, saliva, blood, or serum) and testing the fluid for anti-virus activity.

In embodiments where samples to be assayed for virus levels are biological fluids/clinical samples (e.g., nasal aspirate, throat swab, sputum, broncho-alveolar lavage, urine, saliva, blood, or serum), the samples may or may not contain in tact cells. Samples from subjects containing intact cells can be directly processed, whereas isolates without intact cells may or may not be first cultured on a permissive cell line (e.g. primary cells, transformed cell lines, patient tissue samples, etc) or growth medium (e.g., LB broth/agar, YT broth/agar, blood agar, etc.). Cell suspensions can be cleared by centrifugation at, e.g. 300×g for 5 minutes at room temperature, followed by a PBS, pH 7.4 ($Ca^{++}$ and $Mg^{++}$ free) wash under the same conditions. Cell pellets can be resuspended in a small volume of PBS for analysis. Primary clinical isolates containing intact cells can be mixed with PBS and centrifuged at 300×g for 5 minutes at room temperature. Mucus is removed from the interface with a sterile pipette tip and cell pellets can be washed once more with PBS under the same conditions. Pellets can then be resuspended in a small volume of PBS for analysis.

In another embodiment, a compound of the invention is administered to a human subject infected with a virus. The incidence, severity, length, viral load, mortality rate of infection, etc. can be compared to the incidence, severity, length, viral load, mortality rate of infection, etc. observed in human subjects infected with a virus in the absence of a compound of the invention or in the presence of a placebo. Anti-viral activity of the compound of the invention is demonstrated by a decrease in incidence, severity, length, viral load, mortality rate of infection, etc. in the presence of the compound of the invention. Any method known in the art can be used to determine anti-viral activity in a subject such as those described previously.

Additionally, in vivo activity of a Formula I compound can be determined by directly administering the compound to an animal or human subject, collecting biological fluids/clinical samples (e.g., nasal aspirate, throat swab, sputum, broncho-alveolar lavage, urine, saliva, blood, or serum) and testing the biological fluids/clinical samples for anti-viral activity (e.g., by addition to cells in culture in the presence of the virus).

Figure 2:
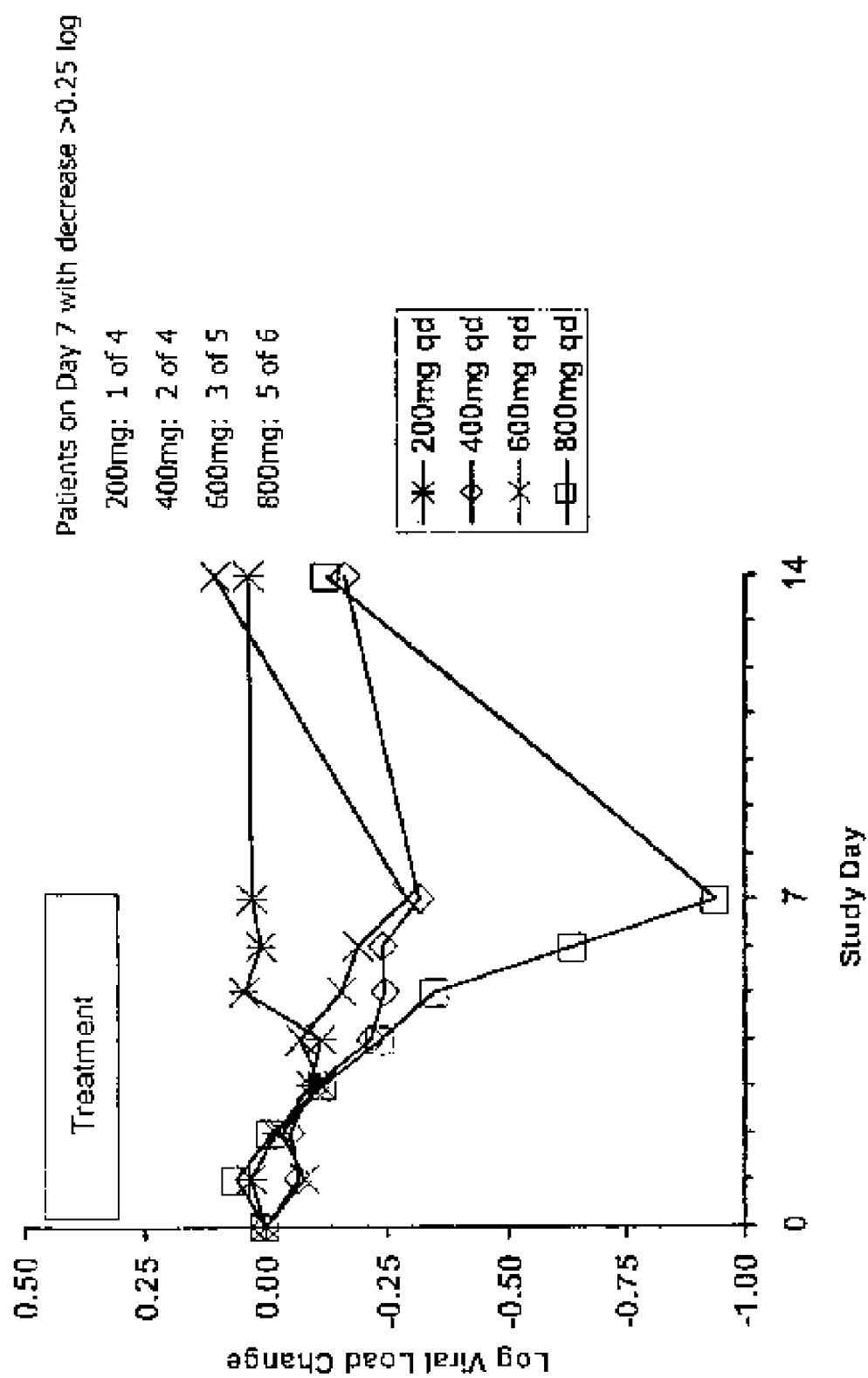
FIG. 2 is a graphical depiction of viral load changes in HCV infected patients receiving isatoribine (1).

FIG. 2: Viral Load Changes for Once Daily IV Administration of Isatoribine

Isatoribine investigational drug product was supplied as a 1 mg/mL solution in sterile normal saline contained in a 50 mL vial. Isatoribine was administered by intravenous infusion once daily for 7 days, at 200, 400, 600 or 800 mg per dose. All doses were administered by constant rate infusion over a 60-minute period, except the 800 mg dose was administered over an 80-minute period. The flow rate for each dose was as follows: 3.33 mL/min for the 200 mg dose; 6.67 mL/min for the 400 mg dose; 8.33 mL/min for the 500 mg dose; or 10.0 mL/min for the 600 mg and 800 mg dose.

Four to six patients were enrolled in each of the dose groups (200 mg, 400 mg, 600 mg and 800 mg per dose) and received once daily intravenous infusions for 7 days. Prior to dosing, a blood sample was drawn from each patient for assessment of the genotype of the HCV virus.

Plasma HCV RNA was determined at baseline (an average of 2 pre-treatment measurements taken on Day −1 or pre-treatment and on Day 1) and once daily prior to the start of the first daily isatoribine intravenous infusion on Days 2 through 7 for these daily (×7 days) dosing groups. The viral load was measured by the branched DNA method (Versant™ v3.0 bDNA assay, Bayer Diagnostics). For plasma HCV RNA, the maximum change from the pre-treatment baseline was estimated using log-transformed values.

Example: Oral Composition

Table 11 illustrates a batch formulation and a single dose unit formulation containing 100 mg of val-isatoribine.

TABLE 11

Formulation for 100 mg tablet

| Material | Percent by Weight | Quantity (mg/tablet) | Quantity (kg/batch) |
| --- | --- | --- | --- |
| val-isatoribine | 40% | 100.00 | 20.00 |
| Microcrystalline Cellulose, NF | 53.5% | 133.75 | 26.75 |
| Pluronic F-68 Surfactant | 4.0% | 10.00 | 2.00 |
| Croscarmellose Sodium Type A, NF | 2.0% | 5.00 | 1.00 |
| Magnesium Stearate, NF | 0.5% | 1.25 | 0.25 |
| Total | 100.0% | 250.00 mg | 50.00 kg |

The microcrystalline cellulose, croscarmellose sodium, and val-isatoribine components are passed through a #30 mesh screen (about 430μ to about 655μ). The Pluronic F-68® (manufactured by JRH Biosciences, Inc. of Lenexa, Kans.) surfactant is passed through a #20 mesh screen (about 457μ to about 1041μ). The Pluronic F-68® surfactant and 0.5 kgs of croscarmellose sodium are loaded into a 16 qt. twin shell tumble blender and are mixed for about 5 minutes. The mix is then transferred to a 3 cubic foot twin shell tumble blender where the microcrystalline cellulose is added and blended for about 5 minutes. The compound is added and blended for an additional 25 minutes. This pre-blend is passed through a roller compactor with a hammer mill attached at the discharge of the roller compactor and moved back to the tumble blender. The remaining croscarmellose sodium and magnesium stearate is added to the tumble blender and blended for about 3 minutes. The final mixture is compressed on a rotary tablet press with 250 mg per tablet (200,000 tablet batch size).

Example: Mucosal Composition

A concentrate is prepared by combining isatoribine, and a 12.6 kg portion of the trichloromonofluoromethane in a sealed stainless steel vessel equipped with a high shear mixer. Mixing is carried out for about 20 minutes. The bulk suspension is then prepared in the sealed vessel by combining the concentrate with the balance of the propellants in a bulk product tank that is temperature controlled to 21° to 27° C. and pressure controlled to 2.8 to 4.0 BAR. 17 ml aerosol containers which have a metered valve which is designed to provide 100 inhalations of the composition of the invention. Each container is provided with the following:

| | |
|---|---|
| val-isatoribine | 0.0120 g |
| trichloromonofluoromethane | 1.6960 g |
| dichlorodifluoromethane | 3.7028 g |
| dichlorotetrafluoroethane | 1.5766 g |
| total | 7.0000 g |

Example: Intravenous Composition

The intravenous formulation is prepared by reconstituting a compound of the invention with an appropriate liquid medium, such as water for injection (WFI) or a 5% dextrose solution. A desired concentration of the intravenous formulation can be obtained by reconstituting an appropriate amount of a compound of the invention with an appropriate volume of liquid medium. A desired concentration of the intravenous formulation provides a therapeutically effective amount of a compound of the invention to the patient, preferably a mammal, more preferably a human, in need of the intravenous pharmaceutical formulation and maintains a therapeutically effective level of a compound of the invention in the patient. The dose which is therapeutically effective will depend on the rate at which the intravenous formulation is delivered to the patient and the concentration of the intravenous formulation. For example, one vial containing a composition (e.g., 50 mg of a compound of the invention per vial) are reconstituted with a 5% dextrose solution (14 ml of 5% dextrose solution per vial) yielding a total of 25 mL of solution. The reconstituted solution is incorporated into a dextrose solution in an infusion bag and q.s. to 50 mL, resulting in a solution containing 1 mg/ml of a compound of the invention suitable for intravenous infusion administration. The preferred concentration of a compound of the invention in the liquid medium, in the infusion bag, is about 0.001 to about 3 mg/ml, preferably about 0.75 to about 1 mg/ml.

It is to be understood that the foregoing description is exemplary and explanatory in nature, and is intended to illustrate the invention and its preferred embodiments. Through routine experimentation, the artisan will recognize apparent modifications and variations that may be made without departing from the spirit of the invention. Thus, the invention is intended to be defined not by the above description, but by the following claims and their equivalents.

What is claimed is:

1. A method of increasing plasma levels of interferon comprising administering to a patient a compound represented by Formula I

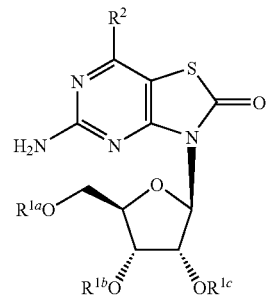

wherein:
$R^{1a}$, $R^{1b}$, and $R^{1c}$ are independently H, —C(O)$R^3$, a racemic, L-, or D- amino acid group —C(O)CH$_2$NHR$^4$, —C(O)CH(C$_{1-6}$ alkyl)NHR$^4$, or $R^{1b}$ and $R^{1c}$ are collectively —C(O)—, which together with the oxygen atoms forms a five-membered carbonate ring;
$R^2$ is H;
$R^3$ is a $C_{1-18}$ alkyl; and
$R^4$ is H, —C(O)CH(C$_{1-6}$ alkyl)NH$_2$, or —C(O)CH(CH$_2$-aryl)NH$_2$;
wherein the alkyl and aryl moieties of the foregoing groups are optionally substituted with substituents independently selected from halo, cyano, nitro, trifluoromethyl, trifluoromethoxy, $C_1$-$C_6$ alkyl, $C_2$-$C_6$ alkenyl, $C_2$-$C_6$ alkynyl, hydroxy, $C_1$-$C_6$ alkoxy, —NH$_2$, —NH-alkyl, —N(alkyl)$_2$, —NH-aryl, —N(alkyl)(aryl), —N(aryl)$_2$, —NHCHO, —NHC(O)alkyl, —NHC(O)aryl, —N(alkyl)C(O)H, —N(alkyl)C(O)alkyl, —N(aryl)C(O)H, —N(aryl)C(O)alkyl, —NHCO$_2$alkyl, —N(alkyl)CO$_2$alkyl, —NHC(O)NH$_2$, —N(alkyl)C(O)NH$_2$, —NHC(O)NH-alkyl, —NHC(O)N(alkyl)$_2$, —N(alkyl)C(O)NH-alkyl, N(alkyl)C(O)N(alkyl)$_2$, —NHSO$_2$-alkyl, —N(alkyl)SO$_2$-alkyl, —C(O)alkyl, —C(O)aryl, —OC(O)alkyl, —OC(O)aryl, —CO$_2$-alkyl, —CO$_2$-aryl, —CO$_2$H, —C(O)NH$_2$, —C(O)NH-alkyl, —C(O)N(alkyl)$_2$, —C(O)NH-aryl, —C(O)N(aryl)$_2$, —C(O)N(alkyl)(aryl), —S(O)alkyl, —S(O)aryl, —SO$_2$alkyl, —SO$_2$aryl, —SO$_2$NH$_2$, —SO$_2$NH-alkyl, and —SO$_2$N(alkyl)$_2$;
or a pharmaceutically acceptable salt thereof.

2. The method of claim 1, wherein
$R^{1a}$, $R^{1b}$, and $R^{1c}$ are independently H, —C(O)$R^3$, a racemic, L-, or D- amino acid group —C(O)CH(C$_{1-6}$ alkyl) NH$_2$; and
$R^3$ is a $C_{1-18}$ alkyl.

3. The method of claim 1, wherein
$R^{1a}$, $R^{1b}$, and $R^{1c}$ are independently H, —C(O)$R^3$, a racemic, L-, or D- amino acid group —C(O)CH(CH(CH$_3$)$_2$)NH$_2$; and
$R^3$ is CH$_3$.

4. The method of claim 1, wherein
$R^{1a}$, $R^{1b}$, and $R^{1c}$ are independently H or —C(O)$R^3$; and
$R^3$ is CH$_3$.

5. The method of claim 1, wherein
$R^{1a}$ is H and $R^{1b}$ and $R^{1c}$ are —C(O)$R^3$; and
$R^3$ is CH$_3$.

6. The method of claim 1, wherein the compound is:

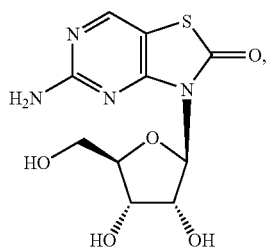

or pharmaceutically acceptable salt thereof.

7. A method of treating Hepatitis C virus infection comprising administering to a patient infected with hepatitis C virus a therapeutically effective amount of compound represented by Formula I

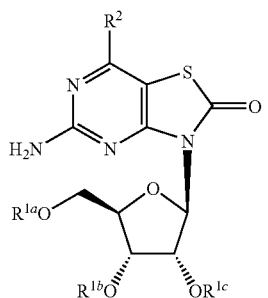

wherein:
$R^{1a}$, $R^{1b}$, and $R^{1c}$ are independently H, —C(O)$R^3$, a racemic, L-, or D- amino acid group —C(O)CH$_2$NHR$^4$, —C(O)CH(C$_{1-6}$ alkyl)NHR$^4$, or $R^{1b}$ and $R^{1c}$ are collectively —C(O)—, which together with the oxygen atoms forms a five-membered carbonate ring;
$R^2$ is H;
$R^3$ is a C$_{1-18}$ alkyl; and
$R^4$ is H, —C(O)CH(C$_{1-6}$ alkyl)NH$_2$, or —C(O)CH(CH$_2$-aryl)NH$_2$;
wherein the alkyl and aryl moieties of the foregoing groups are optionally substituted with substituents independently selected from halo, cyano, nitro, trifluoromethyl, trifluoromethoxy, C$_1$-C$_6$ alkyl, C$_2$-C$_6$ alkenyl, C$_2$-C$_6$ alkynyl, hydroxy, C$_1$-C$_6$ alkoxy, —NH$_2$, —NH—alkyl, —N(alkyl)$_2$, —NH-aryl, —N(alkyl)(aryl), —N(aryl)$_2$, —NHCHO, —NHC(O)alkyl, —NHC(O)aryl, —N(alkyl)C(O)H, —N(alkyl)C(O)alkyl, —N(aryl)C(O)H, —N(aryl)C(O)alkyl, —NHCO$_2$alkyl, —N(alkyl)CO$_2$alkyl, —NHC(O)NH$_2$, —N(alkyl)C(O)NH$_2$, —NHC(O)NH-alkyl, —NHC(O)N(alkyl)$_2$, —N(alkyl)C(O)NH-alkyl, N(alkyl)C(O)N(alkyl)$_2$, —NHSO$_2$-alkyl, —N(alkyl)SO$_2$-alkyl, —C(O)alkyl, —C(O)aryl, —OC(O)alkyl, —OC(O)aryl, —CO$_2$-alkyl, —CO$_2$-aryl, —CO$_2$H, —C(O)NH$_2$, —C(O)NH-alkyl, —C(O)N(alkyl)$_2$, —C(O)NH-aryl, —C(O)N(aryl)$_2$, —C(O)N(alkyl)(aryl), —S(O)alkyl, —S(O)aryl, —SO$_2$alkyl, —SO$_2$aryl, —SO$_2$NH$_2$, —SO$_2$NH-alkyl, and —SO$_2$N(alkyl)$_2$;
or a pharmaceutically acceptable salt thereof.

8. The method of claim 7, wherein
$R^{1a}$, $R^{1b}$, and $R^{1c}$ are independently H, —C(O)$R^3$, a racemic, L-, or D- amino acid group —C(O)CH(C$_{1-6}$ alkyl)NH$_2$; and
$R^3$ is a C$_{1-18}$ alkyl.

9. The method of claim 7, wherein
$R^{1a}$, $R^{1b}$, and $R^{1c}$ are independently H, —C(O)$R^3$, a racemic, L-, or D- amino acid group —C(O)CH(CH(CH$_3$)$_2$)NH$_2$; and
$R^3$ is CH$_3$.

10. The method of claim 7, wherein
$R^{1a}$, $R^{1b}$, and $R^{1c}$ are independently H or —C(O)$R^3$; and
$R^3$ is CH$_3$.

11. The method of claim 7, wherein
$R^{1a}$ is H and $R^{1b}$ and $R^{1c}$ are —C(O)$R^3$; and
$R^3$ is CH$_3$.

12. A method of treating Hepatitis C virus infection comprising administering to a patient infected with hepatitis C virus a therapeutically effective amount of a compound represented by the following formula:

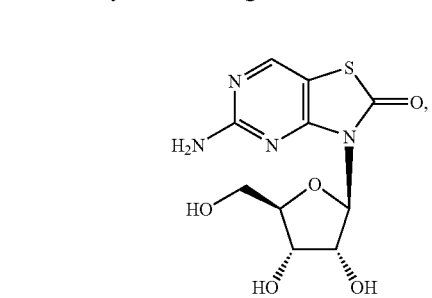

or pharmaceutically acceptable salt thereof.

* * * * *